US010407511B2

(12) United States Patent
Brinkmann et al.

(10) Patent No.: US 10,407,511 B2
(45) Date of Patent: Sep. 10, 2019

(54) COVALENTLY LINKED HELICAR-ANTI-HELICAR ANTIBODY CONJUGATES AND USES THEREOF

(71) Applicant: Hoffmann-La Roche Inc., Little Falls, NJ (US)

(72) Inventors: Ulrich Brinkmann, Weilheim (DE); Guy Georges, Habach (DE); Eike Hoffmann, Herrsching a. Ammersee (DE); Georg Tiefenthaler, Sindelsdorf (DE); Ekkehard Moessner, Kreuzlingen (CH); Stefan Dengl, Munich (DE); Achim Gaertner, Bad Heilbrunn (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/200,584

(22) Filed: Jul. 1, 2016

(65) Prior Publication Data

US 2017/0058050 A1  Mar. 2, 2017

Related U.S. Application Data

(63) Continuation of application No. PCT/EP2014/079352, filed on Dec. 29, 2014.

(30) Foreign Application Priority Data

Jan. 3, 2014 (EP) .................................... 14150087

(51) Int. Cl.
*C07K 16/44* (2006.01)
*A61K 47/68* (2017.01)
*A61K 39/00* (2006.01)
*C07K 7/08* (2006.01)
*C07K 16/26* (2006.01)

(52) U.S. Cl.
CPC .......... *C07K 16/44* (2013.01); *A61K 47/6811* (2017.08); *A61K 47/6829* (2017.08); *A61K 47/6879* (2017.08); *C07K 7/08* (2013.01); *C07K 16/26* (2013.01); *A61K 2039/505* (2013.01); *C07K 2317/24* (2013.01); *C07K 2317/31* (2013.01); *C07K 2317/34* (2013.01); *C07K 2317/565* (2013.01); *C07K 2317/622* (2013.01); *C07K 2317/624* (2013.01); *C07K 2317/94* (2013.01); *C07K 2319/31* (2013.01); *C07K 2319/70* (2013.01); *C07K 2319/73* (2013.01); *C07K 2319/75* (2013.01)

(58) Field of Classification Search
CPC .......... C07K 16/44; C07K 7/08; C07K 16/26; C07K 2317/24; C07K 2317/31; C07K 2317/34; C07K 2317/565; C07K 2317/622; C07K 2317/624; C07K 2317/94; C07K 2319/31; C07K 2319/70; C07K 2319/73; C07K 2319/75; A61K 47/6811; A61K 47/6829; A61K 47/6879; A61K 2039/505

See application file for complete search history.

(56) References Cited

U.S. PATENT DOCUMENTS

| 4,275,149 A | 6/1981 | Litman et al. |
| 4,318,980 A | 3/1982 | Boguslaski et al. |
| 4,524,025 A | 6/1985 | Geltosky |
| 4,676,980 A | 6/1987 | Segal et al. |
| 4,737,456 A | 4/1988 | Weng et al. |
| 4,816,567 A | 3/1989 | Cabilly et al. |
| 4,855,226 A | 8/1989 | Polito et al. |
| 4,855,522 A | 8/1989 | Diaz |
| 5,198,537 A | 3/1993 | Huber et al. |
| 5,208,020 A | 5/1993 | Chari et al. |
| 5,316,757 A | 5/1994 | Sherry et al. |
| 5,342,606 A | 8/1994 | Sherry et al. |
| 5,385,893 A | 1/1995 | Kiefer |
| 5,416,064 A | 5/1995 | Chari et al. |
| 5,428,139 A | 6/1995 | Kiefer et al. |
| 5,428,155 A | 6/1995 | Sherry et al. |
| 5,462,725 A | 10/1995 | Kiefer et al. |
| 5,480,990 A | 1/1996 | Kiefer et al. |
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,620,686 A | 4/1997 | Mason |
| 5,624,821 A | 4/1997 | Winter et al. |
| 5,635,483 A | 6/1997 | Pettit et al. |
| 5,648,237 A | 7/1997 | Carter |

(Continued)

FOREIGN PATENT DOCUMENTS

| DE | 3836656 A1 | 5/1990 |
| EA | 12984 B1 | 2/2010 |

(Continued)

OTHER PUBLICATIONS

Rudikoff et al., PNAS 79: 1979-1983, 1982.*

(Continued)

*Primary Examiner* — Phuong Huynh
(74) *Attorney, Agent, or Firm* — Morrison & Foerster LLP

(57) ABSTRACT

Herein is reported a conjugate comprising a helicar motif amino acid sequence containing compound and an antibody that specifically binds to the helicar motif amino acid sequence characterized by a covalent bond between the helicar motif amino acid sequence containing compound and an amino acid residue in the CDR2 of the anti-helicar antibody, whereby the CDR2 is determined according to Kabat.

9 Claims, 16 Drawing Sheets
Specification includes a Sequence Listing.

(56) References Cited

U.S. PATENT DOCUMENTS

| | | |
|---|---|---|
| 5,648,260 A | 7/1997 | Winter et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,116 A | 4/1998 | Hamann et al. |
| 5,739,294 A | 4/1998 | Kiefer et al. |
| 5,750,373 A | 5/1998 | Garrard et al. |
| 5,750,660 A | 5/1998 | Kiefer et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,804,371 A | 9/1998 | Hoss et al. |
| 5,821,337 A | 10/1998 | Carter et al. |
| 5,834,456 A | 11/1998 | Kiefer et al. |
| 5,840,523 A | 11/1998 | Simmons et al. |
| 5,869,046 A | 2/1999 | Presta et al. |
| 5,877,296 A | 3/1999 | Hamann et al. |
| 5,959,083 A | 9/1999 | Bosslet et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,528,624 B1 | 3/2003 | Idusogie et al. |
| 6,602,684 B1 | 8/2003 | Umana et al. |
| 6,630,579 B2 | 10/2003 | Chari et al. |
| 6,737,056 B1 | 5/2004 | Presta |
| 6,881,536 B1 | 4/2005 | Shah et al. |
| 6,897,044 B1 | 5/2005 | Braslawsky et al. |
| 6,946,292 B2 | 9/2005 | Kanda et al. |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,129,330 B1 | 10/2006 | Little et al. |
| 7,189,826 B2 | 3/2007 | Rodman |
| 7,332,581 B2 | 2/2008 | Presta |
| 7,371,826 B2 | 5/2008 | Presta |
| 7,498,298 B2 | 3/2009 | Doronina et al. |
| 7,504,256 B1 | 3/2009 | Ogawa et al. |
| 7,521,541 B2 | 4/2009 | Eigenbrot et al. |
| 7,527,791 B2 | 5/2009 | Adams et al. |
| 7,829,674 B2 | 11/2010 | Sabbadini et al. |
| 8,313,913 B2 | 11/2012 | Nakamura et al. |
| 8,435,784 B2 | 5/2013 | Berd et al. |
| 8,907,069 B2 | 12/2014 | Brinkmann et al. |
| 8,945,867 B2 | 2/2015 | Ogawa et al. |
| 9,050,375 B2 | 6/2015 | Bramlage et al. |
| 2001/0036923 A1 | 11/2001 | Chari et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2003/0166871 A1 | 9/2003 | Barbas, III et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0127688 A1 | 7/2004 | Winter |
| 2004/0132140 A1 | 7/2004 | Satoh et al. |
| 2005/0014934 A1 | 1/2005 | Hinton et al. |
| 2005/0026263 A1 | 2/2005 | Meares et al. |
| 2005/0031613 A1 | 2/2005 | Nakamura et al. |
| 2005/0059100 A1 | 3/2005 | Meares et al. |
| 2005/0079170 A1 | 4/2005 | Le Gall et al. |
| 2005/0079574 A1 | 4/2005 | Bond |
| 2005/0100543 A1 | 5/2005 | Hansen et al. |
| 2005/0119455 A1 | 6/2005 | Fuh et al. |
| 2005/0123546 A1 | 6/2005 | Umana et al. |
| 2005/0163782 A1 | 7/2005 | Glaser et al. |
| 2005/0233382 A1 | 10/2005 | Presta |
| 2005/0238649 A1 | 10/2005 | Doronina et al. |
| 2005/0260186 A1 | 11/2005 | Bookbinder et al. |
| 2005/0266000 A1 | 12/2005 | Bond et al. |
| 2005/0276802 A1 | 12/2005 | Adams et al. |
| 2005/0276805 A1 | 12/2005 | Hanai et al. |
| 2006/0025576 A1 | 2/2006 | Miller et al. |
| 2006/0104968 A1 | 5/2006 | Bookbinder et al. |
| 2006/0194291 A1 | 8/2006 | Presta |
| 2007/0061900 A1 | 3/2007 | Murphy et al. |
| 2007/0092940 A1 | 4/2007 | Eigenbrot et al. |
| 2007/0117126 A1 | 5/2007 | Sidhu et al. |
| 2007/0134759 A1 | 6/2007 | Nishiya et al. |
| 2007/0160598 A1 | 7/2007 | Dennis et al. |
| 2007/0166303 A1 | 7/2007 | Hanai et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0241884 A1 | 10/2008 | Shitara et al. |
| 2009/0002360 A1 | 1/2009 | Chen et al. |
| 2009/0093618 A1 | 4/2009 | Meares et al. |
| 2010/0111856 A1 | 5/2010 | Gill et al. |
| 2010/0143934 A1 | 6/2010 | Herzog et al. |
| 2015/0166670 A1 | 6/2015 | Castoldi et al. |
| 2015/0232577 A1 | 8/2015 | Brinkmann et al. |
| 2015/0238628 A1 | 8/2015 | Brinkmann et al. |
| 2015/0258209 A1 | 9/2015 | Benz et al. |
| 2016/0324984 A1 | 11/2016 | Brinkmann et al. |
| 2017/0058051 A1 | 3/2017 | Brinkmann et al. |
| 2017/0114150 A1 | 4/2017 | Brinkmann et al. |

FOREIGN PATENT DOCUMENTS

| | | |
|---|---|---|
| EP | 0 077 896 A1 | 5/1983 |
| EP | 0 098 179 A2 | 1/1984 |
| EP | 0 404 097 A2 | 12/1990 |
| EP | 0 425 235 A2 | 5/1991 |
| EP | 0 425 235 B1 | 5/1991 |
| EP | 1 870 459 A1 | 12/2007 |
| JP | S58-046072 A | 3/1983 |
| JP | 2010-501187 A | 1/2010 |
| JP | 2012-518892 A | 8/2012 |
| RU | 2219949 C2 | 12/2003 |
| RU | 2005104430 A | 8/2005 |
| RU | 2010108429 A | 9/2011 |
| RU | 2450020 C2 | 5/2012 |
| WO | WO-1991/06305 A1 | 5/1991 |
| WO | WO-1992/04053 A1 | 3/1992 |
| WO | WO-1993/01161 A1 | 1/1993 |
| WO | WO-1993/08829 A1 | 5/1993 |
| WO | WO-1993/16185 A2 | 8/1993 |
| WO | WO-1993/16185 A3 | 8/1993 |
| WO | WO-1993/21232 A1 | 10/1993 |
| WO | WO-1994/11026 A2 | 5/1994 |
| WO | WO-1994/29351 A2 | 12/1994 |
| WO | WO-1994/29351 A3 | 12/1994 |
| WO | WO-1995/09917 A1 | 4/1995 |
| WO | WO-1996/027011 A1 | 9/1996 |
| WO | WO-1997/01580 A1 | 1/1997 |
| WO | WO-1997/25069 A1 | 7/1997 |
| WO | WO-1997/30087 A1 | 8/1997 |
| WO | WO-1998/50431 A2 | 11/1998 |
| WO | WO-1998/50431 A3 | 11/1998 |
| WO | WO-1998/58964 A1 | 12/1998 |
| WO | WO-1999/22764 A1 | 5/1999 |
| WO | WO-1999/51642 A1 | 10/1999 |
| WO | WO-2000/023053 A2 | 4/2000 |
| WO | WO-2000/023053 A3 | 4/2000 |
| WO | WO-2000/50088 A2 | 8/2000 |
| WO | WO-2000/50088 A3 | 8/2000 |
| WO | WO-2000/61739 A1 | 10/2000 |
| WO | WO-2001/29246 A1 | 4/2001 |
| WO | WO-2001/34651 A1 | 5/2001 |
| WO | WO-2001/77342 A1 | 10/2001 |

(56) References Cited

FOREIGN PATENT DOCUMENTS

| WO | WO-2002/31140 A1 | 4/2002 |
|---|---|---|
| WO | WO-2003/011878 A2 | 2/2003 |
| WO | WO-2003/011878 A3 | 2/2003 |
| WO | WO-2003/084570 A1 | 10/2003 |
| WO | WO-2003/085107 A1 | 10/2003 |
| WO | WO-2003/085119 A1 | 10/2003 |
| WO | WO-2004/009116 A2 | 1/2004 |
| WO | WO-2004/009116 A3 | 1/2004 |
| WO | WO-2004/045642 A1 | 6/2004 |
| WO | WO-2004/056312 A2 | 7/2004 |
| WO | WO-2004/056312 A3 | 7/2004 |
| WO | WO-2004/065569 A2 | 8/2004 |
| WO | WO-2004/065569 A3 | 8/2004 |
| WO | WO-2005/004809 A2 | 1/2005 |
| WO | WO-2005/035586 A1 | 4/2005 |
| WO | WO-2005/035778 A1 | 4/2005 |
| WO | WO-2005/053742 A1 | 6/2005 |
| WO | WO-2005/058940 A2 | 6/2005 |
| WO | WO-2005/058940 A3 | 6/2005 |
| WO | WO-2005/100402 A1 | 10/2005 |
| WO | WO-2006/020258 A2 | 2/2006 |
| WO | WO-2006/020258 A3 | 2/2006 |
| WO | WO-2006/029879 A2 | 3/2006 |
| WO | WO-2006/029879 A3 | 3/2006 |
| WO | WO-2006/044908 A2 | 4/2006 |
| WO | WO-2006/044908 A3 | 4/2006 |
| WO | WO-2007/024715 A2 | 3/2007 |
| WO | WO-2007/024715 A3 | 3/2007 |
| WO | WO-2007/065808 A2 | 6/2007 |
| WO | WO-2007/065808 A3 | 6/2007 |
| WO | WO-2007/109254 A2 | 9/2007 |
| WO | WO-2007/109254 A3 | 9/2007 |
| WO | WO-2007/130697 A2 | 11/2007 |
| WO | WO-2007/130697 A3 | 11/2007 |
| WO | WO-2008/022349 A2 | 2/2008 |
| WO | WO-2008/022349 A3 | 2/2008 |
| WO | WO-2008/077546 A1 | 7/2008 |
| WO | WO-2009/022328 A2 | 2/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/034651 A1 | 4/2010 |
| WO | WO-2010/045388 A2 | 4/2010 |
| WO | WO-2010/045388 A3 | 4/2010 |
| WO | WO-2010/056893 A1 | 5/2010 |
| WO | WO-2010/098992 A1 | 9/2010 |
| WO | WO-2010/112193 A1 | 10/2010 |
| WO | WO-2010/115589 A1 | 10/2010 |
| WO | WO-2010/119704 A1 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/003780 A1 | 1/2011 |
| WO | WO-2011/032022 A1 | 3/2011 |
| WO | WO-2012/075037 A1 | 6/2012 |
| WO | WO-2012/093068 A1 | 7/2012 |
| WO | WO-2012/143379 A1 | 10/2012 |
| WO | WO-2013/106577 A2 | 7/2013 |
| WO | WO-2013/106577 A3 | 7/2013 |
| WO | WO-2014/006124 A1 | 1/2014 |
| WO | WO-2015/101587 A1 | 7/2015 |
| WO | WO-2015/101589 A1 | 7/2015 |

OTHER PUBLICATIONS

Colman et al., Research in Immunology 145: 33-36, 1994.*
Kussie et al., J. Immunol. 152: 146-152, 1994.*
Chen et al., EMBO J., 14: 2784-2794, 1995.*
Wu et al., J Mol Biol 294: 151-162, 1999.*
Albert et al. "Direct Synthesis of [DOTA-DPhe$^1$]-Octreotide and [DOTA-DPhe$^1$, Tyr$^3$]-Octreotide (SMT487): Two Conjugates for Systemic Delivery of Radiotherapeutical Nuclides to Somatostatin Receptor Positive Tumors in Man," *Bioorganic & Medicinal Chemistry Letters* 8:1207-1210, (1998).
Almagro et al. "Humanization of Antibodies," *Frontiers in Bioscience* 13:1619-1633, (Jan. 1, 2008).
Atwell et al. "Stable Heterodimers from Remodeling the Domain Interface of a Homodimer Using a Phage Display Library," *J. Mol. Biol.* 270:26-35, (1997).
AvantGen, Inc. "AvantGen's Antibody Humanization and Discovery Technologies—GermlinerTM Antibodies: An Effective and Proprietary Technology for Humanizing Antibodies Based on Epitope-Guided Selection," (Jul. 27, 2009), 4 pages.
Baca et al. "Antibody Humanization Using Monovalent Phage Display," *The Journal of Biological Chemistry* 272(16):10678-10684, (Apr. 18, 1997).
Bagci et al. "Monoclonal Anti-biotin Antibodies Simulate Avidin in the Recognition of Biotin," *FEBS* 322(1):47-50, (May 1993).
Bera et al. "Comparison of Recombinant Immunotoxins Against Le$^Y$ Antigen Expressing Tumor Cells: Influence of Affinity, Size, and Stability," *Bioconjugate Chemistry* 9(6):736-743, (Nov.-Dec. 1998; e-published on Oct. 20, 2008).
Berger et al. "Production of Antibodies that Bind Biotin and Inhibit Biotin Containing Enzymes," *Biochemistry* 14(11):2338-2342, (1975).
Blend et al. "Labeling anti-HER2/neu Monoclonal Antibodies With $^{111}$in and $^{90}$Y Using a Bifunctional DTPA Chelating Agent," *Cancer Biotherapy & Radiopharmaceuticals* 18(3):355-363, (2003).
Boerner et al. "Production of Antigen-Specific Human Monoclonal Antibodies from in Vitro-Primed Human Splenocytes," *The Journal of Immunology* 147(1):86-95, (Jul. 1, 1991).
Brennan et al. "Preparation of Bispecific Antibodies by Chemical Recombination of Monoclonal Immunoglobulin $G_1$ Fragments," *Science* 229:81-83, (Jul. 5, 1985).
Briggs et al. "Synthesis of Functionalised Fluorescent Dyes and Their Coupling to Amines and Amino Acids," *J. Chem. Soc., Perkin-Trans.* 1:1051-1058, (1997).
Brinkley. "A Brief Survey of Methods for Preparing Protein Conjugates with Dyes, Haptens and Crosslinking Reagents," *Bioconjugate Chem.* 3(1):2-13, (Jan. 1992).
Brodeur et al. "Mouse-Human Myeloma Partners for the Production of Heterohybridomas," in Chapter 4 of *Monoclonal Antibody Production Techniques and Applications*, Marcel Dekker, Inc., New York, pp. 51-63, (1987).
Brüggemann et al. "Comparison of the Effector Functions of Human Immunoglobulins Using a Matched Set of Chimeric Antibodies," *J. Exp. Med.* 166:1351-1361, (Nov. 1, 1987).
Cahn et al. "Specification of Molecular Chirality," *Angew. Chem. Int. Ed. Engl.* 5(4):385-415, (1966).
Camera et al. "Comparative Biodistribution of Indium- and Yttrium-Labeled B3 Monoclonal Antibody Conjugated to Either 2-(p-SCN-Bz)-6-Methyl-DTPA (1B4M-DTPA) or 2-(p-SCN-Bz)-1,4,7,10-Tetraazacyclododecane Tetraacetic Acid (2B-DOTA)," *European Journal of Nuclear Medicine* 21(7):640-646, (Jul. 1994).
Camera et al. "Evaluation of a New DTPA-Derivative Chelator: Comparative Biodistribution and Imaging Studies of $^{111}$in-Labeled B3 Monoclonal Antibody in Athymic Mice Bearing Human Epidermoid Carcinoma Xenografts," *Nucl. Med. Biol.* 20(8):955-962, (1993).
Cao et al. "Development of a Bispecific Monoclonal Antibody as a Universal Immunoprobe for Detecting Biotinylated Macromolecules," *Journal of Immunological Methods* 220:85-91, (1998).
Carter et al. "Humanization of an Anti-p185$^{HER2}$ Antibody for Human Cancer Therapy," *PNAS* 89:4285-4289, (May 1992).
Chari et al. "Immunoconjugates Containing Novel Maytansinoids: Promising Anticancer Drugs," *Cancer Research* 52:127-131, (Jan. 1, 1992).
Charlton. "Expression and Isolation of Recombinant Antibody Fragments in *E. coli*," Chapter 14 in *Methods in Molecular Biology*, LO, B.K.C. (ed.), Humana Press, Totowa, NJ, 248:245-254, (2003).
Chen et al. "MicroPET and Autoradiographic Imaging of Breast Cancer $a_v$-Integrin Expression Using $^{18}$F- and $^{64}$Cu-Labeled RGD Peptide," *Bioconjugate Chem.* 15(1):41-49, (2004, e-published on Dec. 30, 2003).

(56) References Cited

OTHER PUBLICATIONS

Chen et al. "Selection and Analysis of an Optimized Anti-VEGF Antibody: Crystal Structure of an Affinity-Matured Fab in Complex with Antigen," *J. Mol. Biol.* 293:865-881, (1999).
Chothia et al. "Canonical Structures for the Hypervariable Regions of Immunoglobulins," *J. Mol. Biol.* 196:901-917, (1987).
Chowdhury. "Engineering Hot Spots for Affinity Enhancement of Antibodies," Chapter 11 in *Methods in Molecular Biology*, Welschof, M (ed.) et al., Humana Press Inc., Totowa, NJ, 207:179-196, (2003).
Chowdhury. "Targeting Random Mutations to Hotspots in Antibody Variable Domains for Affinity Improvement," Chapter 24 in *Methods in Molecular Biology*, O'Brien, P.M. (ed.) et al., Himana Press Inc., Totowa, NJ, 178:269-285, (2001).
Clackson et al. "Making Antibody Fragments Using Phage Display Libraries," *Nature* 352:624-628, (Aug. 15, 1991).
Clynes et al. "Fc Receptors are Required in Passive and Active Immunity to Melanoma," *Proc. Natl. Acad. Sci. USA* 95:652-656, (Jan. 1998).
Collaborative Computational Project, No. 4 "The CCP4 suite: programs for protein crystallography," *Acta Crystallogr. Section D.* 50(Pt. 5):760-763, (1994).
Coloma et al. "Design and Production of Novel Tetravalent Bispecific Antibodies" *Nature Biotech* 15(2):159-163, (Feb. 1997).
Cragg et al. "Complement-Mediated Lysis by Anti-CD20 Mab Correlates with Segregation into Lipid Rafts," *Blood* 101(3):1045-1052, (Feb. 1, 2003).
Cragg et al. "Antibody Specificity Controls in Vivo Effector Mechanisms of Anti-CD20 Reagents," *Blood* 103(7):2738-2743, (Apr. 1, 2004).
Cunningham et al. "High-Resolution Epitope Mapping of Hgh-Receptor Interactions by Alanine-Scanning Mutagenesis," *Science* 244:1081-1085, (Jun. 1989).
Dakshinamurti et al. "Production and Characterization of a Monoclonal Antibody to Biotin," *Biochem. J.* 237:477-482, (1986).
Dall'Acqua et al. "Antibody Humanization by Framework Shuffling," *Methods* 36:43-60, (2005).
De León-Rodriguez et al. "Solid-Phase Synthesis of DOTA-Peptides," *Chem. Eur. J.* 10:1149-1155, (2004).
Debinski et al. "Monovalent Immunotoxin Containing Truncated Form of Pseudomonas Exotoxin as Potent Antitumor Agent," *Cancer Research* 52(19):5379-5385, (Oct. 1, 1992).
Debinski et al. "An Immunotoxin with Increased Activity and Homogeneity Produced by Reducing the Number of Lysine Residues in Recombinant Pseudomonas Exotoxin," *Bioconjugate Chem.* 5(1):40-46, (Jan. 1994).
Decarie et al. "Development of Digoxigenin-Labeled Peptide: Application to Chemiluminoenzyme Immunoassay of Bradykinin in Inflamed Tissues," *Peptides* 15(3):511-518, (1994).
DeNardo et al. "Comparison of 1,4,7,10-Tetraazacyclododecane-N,N'N"N'''-Tetraacetic Acid (DOTA)-Peptide-ChL6, a Novel Immunoconjugate with Catabolizable Linker, to 2-Iminothiolane-2-[p-(Bromoacetamido)benzyl]-DOTA-ChL6 in Breast Cancer Xenografts," *Clinical Cancer Research* 4(10):2483-2490, (Oct. 1, 1998).
Dengl et al. "Hapten-Directed Spontaneous Disulfide Shuffling: A Universal Technology for Site-Directed Covalent Coupling of Payloads to Antibodies," *FASEB J* 29(5):1763-1779, (May 2015; e-published on Feb. 10, 2015).
Dermer. "Another Anniversary for the War on Cancer," *Bio/Technology* 12:320, (Mar. 1994).
Doppalapudi et al. "Chemical Generation of Bispecific Antibodies," *PNAS* 107(52):22611-22616, (Dec. 28, 2010).
Dubowchik et al. "Doxorubicin Immunoconjugates Containing Bivalent, Lysosomally-Cleavable Dipeptide Linkages," *Bioorganic & Medicinal Chemistry Letters* 12:1529-1532, (2002).
Duncan et al. "The Binding Site for C1q on IgG," *Nature* 332:738-740, (Apr. 21, 1988).
Emsley et al. "Features and Development of Coot," *Acta Crystallographica D Biological Crystallography* D66:486-501, (2010).

Fellouse et al. "Synthetic Antibodies from a Four-Amino-Acid Code: A Dominant Role for Tyrosine in Antigen Recognition," *PNAS* 101(34):12467-12472, (Aug. 24, 2004).
Fischer et al. "Bispecific Antibodies: Molecules that Enable Novel Therapeutic Strategies," *Pathobiology* 74:3-14, (2007).
Flatman et al. "Process Analytics for Purification of Monoclonal Antibodies," *Journal of Chromatography B.* 848:79-87, (2007; e-published on Dec. 11, 2006).
Fraker et al "Protein and Cell Membrane Iodinations with a Sparingly Soluble Chloroamide, 1, 3, 4, 6-Tetrachloro-3a, 6a-Diphennylglycoluril," *Biochem. Biophys. Res. Commun.* 80(4):849-857, (Feb. 28, 1978).
Gazzano-Santoro et al. "A Non-Radioactive Complement-Dependent Cytotoxicity Assay for Anti-CD20 Monoclonal Antibody," *Journal of Immunological Methods* 202:163-171, (1997).
Gerngross. "Advances in the Production of Human Therapeutic Proteins in Yeasts and Filamentous Fungi," *Nature Biotechnology* 22(11):1409-1414, (Nov. 2004).
Graham et al. "Characteristics of a Human Cell Line Transformed by DNA from Human Adenovirus Type 5," *J. Gen Virol.* 36:59-74, (1977).
Griffiths et al. "Human Anti-Self Antibodies with High Specificity from Phage Display Libraries," *The EMBO Journal* 12(2):725-734, (1993).
Gruber et al. "Efficient Tumor Cell Lysis Mediated by a Bispecific Single Chain Antibody Expressed in *Escherichia coli*," *Journal of Immunology* 152:5368-5374, (1994).
Guyer et al. "Immunoglobulin Binding by Mouse Intestinal Epithelial Cell Receptors," *The Journal of Immunology* 117(2):587-593, (Aug. 1976).
Hanes et al. "Ribosome Display Efficiently Selects and Evolves High-Affinity Antibodies in Vitro From Immune Libraries," *Proceedings of the National Academy of Sciences* 95(24):14130-14135, (Nov. 24, 1998).
Hansen et al. "A Recombinant Immunotoxin Targeting CD22 With Low Immunogenicity, Low Nonspecific Toxicity, and High Antitumor Activity in Mice," *Journal of Immunotherapy* 33(3):297-304, (Apr. 2010).
Hellström et al. "Strong Antitumor Activities of IgG3 Antibodies to a Human Melanoma-Associated Ganglioside," *PNAS* 82:1499-1502, (Mar. 1985).
Hellstrom et al. "Antitumor Effects of L6, an IgG2a Antibody that Reacts with Most Human Carcinomas," *PNAS* 83:7059-7063, (Sep. 1986).
Hermanson. "Buckyballs, Fullerenes, and Carbon Nanotubes," in Chapter 15 of *Bioconjugate Techniques*, Academic Press, San Diego, pp. 627-648, (1996).
Hermanson. "Chemoselective Ligation: Bioorthogonal Reagents" in Chapter 17 of *Bioconjugate Techniques*, Academic Press, San Diego, pp. 666-706, (1996).
Hermanson. "Functional Targets," in Chapter 1 of *Bioconjugate Techniques*, Academic Press, San Diego, pp. 3-168, (1996).
Hermanson. "Mass Tags and Isotope Tags," in Chapter 16 of *Bioconjugate Techniques*, Academic Press, San Diego, pp. 649-665, (1996).
Hinman et al. "Preparation and Characterization of Monoclonal Antibody Conjugates of the Calicheamicins: A Novel and Potent Family of Antitumor Antibiotics," *Cancer Research* 53:3336-3342, (Jul. 15, 1993).
Hnatowich et al. "The Preparation of DTPA-Coupled Antibodies Radiolabeled With Metallic Radionuclides: An Improved Method," *Journal of Immunological Methods* 65:147-157, (1983).
Hoffmann et al. "PK Modulation of Haptenylated Peptides via Non-Covalent Antibody Complexation," *Journal of Controlled Release* 171(1):48-56, (Oct. 10, 2013, e-published on Jun. 22, 2013).
Holliger et al. "Engineered Antibody Fragments and the Rise of Single Domains," *Nature Biotech* 23(9):1126-1136, (Sep. 2005; e-published on Sep. 7, 2005).
Holliger et al. ""Diabodies": Small Bivalent and Bispecific Antibody Fragments," *Proc. Natl. Acad. Sci. USA* 90:6444-6448, (Jul. 1993).

(56) References Cited

OTHER PUBLICATIONS

Hoogenboom et al. "By-Passing Immunisation. Human Antibodies from Synthetic Repertoires of Germline $V_H$ Gene Segments Rearranged in Vitro," *J. Mol. Biol.* 227:381-388, (1992).
Hoogenboom. "Overview of Antibody Phage-Display Technology and its Applications," in Chapter 1 of *Methods in Molecular Biology*, O'Brien, P.M. (ed.) et al., Humana Press Inc., Totowa, NJ, 178:1-37, (2002).
Hudson et al. "Engineered Antibodies," *Nature Medicine* 9(1):129-134, (Jan. 2003).
Hwang et al. "Use of Human Germline Genes in a CDR Homology-based Approach to Antibody Humanization," *Methods* 36(1):35-42, (May 2005).
Idusogie et al. "Mapping of the C1q Binding Site on Rituxan, a Chimeric Antibody with a Human IgG1 Fc," *The Journal of Immunology* 164:4178-4184, (2000).
International Search Report dated Apr. 22, 2015 for International Application No. PCT/EP2014/079354, filed on Dec. 29, 2014, five pages.
International Search Report dated Aug. 20, 2013, for PCT Patent Application No. PCT/EP2013/064090, filed on Jul. 4, 2013, five pages.
International Search Report dated Mar. 11, 2015 for International Application No. PCT/EP2014/079352 filed on Dec. 29, 2014, five pages.
International Search Report dated Nov. 19, 2013, for International Application No. PCT/EP2013/064100, filed on Jul. 4, 2013, four pages.
Izard et al. "An Improved Method for Labeling Monoclonal Antibodies With Samarium-153: Use of the Bifunctional Chelate 2-(p-Isothiocyanatobenzyl)-6-Methyldiethylenetriaminepentaacetic Acid," *Bioconjugate Chem.* 3(4):346-350, (1992).
Jeffrey S.C. et al. "Dipeptide-based Highly Potent Doxorubicin Antibody Conjugates," *Bioorganic Medicinal Chemistry Letters* 16:358-362, (2006, e-pub. Nov. 3, 2005).
Kabsch. "Automatic Processing of Rotation Diffraction Data from Crystals of Initially Unknown Symmetry and Cell Constants," *Journal of Applied Crystallography* 26:795-800, (1993).
Kam et al. "Carbon Nanotubes as Multifunctional Biological Transporters and Near-Infrared Agents for Selective Cancer Cell Destruction," *PNAS* 102(33):11600-11605, (Aug. 16, 2005).
Kanda et al. "Comparison of Cell Lines for Stable Production of Fucose-Negative Antibodies with Enhanced ADCC," *Biotechnology and Bioengineering* 94:680-688, (2006; e-published on Apr. 11, 2006).
Kashmiri et al. "SDR grafting—A New Approach to Antibody Humanization," *Methods* 36:25-34, (2005).
Kim et al. "Localization of the Site of the Murine IgG1 Molecule that is Involved in Binding to the Murine Intestinal Fc Receptor," *Eur. J. Immunol.* 24:2429-2434, (1994).
Kindt et al. "Antigens and Antibodies," in Chapter 4 of *Kuby Immunology*, 6th ed., W.H. Freeman and Co., N.Y, pp. 91, (2007), 14 pages.
King et al. "Monoclonal Antibody Conjugates of Doxorubicin Prepared With Branched Peptide Linkers: Inhibition of Aggregation by Methoxytriethyleneglycol Chains," *J. Med. Chem.* 45:4336-4343, (2002; e-published on Aug. 14, 2002).
Klimka. "Human Anti-CD30 recombinant Antibodies by guided Phage Antibody Selection Using Cell Panning," *British Journal of Cancer* 83(2):252-260, (2000).
Klussman et al. "Secondary mAb--vcMMAE Conjugates are Highly Sensitive Reporters of Antibody Internalization via the Lysosome Pathway," *Bioconjugate Chemistry* 15(4):765-773, (2004, e-published on Jun. 18, 2004).
Kobayashi et al. "Evaluation of the in Vivo Biodistribution of Indium-111 and Yttrium-88 Labeled Dendrimer-1 B4M-DTPA and Its Conjugation With Anti-Tac Monoclonal Antibody," *Bioconjugate Chem.* 10(1):103-111, (1999, e-published on Dec. 10, 1998).
Kobayashi et al. "Evaluation of the in Vivo Biodistribution of Yttrium-Labeled Isomers of CHX-DTPA-Conjugated Monoclonal Antibodies," *J. Nucl. Med.* 39:829-836, (1998).
Kohen et al. "Preparation and Properties of Anti-biotin Antibodies," *Methods Enzymology* 279:451-463, (1997).
Kostelny et al. "Formation of a Bispecific Antibody by the Use of Leucine Zippers," *The Journal of Immunology* 148(5):1547-1553, (Mar. 1, 1992).
Kozbor. "A Human Hybrid Myeloma for Production of Human Monoclonal Antibodies," *The Journal of Immunology* 133(6):3001-3005, (Dec. 1984).
Kratz et al. "Prodrugs of Anthracyclines in Cancer Chemotherapy," *Current Medicinal Chemistry* 13(5):477-523, (2006).
Kukis et al. "Optimized Conditions for Chelation of Yttrium-90-Dota Immunoconjugates," *The Journal of Nuclear Medicine* 39(12):2105-2110, (Dec. 1998).
Laskowski. "Procheck: A Program to Check the Stereochemical Quality of Protein Structures," *J. Appl. Crystallogr.* 26:283-291, (1993).
Lee et al. "Specific Localization, Gamma Camera Imaging, and Intracellular Trafficking of Radiolabelled Chimeric Anti-G(d3) Ganglioside Monoclonal Antibody KM871 in SK-MEL-28 Melanoma Xenografts," *Cancer Research* 61(11):4474-4482, (Jun. 1, 2001).
Lee et al., "Bivalent Antibody Phage Display Mimics Natural Immunoglobulin," *Journal of Immunological Methods* 284:119-132, (2004).
Lee et al. "High Affinity Human Antibodies from Phage Displayed Synthetic Fab Libraries with a Single Framework Scaffold," *J. Mol. Biol.* 340:1073-1093, (2004).
Lewis et al. "An Improved Method for Conjugating Monoclonal Antibodies with N-Hydroxysulfosuccinimidyl DOTA" *Bioconjugate Chem.* 12(2):320-324, (2001, e-pub. Mar. 6, 2011).
Li et al. "Human Antibodies for Immunotherapy Development Generated via a Human B Cell Hybridoma Technology," *PNAS* 103(10):3557-3562, (Mar. 7, 2006).
Li et al. "Optimization of Humanized IgGs in Glycoengineered Pichia Pastoris," *Nature Biotechnology* 24(2):210-215, (Feb. 2006; e-published on Jan. 22, 2006).
Li et al. "Vinyl Sulfone Bifunctional Derivatives of DOTA Allow Sulfhydryl- or Amino-Directed Coupling to Antibodies. Conjugates Retain Immunoreactivity and Have Similar Biodistributions," *Bioconjugate Chem.* 13:110-115, (2002, e-published on Dec. 14, 2001).
Lode et al. "Targeted Therapy with a Novel Enediyene Antibiotic Calicheamicin $\theta^1_1$ Effectively Suppresses Growth and Dissemination of Liver Metastases in a Syngeneic Model of Murine Neuroblastoma," *Cancer Research* 58:2925-2928, (Jul. 15, 1998).
Lonberg. "Fully Human Antibodies from Transgenic Mouse and Phage Display Platforms," *Curr. Opin. Immunol.* 20:450-459, (2008; e-published on Jul. 21, 2008).
Lonberg. "Human Antibodies from Transgenic Animals," *Nature Biotechnology* 23(9):1117-1125, (Sep. 2005; e-published on Sep. 7, 2005).
Maccallum et al. "Antibody-Antigen Interactions: Contact Analysis and Binding Site Topography," *J. Mol. Biol.* 262:732-745, (1996).
Manheimer-Lory et al. "Lupus-specific Antibodies Reveal an Altered Pattern of Somatic Mutation," *J. Clin. Invest.* 100(10):2538-2546, (Nov. 1997).
Mardirossian et al. "The Stability in Liver Homogenates of Indium-111 and Yttrium-90 Attached to Antibody via Two Popular Chelators," *Nucl. Med. Biol.* 20(1):65-74, (1993).
Marks et al. "By-Passing Immunization. Human Antibodies from V-Gene Libraries Displayed on Phage," *J. Mol. Biol.* 222:581-597, (1991).
Marks et al. "Selection of Human Antibodies from Phage Display Libraries," Chapter 8 in *Methods in Molecular Biology*, LO, B.K.C. (ed.), Humana Press Inc., Totowa, NJ, 248:161-176, (2004), 29 pages.
Mather. "Establishment and Characterization of Two Distinct Mouse Testicular Epithelial Cell Lines," *Biology of Reproduction* 23:243-252, (1980).

(56) References Cited

OTHER PUBLICATIONS

Mather et al. "Culture of Testicular Cells in Hormone-Supplemented Serum-Free Medium," *Annals N.Y. Acad. Sci.* 383:44-68, (1982).
McCafferty et al. "Phage Antibodies: Filamentous Phage Displaying Antibody Variable Domains," *Nature* 348:552-554, (Dec. 6, 1990).
Meares et al. "Conjugation of Antibodies With Bifunctional Chelating Agents: Isothiocyanate and Bromoacetamide Reagents, Methods of Analysis, and Subsequent Addition of Metal Ions," *Analytical Biochemistry* 142:68-78, (1984).
Meares et al. "Macrocyclic Chelates of Radiometals for Diagnosis and Therapy," *Br. J. Cancer* 62(Suppl. X):21-26, (1990).
Merchant et al. "An Efficient Route to Human Bispecific IgG," *Nature Biotechnology* 16:677-681, (Jul. 1998).
Metz et al. "Bispecific Digoxigenin-binding Antibodies for Targeted Payload Delivery," *PNAS* 108(20):8194-8199, (May 17, 2011).
Miederer et al. "Pharmacokinetics, Dosimetry, and Toxicity of the Targetable Atomic Generator, $^{225}$Ac-HuM195, in Nonhuman Primates," *The Journal of Nuclear Medicine* 45(1):129-137, (Jan. 2004).
Mier et al. "Conjugation of DOTA Using Isolated Phenolic Active Esters: The Labeling and Biodistribution of Albumin as Blood Pool Marker," *Bioconjugate Chem.* 16(1):237-240, (2005; e-published on Dec. 7, 2004).
Milstein. "Hybrid Hybridomas and Their Use in Immunohistochemistry," *Nature* 305:537-540, (Oct. 6, 1983).
Mirzadeh et al. "Radiometal Labeling of Immunoproteins: Covalent Linkage of 2-(4-Isothiocyanatobenzyl)Diethylenetriaminepentaacetic Acid Ligands to Immunoglobulin," *Bioconjugate Chem.* 1(1):59-65, (1990).
Mitchell et al. "Targeting Primary Human Ph$^+$ B-cell Precursor Leukemia-engrafted SCID Mice Using Radiolabeled Anti-CD19 Monoclonal Antibodies," *The Journal of Nuclear Medicine* 44(7):1105-1112, (Jul. 2003).
Morrison et al. "Chimeric Human Antibody Molecules: Mouse Antigen-Binding Domains with Human Constant Region Domains," *PNAS* 81:6851-6855, (Nov. 1984).
Morrison. "Two Heads are Better Than One," *Nature Biotechnology* 25(11):1233-1234, (Nov. 2007).
Murshudov et al. "Refinement of Macromolecular Structures by the Maximum-Likelihood Method," *Acta Crystallogr. D Biol. Crystallogr.* D53:240-255, (1997).
Nagy et al., "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," *Proc. Nat'l. Acad. Sci. USA* 97(2):829-834, (Jan. 18, 2000).
Neuberger. "Expression and Regulation of Immunoglobulin Heavy Chain Gene Transfected into Lymphoid Cells," *The EMBO Journal* 2(8):1373-1378, (1983).
Nguyen et al. "Camel Heavy-chain Antibodies: Diverse Germline $V_H$H and Specific Mechanisms Enlarge the Antigen-binding Repertoire," *The EMBO Journal* 19(5):921-930, (2000).
Ni. "Research Progress and Future Perspectives in Antibodomics and Antibodomic Drugs," *Xiandai Mianyixue* 26(4):265-268, (2006), (with English Translation).
Nikula et al. "A Rapid, Single Vessel Method for Preparation of Clinical Grade Ligand Conjugated Monoclonal Antibodies," *Nucl. Med. Biol.* 22(3):387-390, (1995).
Nikula et al. "Alpha-Emitting Bismuth Cyclohexylbenzyl DTPA Constructs of Recombinant Humanized Anti-CD33 Antibodies: Pharmacokinetics, Bioactivity, Toxicity and Chemistry," *The Journal of Nuclear Medicine* 40(1):166-176, (Jan. 1999).
Nygaard et al. "The PP-Fold Solution Structure of Human Polypeptide YY and Human PYY3-36 as Determined by NMR," *Biochemistry* 45(27):8350-8357, (Jun. 16, 2006).
Ohno et al. "Antigen-binding Specificities of Antibodies are Primarily Determined by Seven Residues of $V_H$," *Proc. Natl. Acad. Sci. USA* 82(9):2945-2949, (May 1985).

Okazaki et al. "Fucose Depletion from Human IgG1 Oligosaccharide Enhances Binding Enthalpy and Association Rate Between IgG1 and Fcγ RIIIa," *J. Mol. Biol.* 336:1239-1249, (2004).
Osbourn et al. "From Rodent Reagents to Human Therapeutics Using Antibody Guided Selection," *Methods* 36:61-68, (2005).
O'Sullivan et al. "Methods for the Preparation of Enzyme—Antibody Conjugates for use in Enzyme Immunoassay," in Chapter 9 of *Methods in Enzymology* ed. by J. Langone & IT Van Vunakis, Academic Press, New York, 73:147-166, (1981).
Pace et al. "How to Measure and Predict the Molar Absorption Coefficient of a Protein," *Protein Science* 4:2411-2423, (1995).
Padlan et al. "A Possible Procedure for Reducing the Immunogenicity of Antibody Variable Domains While Preserving their Ligand-Binding Properties," *Molecular Immunology* 28(4/5):489-498, (1991).
Pai et al. "Anti-tumor Activities of Immunotoxins Made of Monoclonal Antibody B3 and Various Forms of Pseudomonas Exotoxin," *Proc. Nat'l. Acad. Sci., USA* 88(8):3358-3362, (Apr. 15, 1991).
Pastan et al. "Immunotoxins with Decreased Immunogenicity and Improved Activity," *Leukemia & Lymphoma* 52(Supp. 2):87-90, (Jun. 2011; e-published on Apr. 19, 2011).
Paul. "Structures and Function of Immunoglobulins," in Chapter 9 of *Fundamental Immunology*, 3rd Edition, Raven Press Ltd., New York, pp. 292-295, (1993).
Petkova et al. "Enhanced Half-Life of Genetically Engineered Human IgG1 Antibodies in a Humanized FcRn Mouse Model: Potential Application in Humorally Mediated Autoimmune Disease," *International Immunology* 18(12):1759-1769, (Oct. 31, 2006).
Picard. "A Lymphocyte-specific Enhancer in the Mouse Immunoglobulin κ Gene," *Nature* 307:80-82, (Jan. 5, 1984).
Plückthun. "Antibodies From *Escherichia coli*," Chapter 11 in *The Pharmacology of Monoclonal Antibodies*, Rosenburg, M. (ed.) et al., Springer-Verlag, New York, 113:269-315, (1994).
Polya. *Biochemical Targets of Plant Bioactive Compounds*, Taylor & Francis Inc., 29 West 35th Street, New York, NY 10001, pp. 847, (2003), 3 pages.
Portolano et al. "Lack of Promiscuity in Autoantigen-Specific H and L Chain Combinations as Revealed by Human H and L Chain 'Roulette'," *The Journal of Immunology* 150(3):880-887, (Feb. 1, 1993).
Presta et al. "Humanization of an Antibody Directed Against IgE," *The Journal of Immunology* 151(5):2623-2632, (Sep. 1, 1993).
Presta et al. "Humanization of an Anti-Vascular Endothelial Growth Factor Monoclonal Antibody for the Therapy of Solid Tumors and Other Disorders," *Cancer Research* 57:4593-4599, (Oct. 15, 1997).
Queen et al. "A Humanized Antibody that Binds to the Interleukin 2 Receptor," *PNAS* 86:10029-10033, (Dec. 1989).
Ravetch et al. "Fc Receptors," *Annu. Rev. Immunol.* 9:457-492, (1991).
Reiter et al. "Engineering Antibody Fv Fragments for Cancer Detection and Therapy: Disulfide-Stabilized Fv Fragments," *Nature Biotechnology* 14:1239-1245, (Oct. 1996).
Ridgway et al. "'Knobs-Into-Holes' Engineering of Antibody $C_H3$ Domains for Heavy Chain Heterodimerization," *Protein Engineering* 9(7):617-621, (1996).
Riechmann et al. "Reshaping Human Antibodies for Therapy," *Nature* 332:323-329, (Mar. 24, 1988).
Riemer et al. "Matching of Trastuzumab (Herceptin®) Epitope Mimics onto the Surface of Her-2/neu—A New Method of Epitope Definition," *Molecular Immunology* 42:1121-1124, (2005).
Ripka et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).
Roitt et al. "Molecules which Recognize Antigen," in *Immunology*, Gower Medical Publishing, New York, pp. 5.8-5.9, (1989), four pages.
Roitt et al. "Enzymic Cleavage of Human IgG1," *Immunology*, Moscow, "Mir" pp. 110-111, (2000), (with English Translation).
Roselli et al. "In Vivo Comparison of CHX-DTPA Ligand Isomers in Athymic Mice Bearing Carcinoma Xenografts," *Cancer Biotherapy & Radiopharmaceuticals* 14(3):209-220, (1999).
Rosok et al. "A Combinatorial Library Strategy for the Rapid Humanization of Anticarcinoma BR96 Fab" *The Journal of Biological Chemistry* 271(37):22611-22618, (Sep. 13, 1996).

(56) References Cited

OTHER PUBLICATIONS

Rudikoff et al. "Single Amino Acid Substitution Altering Antigen-Binding Specificity," *Proc. Natl. Acad. Sci. USA* 79:1979-1983, (Mar. 1982).
Ruegg et al. "Improved in Vivo Stability and Tumor Targeting of Bismuth-Labeled Antibody," *Cancer Research* 50:4221-4226, (Jul. 15, 1990).
Schröder et al. "Formation of Peptide Bond," in *The Peptides: Methods of Peptide Synthesis*, Academic Press Inc., 111 Fifth Avenue, New York, New York 10003, 1:76-136, (1965).
Shen et al. "Single Variable Domain Antibody as a Versatile Building Block for the Construction of IgG-like Bispecific Antibodies," *Journal of Immunological Methods* 318:65-74, (2007, e-pub. Oct. 26, 2006).
Shields et al. "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604, (Mar. 2, 2001).
Sidhu et al. "Phage-displayed Antibody Libraries of Synthetic Heavy Chain Complementarity Determining Regions," *J. Mol. Biol.* 338:299-310, (2004).
Sims et al. "A Humanized CD18 Antibody Can Block Function Without Cell Destruction," *The Journal of Immunology* 151(4):2296-2308, (Aug. 15, 1993).
Singh et al. "Labeling of Antibodies by in Situ Modification of Thiol Groups Generated From Selenol-Catalyzed Reduction of Native Disulfide Bonds," *Analytical Biochemistry* 304(2)147-156, (May 15, 2002).
Stancovski et al. "Mechanistic Aspects of the Opposing Effects of Monoclonal Antibodies to the ERBB2 Receptor on Tumor Growth," *Proceedings of the National Academy of Science USA* 88:8691-8695, (Oct. 1991).
Stella et al. "Prodrugs: A Chemical Approach to Targeted Drug Delivery," in *Directed Drug Delivery*, Borchardt et al. (eds.), pp. 247-267, Humana Press, (1985).
Tinianow et al. "Site-specifically $^{89}$Zr-labeled Monoclonal Antibodies for ImmunoPET," *Nuclear Medicine and Biology* 37(3):289-297, (2010).
Torgov et al. "Generation of an Intensely Potent Anthracycline by a Monoclonal Antibody-β-Galactosidase Conjugate," *Bioconjugate Chem.* 16:717-721, (2005; e-published on Apr. 27, 2005).
Traunecker et al. "Bispecific Single Chain Molecules (Janusins) Target Cytotoxic Lymphocytes on HIV Infected Cells," *The EMBO Journal* 10(12):3655-3659, (1991).
Tutt et al. "Trispecific F(ab')$_3$ Derivatives That Use Cooperative Signaling via the TCR/CD3 Complex and CD2 to Activate and Redirect Resting Cytotoxic T Cells," *The Journal of Immunology* 147(1):60-69, (Jul. 1, 1991).
Urlaub et al. "Isolation of Chinese Hamster Cell Mutants Deficient in Dihydrofolate Reductase Activity," *Proc. Nat'l. Acad. Sci. USA* 77(7):4216-4220, (Jul. 1980).
Van Dijk. "Human Antibodies as Next Generation Therapeutics," *Curr. Opin. Pharmacol.* 5:368-374, (2001).
Verel et al. "Quantitative $^{89}$Zr Immuno-PET for in Vivo Scouting of $^{90}$Y-Labeled Monoclonal Antibodies in Xenograft-bearing Nude Mice," *The Journal of Nuclear Medicine* 44(10):1663-1670, (Oct. 2003).
Vincent et al. "A Comparison of the Binding of Biotin and Biotinylated Macromolecular Ligands to an Anti-Biotin Monoclonal Antibody and to Streptavidin," *Journal of Immunological Methods* 165:177-182, (1993).
Vitetta et al., "Redesigning Nature's Poisons to Create Anti-tumor Reagents," *Science* 238:1098-1104, (Nov. 20, 1987).
Vollmers et al. "Death by Stress: Natural IgM-induced Apoptosis," *Methods and Findings in Experimental and Clinical Pharmacology* 27(3):185-191, (2005).
Vollmers et al. "The "Early Birds": Natural IgM Antibodies and Immune Surveillance," *Histology and Histopathology* 20:927-937, (2005).
Wark et al. "Latest Technologies for the Enhancement of Antibody Affinity," *Advanced Drug Delivery Reviews* 58:657-670, (2006; e-published on May 22, 2006).
Weldon et al. "A Guide to Taming a Toxin—Recombinant Immunotoxins Constructed From Pseudomonas Exotoxin A for the Treatment of Cancer," *FEBS Journal* 278(23):4683-4700, (Dec. 2011; e-published on Jun. 2, 2011), 27 pages.
Wiedemann et al. "Molecular and Structural Analysis of a Continuous Birch Profilin Epitope Defined by a Monoclonal Antibody," *The Journal of Biological Chemistry* 271(47):29915-29921, (Nov. 22, 1996).
Wilman. "Prodrugs in Cancer Chemotherapy" *Biochemical Society Transactions*, 615th Meeting, Belfast, 14:375-382, (1986).
Winter et al. "Making Antibodies by Phage Display Technology," *Ann. Rev. Immunol.* 12:433-455, (1994).
Wright et al. "Effect of Glycosylation on Antibody Function: Implications for Genetic Engineering," *TIBTECH* 15:26-32, (Jan. 1997).
Written Opinion of the International Searching Authority dated Apr. 22, 2015 for International Application No. PCT/EP2014/079354, filed on Dec. 29, 2014, four pages.
Written Opinion of the International Searching Authority dated Aug. 20, 2013, for PCT Patent Application No. PCT/EP2013/064090, filed on Jul. 4, 2013, three pages.
Written Opinion of the International Searching Authority dated Mar. 11, 2015 for International Application No. PCT/EP2014/079352 filed on Dec. 29, 2014, six pages.
Written Opinion of the International Searching Authority dated Nov. 19, 2013, for International Application No. PCT/EP2013/064100, filed on Jul. 4, 2013, seven pages.
Wu et al. "Humanization of a Murine Monoclonal Antibody by Simultaneous Optimization of Framework and CDR Residues," *J. Mol. Biol.* 294:151-162, (1999).
Wu et al. "Arming Antibodies: Prospects and Challenges for Immunoconjugates," *Nature Biotechnology* 23(9):1137-1146, (Sep. 2005, e-pub. Sep. 7, 2005).
Wu et al. "Simultaneous Targeting of Multiple Disease Mediators by a Dual-Variable-Domain Immunoglobulin," *Nature Biotechnology* 25(11):1290-1297, (Nov. 2007; e-published on Oct. 14, 2007).
Wu. "Simultaneous Humanization and Affinity Optimization of Monoclonal Antibodies," Chapter 12 in *Methods in Molecular Biology*, Welschol, M. (ed.) et al., Humana Press Inc., Totowa, NJ, 207:197-212, (2003).
Yamane-Ohnuki et al. "Establishment of FUT8 Knockout Chinese Hamster Ovary Cells: An Ideal Host Cell Line for Producing Completely Defucosylated Antibodies with Enhanced Antibody-dependent Cellular Cytotoxicity," *Biotech. Bioeng.* 87:614-622, (2004, e-published on Aug. 6, 2004).
Yazaki et al. "Expression of Recombinant Antibodies in Mammalian Cell Lines," Chapter 15 in *Methods in Molecular Biology*, LO, B.K.C. (ed.), Humana Press, Totowa, NJ, 248:255-268, (2004).
Yu et al. "Interaction Between Bevacizumab and Murine VEGF-A: A Reassessment," *Investigative Opthalmology & Visual Science* 49(2):522-527, (Feb. 2008).
Zahnd et al. "Directed in Vitro Evolution and Crystallographic Analysis of a Peptide-Binding Single Chain Antibody Fragment (scFv) with Low Picomolar Affinity," *Journal of Biological Chemistry* 279(18):18870-18877, (Apr. 30, 2004, e-published on Jan. 30, 2004).
Zola. "Using Monoclonal Antibodies: Soluble Antigens," Chapter 6 in *Monoclonal Antibodies: A Manual of Techniques*, CRC Press, Inc., pp. 147-158, (1987).
Bowie et al. "Deciphering the Message in Protein Sequences: Tolerance to Amino Acid Substitutions," *Science* 247(4948):1306-1310, (Mar. 16, 1990).
Brown et al. "Tolerance to Single, but Not Multiple, Amino Acid Replacements in Antibody V$_H$ CDR2: A Means of Minimizing B Cell Wastage from Somatic Hypermutation," *J. Immunol.* 156(9):3285-3291, (May 1, 1996).
Burgess et al. "Possible Dissociation of the Heparin-Binding and Mitogenic Activities of Heparin-Binding (Acidic Fibroblast) Growth

(56) References Cited

OTHER PUBLICATIONS

Factor-1 From Its Receptor-Binding Activities by Site-Directed Mutagenesis of a Single Lysine Residue," *Journal of Cell Biology* 111:2129-2138, (Nov. 1990).

Caldas et al. "Humanization of the Anti-CD-18 Antibody 6.7: An Unexpected Effect of a Framework Residue in Binding to Antigen," *Mol. Immunol.* 39(15):941-952, (May 2003).

Chang et al. "Loop-Sequence Features and Stability Determines in Antibody Variable Domains by High-Throughput Experiments," *Structure* 22(1):9-21, (Jan. 7, 2014).

Chen et al. "Generation and Analysis of Random Point Mutations in an Antibody CDR2 Sequence: Many Mutated Antibodies Lose Their Ability to Bind Antigen," *J. Exp. Med.* 176(3):855-866, (Sep. 1, 1992).

Chien et al. "Significant Structural and Functional Change of an Antigen-Binding Site by a Distant Amino Acid Substitution: Proposal of a Structural Mechanism," *Proc. Natl. Acad. Sci. USA* 86(14):5532-5536, (Jul. 1989).

Dengl et al. "Engineered Hapten-Binding Antibody Derivatives for Modulation of Pharmacokinetic Properties of Small Molecules and Targeted Payload Delivery," *Immunol. Rev.* 270(1):165-177, (Mar. 2016).

De Pascalis et al. "Grafting of 'Abbreviated' Complementarity-Determining Regions Containing Specificity-Determining Residues Essential for Ligand Contact to Engineer a Less Immunogenic Humanized Monoclonal Antibody," *J. Immunol.* 169(6):3076-3084, (2002).

Giusti et al. "Somatic Diversification of S107 From an Antiphosphocholine to an Anti-DNA Autoantibody Is Due to a Single Base Change in Its Heavy Chain Variable Region," *Proc. Natl. Acad. Sci. USA* 84(9):2926-2930, (May 1987).

Glockshuber et al. "Mapping and Modification of an Antibody Hapten Binding Site: A Site-Directed Mutagenesis Study of McPC603," *Biochemistry* 30(12):3049-3054, (Mar. 26, 1991).

Guo et al. "Protein Tolerance to Random Amino Acid Change," *Proc. Natl. Acad. Sci. USA* 101(25):9205-9210, (Jun. 22, 2004).

Jorgensen et al. "The Antibody Site in Atlantic Salmon: Phage Display and Modeling of scFv With Anti-Hapten Binding Ability," *Dev. Comp. Immunol.* 26(2):201-206, (Mar. 2006).

Klimpel et al. "Anthrax Toxin Lethal Factor Contains a Zinc Metalloprotease Consensus Sequence Which Is Required for Lethal Toxin Activity," *Mol. Microbiol.* 13(6):1093-1100, (Sep. 1994).

Lazar et al. "Transforming Growth Factor α: Mutation of Aspartic Acid 47 and Leucine 48 Results in Different Biological Activities," *Molecular and Cellular Biology* 8(3):1247-1252, (Mar. 1998).

Luque et al. "A Highly Conserved Arginine Is Critical for the Functional Folding of Inhibitor of Apoptosis (IAP) BIR Domains," *Biochemistry* 41(46):13663-13671, (Nov. 19, 2002, e-pub. Oct. 24, 2002).

Mariuzza et al. "The Structural Basis of Antigen-Antibody Recognition," *Annu. Rev. Biophys. Biophys. Chem.* 16:139-159, (1987).

Panke et al. "Quantification of Cell Surface Proteins With Bispecific Antibodies," *Protein. Eng. Des. Sel.* 26(10):645-654, (Oct. 2013, e-pub. Aug. 19, 2013).

Qin et al. "Structure-Function Analysis of the Human Insulin-Like Growth Factor Binding Protein-4," *J. Biol. Chem.* 273(36):23509-23516, (Sep. 4, 1998).

Schildbach et al. "Modulation of Antibody Affinity by a Non-Contact Residue," *Protein Sci.* 2(2):206-214, (Feb. 1993).

Solem et al. "The Primary Structure and Specificity Determining Residues Displayed by Recombinant Salomon Antibody Domains," *Mol. Immunol.* 40(18):1347-1360, (Apr. 2004).

Takada et al. "Alteration of a Single Amino Acid in Peroxisome Proliferator-Active Receptor-α (PPARα) Generates a PPARδ Phenotype," *Mol. Endocrinol.* 14(5):733-740, (2000).

Vajdos et al. "Comprehensive Functional Maps of the Antigen-Binding Site of an Anti-ErbB2 Antibody Obtained With Shotgun Scanning Mutagenesis," *J. Mol. Biol.* 320(2):415-428, (Jul. 5, 2002).

Vucic et al. "A Mutational Analysis of the Baculovirus Inhibitor of Apoptosis Op-IAP*," *J. Biol. Chem.* 273(51):33915-33921, (Dec. 18, 1998).

Winkler et al. "Changing the Antigen Binding Specificity by Single Point Mutations of an Anti-p24 (HIV-1) Antibody," *J. Immunol.* 165(8):4505-4514, (Oct. 15, 2000).

Yu et al. "Rationalization and Design of the Complementarity Determining Region Sequences in an Antibody-Antigen Recognition Interface," *PloS One* 7(3):e33340, pp. 1-15, (Mar. 22, 2012).

Barnes, P.J. "Theophylline," *Pharmaceuticals* 3(3):725-747, (Mar. 18, 2010).

Collignon, A. "High Affinity Monoclonal Anti-Digoxigenin Antibody Analysis of Specific Binding Properties," *Monoclonal Antibody Newsletter No. 4119891231*, 4:56-61 (Dec. 31, 1989), with English Abstract.

Dolbeare, F. et al. "Flow Cyometric Measurement of Total DNA Content and Incorporated Bromodeoxyuridine," *Proceedings of the National Academy of Sciences* 80(18):5573-5577, (Sep. 1983).

Edwards, B.M. et al. "The Remarkable Flexibility of the Human Antibody Repertorie; Isolation of Over One Thousand Different Antibodies to a Single Protein, Blys," *J. Mol. Biol.* 334(1):103-118 (Nov. 14, 2003).

Hermanson, G.T. *Bioconjugate Techniques, 2nd Ed.* p. 67 and p. 507, (2008).

Kabat, E.A. et al. *Sequences of Proteins of Immunological Interest, 5th ed.*, Public Health Service, National Institutes of Health, Bethesda, MD, 1:310 (1991).

Li, X. et al. "Application of Biotin, Digoxigenin or Fluorescein Conjugated Deoxynucleotides to Label DNA Strand Breaks for Analysis of Cell Proliferation and Apoptosis Using Flow Cytometry," *Biotech. Histochem.* 70(5):234-242, (1995).

Lloyd, C. et al. "Modelling the Human Immune Response: Performance of a $10^{11}$ Human Antibody Repertorie Against a Broad Panel of Therapeutically Relevant Antigens," *Protein Engineering, Design & Selection* 22(3):159-168 (2009, e-pub. Oct. 29, 2008).

Polya, G. *Biochemical Targets of Plant Bioactive Compounds: A Pharmacological Reference Guide to Sites of Action and Biological Effects CRC Press* pp. 42 & 160, (2003).

Sun, W.-C. et al. "Synthesis of Fluorinated Fluoresceins," *The Journal of Organic Chemistry* 62(19):6469-6475, (1997).

Ulbrich K. et al. "Transferrin-and Transferrin-Receptor-Antibody-Modified Nanoparticles Enable Drug Delivery Across the Blood-Brain Barrier (BBB)," *European Journal of Pharmaceutics and Biopharmaceutics* 71(2):251-256, (Feb. 2009, e-pub. Sep. 5, 2008).

Yarilin, A.A. "3: Molecular and Cellular Bases of Adaptive Immunity," in *Fundamentals of Immunology* M:Medicine pp. 169-174, (1999), with English Translation.

Yasui, H. et al. "Class Switch From μ to ó Is Mediated by Homologous Recombination Between σ μ and Σ μ Sequences in Human Immunoglobulin Gene Loci.," *Eur. J. Immunol.* 19:1399-1403, (1989).

Yu, Y.J. et al. "Boosting Brain Uptake of a Therapeutic Antibody by Reducing its Affinity for a Transcytosis Target," *Science Translational Medicine* 3(84):84ra44-84ra44, (May 25, 2011), 10 pages.

Zhang, Y. et al. "Blood-Brain Barrier Targeting of BDNF Improves Motor Function in Rats With Middle Cerebal Artery Occlusion," *Brain Research* 1111(1):227-229, (Sep. 2006, e-pub. Aug. 1, 2006).

Gratzner, H.G. "Monoclonal Antibody to 5-Bromo-and 5-Iododeoxyuridine: A New Reagent for Detections of DNA Replication," *Science* 218(4571):474-475, (Oct. 29, 1982).

Magaud, J.-P. et al. "Double Immunocytochemical Labeling of Cell and Tissue Samples With Monoclonal Anti-Bromodeozyuridine," *The Journal of Histochemistry and Cytochemistry* 37(10)1517-1527, (1989).

* cited by examiner

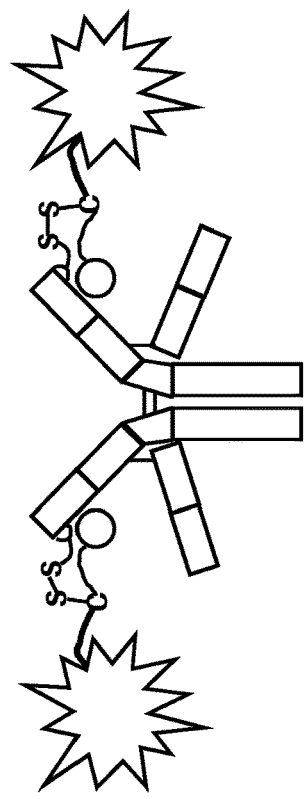
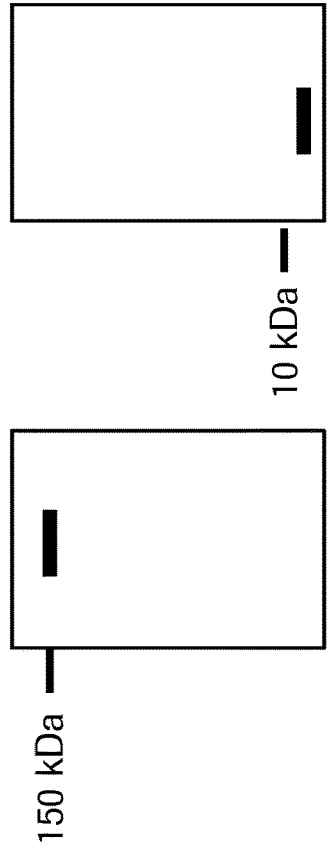
Figure 2B
non-reducing SDS-PAGE conditions — 150 kDa
reducing SDS-PAGE conditions — 10 kDa
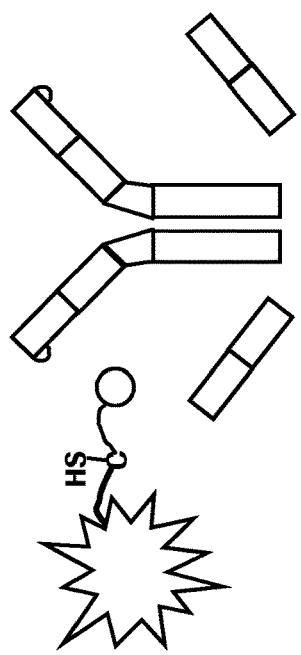
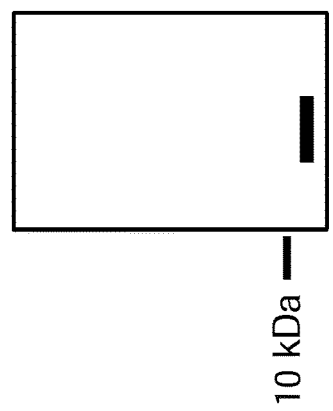
Figure 2A
reducing and non-reducing SDS-PAGE conditions — 10 kDa

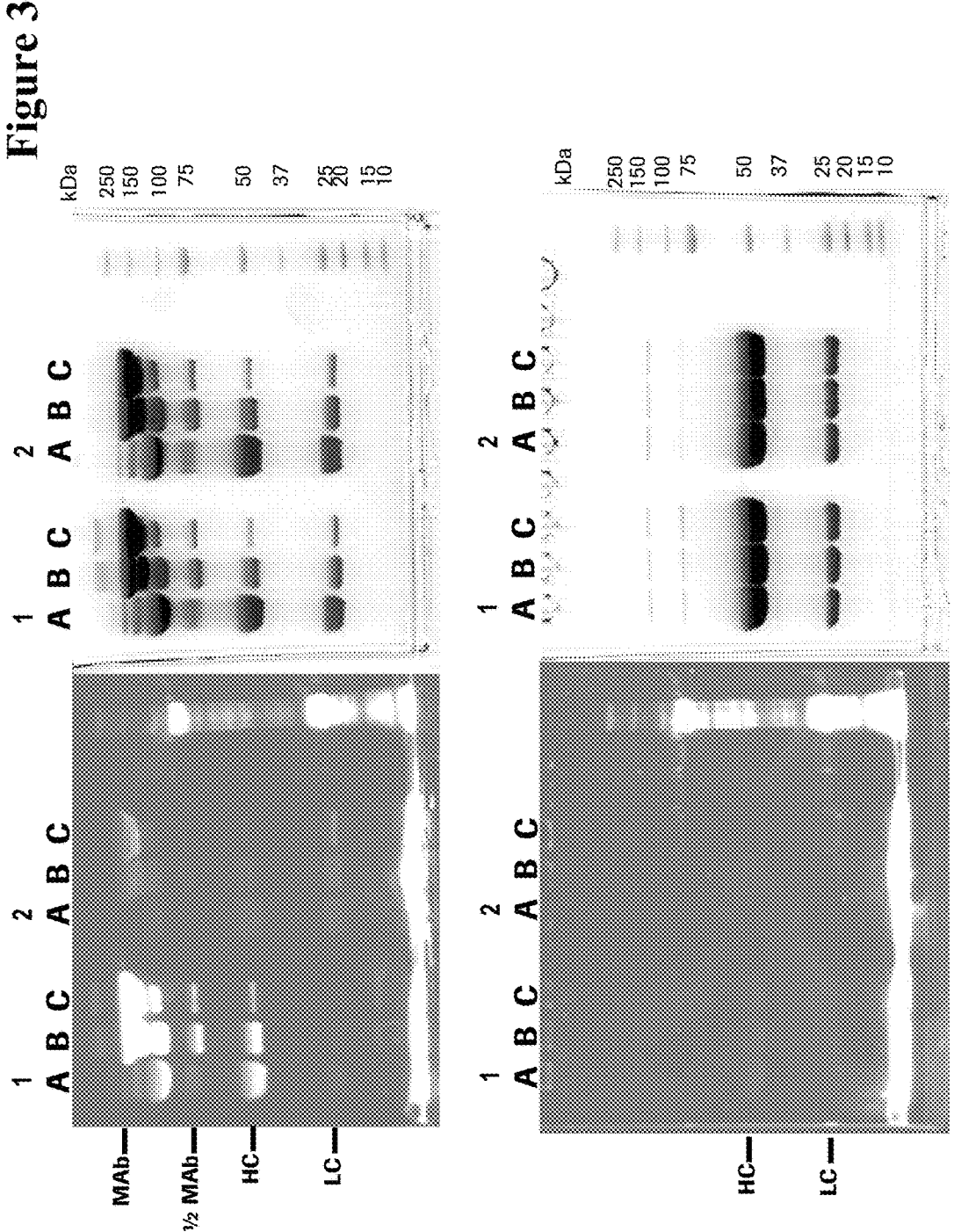

Figure 14 ant-helicar antibody the complex structure with the

SEQUENCE LISTING

```
<160> NUMBER OF SEQ ID NOS: 28

<210> SEQ ID NO 1
<211> LENGTH: 12
<212> TYPE: PRT
<213> ORGANISM: Saccharomyces cerevisiae

<400> SEQUENCE: 1

Ala His Leu Glu Asn Glu Val Ala Arg Leu Lys Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: helicar motif variant 1

<400> SEQUENCE: 2

Ala His Leu Glu Asn Glu Val Ala Arg Cys Lys Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: helicar motif variant 2

<400> SEQUENCE: 3

Ala His Leu Glu Asn Glu Val Ala Arg Leu Cys Lys
1               5                   10

<210> SEQ ID NO 4
<211> LENGTH: 109
<212> TYPE: PRT
<213> ORGANISM: Artificial Sequence
<220> FEATURE:
<223> OTHER INFORMATION: anti-helicar antibody VH

<400> SEQUENCE: 4

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Phe Thr Gly
        35                  40                  45

Leu Ile Gly Gly Thr Asn Asn Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 5
```

<211> LENGTH: 109
<212> TYPE: PRT
<213> ORGANISM: Artificial Sequence
<220> FEATURE:
<223> OTHER INFORMATION: anti-helicar antibody VL

<400> SEQUENCE: 5

```
Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 6
<211> LENGTH: 109
<212> TYPE: PRT
<213> ORGANISM: Artificial Sequence
<220> FEATURE:
<223> OTHER INFORMATION: anti-helicar antibody VL55C

<400> SEQUENCE: 6

```
Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Cys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 7
<211> LENGTH: 109
<212> TYPE: PRT
<213> ORGANISM: Artificial Sequence
<220> FEATURE:
<223> OTHER INFORMATION: anti-helicar antibody VL51C

<400> SEQUENCE: 7

```
Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45
```

```
Leu Ile Cys Gly Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu
                100                 105

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 9
<211> LENGTH: 330
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 10
<211> LENGTH: 330
<212> TYPE: PRT
```

<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 327
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110
```

```
Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 327
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
```

145                 150                 155                 160
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
            195                 200                 205

Gly Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 107
<212> TYPE: PRT
<213> ORGANISM: Homo sapiens

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 106
<212> TYPE: PRT
<213> ORGANISM: Homo sapiens

<400> SEQUENCE: 16

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro

```
                35                  40                  45
Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 17
<211> LENGTH: 219
<212> TYPE: PRT
<213> ORGANISM: Artificial Sequence
<220> FEATURE:
<223> OTHER INFORMATION: anti-LeY antibody kappa light chain

<400> SEQUENCE: 17

Asp Val Leu Met Thr Gln Ser Pro Leu Ser Leu Pro Val Ser Leu Gly
 1               5                  10                  15

Asp Gln Ala Ser Ile Ser Cys Arg Ser Ser Gln Ile Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 18
<211> LENGTH: 706
<212> TYPE: PRT
<213> ORGANISM: Artificial Sequence
<220> FEATURE:
<223> OTHER INFORMATION: anti-LeY antibody heavy
      chain_ds44-100scFvDig-Cys53

<400> SEQUENCE: 18

Asp Val Lys Leu Val Glu Ser Gly Gly Gly Leu Val Gln Pro Gly Gly
 1               5                  10                  15
```

```
Ser Leu Lys Leu Ser Cys Ala Thr Ser Gly Phe Thr Phe Ser Asp Tyr
             20                  25                  30
Tyr Met Tyr Trp Val Arg Gln Thr Pro Glu Lys Arg Leu Glu Trp Val
         35                  40                  45
Ala Tyr Ile Ser Asn Asp Asp Ser Ser Ala Ala Tyr Ser Asp Thr Val
     50                  55                  60
Lys Gly Arg Phe Thr Ile Ser Arg Asp Asn Ala Arg Asn Thr Leu Tyr
 65                  70                  75                  80
Leu Gln Met Ser Arg Leu Lys Ser Glu Asp Thr Ala Ile Tyr Tyr Cys
                 85                  90                  95
Ala Arg Gly Leu Ala Trp Gly Ala Trp Phe Ala Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
                435                 440                 445

Lys Gly Gly Gly Gly Ser Gly Gly Gly Ser Gln Val Gln Leu Val
450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Asp Tyr Ala Met Ser Trp Ile
                485                 490                 495

Arg Gln Ala Pro Gly Lys Cys Leu Glu Trp Val Ser Ser Ile Asn Ile
                500                 505                 510

Cys Ala Thr Tyr Ile Tyr Tyr Ala Asp Ser Val Lys Gly Arg Phe Thr
                515                 520                 525

Ile Ser Arg Asp Asn Ala Lys Asn Ser Leu Tyr Leu Gln Met Asn Ser
            530                 535                 540

Leu Arg Ala Glu Asp Thr Ala Val Tyr Tyr Cys Ala Arg Pro Gly Ser
545                 550                 555                 560

Pro Tyr Glu Tyr Asp Lys Ala Tyr Tyr Ser Met Ala Tyr Trp Gly Gln
                565                 570                 575

Gly Thr Thr Val Thr Val Ser Ser Gly Gly Gly Ser Gly Gly Gly
                580                 585                 590

Gly Ser Gly Gly Gly Gly Ser Asp Ile Gln Met Thr Gln Ser Pro Ser
            595                 600                 605

Ser Leu Ser Ala Ser Val Gly Asp Arg Val Thr Ile Thr Cys Arg Ala
            610                 615                 620

Ser Gln Asp Ile Lys Asn Tyr Leu Asn Trp Tyr Gln Gln Lys Pro Gly
625                 630                 635                 640

Lys Ala Pro Lys Leu Leu Ile Tyr Tyr Ser Thr Ser Leu Leu Ser Gly
                645                 650                 655

Val Pro Ser Arg Phe Ser Gly Ser Gly Ser Gly Thr Asp Phe Thr Leu
                660                 665                 670

Thr Ile Ser Ser Leu Gln Pro Glu Asp Phe Ala Thr Tyr Tyr Cys Gln
            675                 680                 685

Gln Ser Ile Thr Leu Pro Pro Thr Phe Gly Cys Gly Thr Lys Val Glu
690                 695                 700

Ile Lys
705

<210> SEQ ID NO 19
<211> LENGTH: 120
<212> TYPE: PRT
<213> ORGANISM: Artificial Sequence
<220> FEATURE:
<223> OTHER INFORMATION: humanized anti-biotin antibody VH

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
                20                  25                  30

Phe Phe Gln Trp Val Arg Gln Ala Pro Gly Gln Gly Leu Glu Trp Met
            35                  40                  45

Gly Arg Ile Asp Pro Ala Asn Gly Phe Thr Lys Tyr Ala Gln Lys Phe
        50                  55                  60

Gln Gly Arg Val Thr Ile Thr Ala Asp Thr Ser Thr Ser Thr Ala Tyr
65                  70                  75                  80

```
Met Glu Leu Ser Ser Leu Arg Ser Glu Asp Thr Ala Val Tyr Tyr Cys
            85                  90                  95

Ala Arg Trp Asp Thr Tyr Gly Ala Ala Trp Phe Ala Tyr Trp Gly Gln
        100                 105                 110

Gly Thr Leu Val Thr Val Ser Ser
        115             120

<210> SEQ ID NO 20
<211> LENGTH: 107
<212> TYPE: PRT
<213> ORGANISM: Artificial Sequence
<220> FEATURE:
<223> OTHER INFORMATION: humanized anti-biotin antibody VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
                100                 105

<210> SEQ ID NO 21
<211> LENGTH: 120
<212> TYPE: PRT
<213> ORGANISM: Artificial Sequence
<220> FEATURE:
<223> OTHER INFORMATION: humanized anti-biotin antibody VH53C VH

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Cys Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
                100                 105                 110

Gly Thr Leu Val Thr Val Ser Ser
        115             120

<210> SEQ ID NO 22
<211> LENGTH: 107
<212> TYPE: PRT
<213> ORGANISM: Artificial Sequence
```

```
<220> FEATURE:
<223> OTHER INFORMATION: humanized anti-biotin antibody VH53C VL

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
                20                  25                  30

Leu Ser Trp Tyr Gln Gln Lys Pro Gly Lys Val Pro Lys Leu Leu Ile
            35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
                100                 105

<210> SEQ ID NO 23
<211> LENGTH: 15
<212> TYPE: PRT
<213> ORGANISM: Artificial Sequence
<220> FEATURE:
<223> OTHER INFORMATION: haptenylated polypeptide 03
<220> FEATURE:
<221> NAME/KEY: MISC_FEATURE
<222> LOCATION: (2)..(2)
<223> OTHER INFORMATION: -PEG3-Cys-4Abu-NH2
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 23

Ile Lys Xaa Arg His Tyr Leu Asn Trp Val Thr Arg Gln Xaa Tyr
1               5                   10                  15

<210> SEQ ID NO 24
<211> LENGTH: 107
<212> TYPE: PRT
<213> ORGANISM: Artificial Sequence
<220> FEATURE:
<223> OTHER INFORMATION: anti-digoxigenin scdsFv VL

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
                20                  25                  30

Leu Asn Trp Tyr Gln Gln Lys Pro Gly Lys Ala Pro Lys Leu Leu Ile
            35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95
```

Thr Phe Gly Cys Gly Thr Lys Val Glu Ile Lys
                100                 105

<210> SEQ ID NO 25
<211> LENGTH: 125
<212> TYPE: PRT
<213> ORGANISM: Artificial Sequence
<220> FEATURE:
<223> OTHER INFORMATION: anti-digoxigenin scdsFv VH

<400> SEQUENCE: 25

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Cys Leu Glu Trp Val
        35                  40                  45

Ser Ser Ile Asn Ile Cys Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 26
<211> LENGTH: 34
<212> TYPE: PRT
<213> ORGANISM: Homo sapiens
<220> FEATURE:
<221> NAME/KEY: MISC_FEATURE
<222> LOCATION: (34)..(34)
<223> OTHER INFORMATION: X=tyrosine amide

<400> SEQUENCE: 26

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Xaa

<210> SEQ ID NO 27
<211> LENGTH: 34
<212> TYPE: PRT
<213> ORGANISM: Artificial Sequence
<220> FEATURE:
<223> OTHER INFORMATION: PYY3-36 helicar
<220> FEATURE:
<221> NAME/KEY: MISC_FEATURE
<222> LOCATION: (34)..(34)
<223> OTHER INFORMATION: X=thyrosine amide

<400> SEQUENCE: 27

Ile Lys Pro Glu Ala Pro Gly Glu Asp Ala Ser Pro Glu Ala His Leu
1               5                   10                  15

Ala Asn Glu Val Ala Arg Leu His Tyr Leu Asn Leu Val Thr Arg Gln
            20                  25                  30

Arg Xaa

```
<210> SEQ ID NO 28
<211> LENGTH: 244
<212> TYPE: PRT
<213> ORGANISM: Artificial Sequence
<220> FEATURE:
<223> OTHER INFORMATION: helicar motif amino acid sequence cystein
      variant 1 fused to pseudomonas exotoxin LR8M with a GGG-peptidic
      linker and the C-terminal K deleted

<400> SEQUENCE: 28

Ala His Leu Glu Asn Glu Val Ala Arg Leu Cys Lys Gly Gly Gly Arg
1               5                   10                  15

His Arg Gln Pro Arg Gly Trp Glu Gln Leu Pro Thr Gly Ala Glu Phe
            20                  25                  30

Leu Gly Asp Gly Gly Ala Val Ser Phe Ser Thr Arg Gly Thr Gln Asn
        35                  40                  45

Trp Thr Val Glu Arg Leu Leu Gln Ala His Arg Gln Leu Glu Glu Gly
    50                  55                  60

Gly Tyr Val Phe Val Gly Tyr His Gly Thr Phe Leu Glu Ala Ala Gln
65                  70                  75                  80

Ser Ile Val Phe Gly Gly Val Arg Ala Arg Ser Gln Asp Leu Asp Ala
                85                  90                  95

Ile Trp Ala Gly Phe Tyr Ile Ala Gly Asp Pro Ala Leu Ala Tyr Gly
            100                 105                 110

Tyr Ala Gln Asp Gln Glu Pro Asp Ala Ala Gly Arg Ile Arg Asn Gly
        115                 120                 125

Ala Leu Leu Arg Val Tyr Val Pro Arg Ser Ser Leu Pro Gly Phe Tyr
    130                 135                 140

Ala Thr Ser Leu Thr Leu Ala Ala Pro Glu Ala Ala Gly Glu Val Glu
145                 150                 155                 160

Arg Leu Ile Gly His Pro Leu Pro Leu Arg Leu Asp Ala Ile Thr Gly
                165                 170                 175

Pro Glu Glu Ser Gly Gly Arg Leu Glu Thr Ile Leu Gly Trp Pro Leu
            180                 185                 190

Ala Glu Arg Thr Val Val Ile Pro Ser Ala Ile Pro Thr Asp Pro Arg
        195                 200                 205

Asn Val Gly Gly Asp Leu Asp Pro Ser Ser Ile Pro Asp Ser Glu Ala
    210                 215                 220

Ala Ile Ser Ala Leu Pro Asp Tyr Ala Ser Gln Pro Gly Lys Pro Pro
225                 230                 235                 240

Arg Glu Asp Leu
```

COVALENTLY LINKED HELICAR-ANTI-HELICAR ANTIBODY CONJUGATES AND USES THEREOF

CROSS REFERENCE TO RELATED APPLICATIONS

This application is a continuation of International Application No. PCT/EP2014/079352 having an international filing date of Dec. 29, 2014, the entire contents of which are incorporated herein by reference, and which claims benefit under 35 U.S.C. § 119 to European Patent Application No. 14150087.6 filed Jan. 3, 2014.

SEQUENCE LISTING

The instant application contains a Sequence Listing submitted via EFS-Web and hereby incorporated by reference in its entirety. Said ASCII copy, created on Jun. 21, 2016, is named P31921USSeqList.txt, and 45,693 bytes in size.

FIELD OF INVENTION

Herein are reported (covalent) complexes comprising the helicar motif amino acid sequence and an anti-helicar antibody whereby the helicar motif amino acid sequence is present in or conjugated to a payload whereby the helicar motif amino acid sequence containing element and the anti-helicar antibody are covalently linked to each other via a single bond. Also reported are methods for producing the covalent complexes and uses thereof.

BACKGROUND OF THE INVENTION

Major bottlenecks for therapeutic application of polypeptides are their limited solubility, in vivo stability, short serum half-life and fast clearance from the bloodstream.

Different approaches are reported to address these drawbacks. However, none of these technologies provides for a robust and universal platform that enables pharmacokinetic (PK) modulation without encountering immunogenicity risks or potential loss of biological activity.

One approach to improve PK/stability and biophysical behavior of therapeutic polypeptides is to fuse them to entities which stabilized the polypeptide, keep it in solution, and extend its half-life. Examples of such entities are human serum albumin or human immunoglobulin Fc-regions. This approach is applicable to many linear polypeptides that are composed of naturally occurring amino acid residues and that tolerate modifications at either their C- or N-terminus without losing their biological activity. Polypeptides that are cyclic, stapled, contain non-natural amino acid residues, or additional modifications cannot be recombinantly produced as fusion polypeptides. However, such polypeptides may be the desired choice for therapeutic applications because they are frequently superior to 'normal' linear peptides in terms of protease stability, activity and specificity.

One approach to improve PK/stability and biophysical behavior of therapeutic polypeptides, which can also be applied to those that are cyclic, stapled, or contain non-natural structures, is the chemical or enzymatic conjugation to polymers, for example by PEGylation or HESylation. However, such modifications frequently lead to significant reduction of the biological activity of the polypeptide and can under certain circumstances be the reason for safety or toxicity problems.

A major disadvantage of most existing chemical coupling technologies for stabilization or PK modulation of therapeutic polypeptides is their complexity. Beside the chemical coupling step the methods result in many cases in a mixture of polypeptide derivatives that are connected to the PK-modulating entity with uncertain stoichiometries and/or at undefined positions. Additionally currently used polypeptide modification-technologies often result in strongly reduced or even complete loss of biological activity of the therapeutic polypeptide. In addition, it is difficult to predict pharmacological properties and/or possible degradation routes of the chemical conjugates.

The helicar element is composed of a 12-mer amino acids peptide forming an α-helix. The structural elements of the peptide are described in Nygaard et al. reporting also an anti-helicar antibody and the complex structure with the 12-mer peptide, part of a yeast leucine zipper protein called GCN4. The antibody portion Fv has been affinity matured using the phage display technique to an affinity of 25 pM (Zahnd, C., et al., J. Biol. Chem. 279 (2004) 18870-18877). Metz, S., et al. (Proc. Natl. Acad. Sci. USA 108 (2011) 8194-8424) report bispecific digoxigenin-binding antibodies for targeted payload delivery. PK modulation of haptenylated peptides via non-covalent antibody complexation is reported by Hoffmann, E., et al. (J. Contr. Rel. 171 (2013) 48-56). In WO 2012/093068 a pharmaceutical composition of a complex of an anti-dig antibody and digoxigenin that is conjugated to a peptide is reported. Directed in vitro evolution and crystallographic analysis of a peptide-binding single chain antibody fragment (scFv) with low picomolar affinity is reported by Zahnd, C., et al. (J. Biol. Chem. 279 (2004) 18870-18877). Hanes, J., et al. (Proc. Natl. Acad. Sci. USA 95 (1998) 14130-14135) report that ribosome display efficiently selects and evolves high-affinity antibodies in vitro from immune libraries.

U.S. Pat. No. 5,804,371 reports hapten-labeled peptides and their use in an immunological method of detection. A digoxigenin-labeled peptide (Bradykinin) and its application to chemiluminoenzyme immunoassay of Bradykinin in inflamed tissues are reported by Decarie A., et al. (Peptides 15 (1994) 511-518).

In WO 2004/065569 multi-functional antibodies are reported.

In WO 2014/006124 covalent hapten-anti-hapten antibody complexes are reported.

SUMMARY OF THE INVENTION

It has been found that helicar-mediated complex formation can be used to covalently conjugate polypeptides comprising the helicar motif amino acid sequence either at one of the termini or within the polypeptide sequence. In case of an insertion, the 12-mer helicar motif amino acid sequence is either inserted within the sequence of the polypeptide or an existing helical motif is modified to incorporate the essential amino acids that are involved in the anti-helicar antibody recognition.

It has been found that by the covalent conjugation of a helicar motif amino acid sequence containing compound to an anti-helicar antibody stabilization, PK-property improvement of the compound or in case of a bispecific antibody an additional targeting can be achieved.

One aspect as reported herein is a conjugate comprising a helicar motif amino acid sequence containing compound and an antibody that specifically binds to the helicar motif amino acid sequence characterized by a covalent bond between the helicar motif amino acid sequence containing compound and an amino acid residue in the CDR2 of the anti-helicar antibody, whereby the CDR2 is determined according to Kabat.

It has been found that any compound can be used in the conjugates and methods as reported herein upon derivatization with a helicar motif amino acid sequence, which comprises the functional residue for the formation of the covalent bond between the helicar motif amino acid sequence containing compound and an amino acid residue in the CDR2 of the antibody. The location of the functional group in the helicar motif amino acid sequence has the advantage that it is not necessary to re-engineer the synthesis and the position of the functional group in the CDR2 of the antibody when the helicar motif-derivatized compound is changed.

One aspect as reported herein is a conjugate comprising a helicar motif amino acid sequence containing compound and an antibody that specifically binds to the helicar motif amino acid sequence of the helicar motif amino acid sequence containing compound (anti-helicar motif amino acid sequence antibody) characterized by a covalent bond between the helicar motif amino acid sequence containing compound and an amino acid residue in the CDR2 of the antibody, whereby the CDR2 is determined according to Kabat.

In one embodiment the CDR2 is the light chain CDR2.

In one embodiment the helicar motif amino acid sequence has the amino acid sequence AHLENEVARLKK (SEQ ID NO: 01) or is a variant thereof with one amino acid residue changed to cysteine. In one embodiment the helicar motif amino acid sequence has the amino acid sequence AHLENEVARLKK (SEQ ID NO: 01), wherein one amino acid residue of the three C-terminal amino acid residues is changed to cysteine. In one embodiment the helicar motif amino acid sequence has the amino acid sequence of AHLENEVARCKK (SEQ ID NO: 02) or AHLENEVARLCK (SEQ ID NO: 03).

In one embodiment the helicar motif amino acid sequence containing compound comprises a helicar motif amino acid sequence, optionally a linker, and a payload.

In one embodiment the helicar motif amino acid sequence containing compound is a polypeptide comprising the helicar motif amino acid sequence either fused to one of its termini or within the polypeptide sequence. In this embodiment the payload is a polypeptide.

One aspect as reported herein is a conjugate comprising i) a compound comprising a helicar motif amino acid sequence selected from the group comprising SEQ ID NO: 01, a variant of SEQ ID NO: 01 wherein one amino acid residue has been changed to cysteine, SEQ ID NO: 02, and SEQ ID NO: 03, and ii) an antibody that specifically binds to the helicar motif amino acid sequence, wherein the conjugate comprises a covalent bond between the helicar motif amino acid sequence and an amino acid residue in the CDR2 of the anti-helicar antibody, whereby the CDR2 is determined according to Kabat.

In one embodiment the CDR2 is the light chain CDR2.

In one embodiment the helicar motif amino acid sequence containing compound comprises a helicar motif amino acid sequence, optionally a linker, and a payload.

In one embodiment of all aspects the covalent bond is between the helicar motif amino acid sequence containing compound and an amino acid residue in the CDR2 of the antibody.

In one embodiment the covalent bond is between a functional group in the helicar motif amino acid sequence containing compound and the amino acid residue in the CDR2 of the antibody.

In one embodiment the functional group is in the helicar motif amino acid sequence.

In one embodiment the covalent bond is between a cysteine residue in the light chain CDR2 of the antibody and a functional group in the helicar motif amino acid sequence containing compound.

In one embodiment the cysteine residue in the light chain CDR2 of the antibody is at position 55 or position 51 according to the light chain variable domain numbering of Kabat.

In one embodiment the cysteine residue in the light chain CDR2 of the antibody is at position 55 according to the light chain variable domain numbering of Kabat.

In one embodiment of all aspects the covalent bond is a disulfide bond.

In one embodiment of all aspects the covalent bond is a disulfide bond between a cysteine residue in the helicar motif amino acid sequence and a cysteine residue in the CDR2 of the light chain of the anti-helicar antibody. In one embodiment the helicar motif amino acid sequence has the amino acid sequence of SEQ ID NO: 02.

In one embodiment of all aspects the antibody is a bispecific antibody comprising a first binding specificity to a non-helicar antigen and a second binding specificity to helicar motif amino acid sequence. In one embodiment the (non-helicar) antigen is a cell surface antigen. In one embodiment the cell surface antigen is a tumor associated antigen. In one embodiment one heavy chain of the bispecific antibody comprises a hole mutation and the respective other chain comprises a knob mutation. In one embodiment one heavy chain of the bispecific antibody comprises the mutations T366S, L368A and Y407V and the respective other chain comprises the mutation T366W. In one embodiment one heavy chain of the bispecific antibody further comprises the mutation S354C and the respective other chain comprises the mutation Y349C.

In one embodiment the bispecific antibody is a full length antibody to which at one or both heavy chain C-termini a scFv or a dsscFv or a scFab or a dsscFab or a combination thereof has been fused either directly or via a peptidic linker.

In one embodiment the bispecific antibody is a full length antibody. In one embodiment one heavy chain of the bispecific antibody comprises a hole mutation and the respective other chain comprises a knob mutation.

In one embodiment the payload is selected from a binding moiety, a labeling moiety, and a biologically active moiety.

In one embodiment the antibody is a full length antibody.

In one embodiment the antibody is a humanized or a human antibody.

In one embodiment the constant region of the antibody is of the IgG1 subclass or of the IgG4 subclass.

In one embodiment the antibody has a constant region of the IgG1 subclass with an alanine at position 234 and 235 and with a glycine at position 329 with numbering according to the EU index of Kabat.

In one embodiment the antibody has a constant region of the IgG4 class with a proline at position 228, a glutamic acid at position 235 and a glycine at position 329 with numbering according to the EU index of Kabat.

In one embodiment the antibody is an antibody fragment. In one embodiment the fragment is a Fab or a $(Fab)_2$.

In one embodiment of all aspects the conjugate comprises exactly one covalent bond per light chain CDR2.

In one embodiment the helicar motif amino acid sequence containing compound comprises a reactive group that can form a covalent bond with the thiol group of the cysteine residue in the CDR2 of the antibody. In one embodiment the reactive group is a thiol, or a maleimide, or a haloacetyl.

In one embodiment of all aspects the covalent bond is a disulfide bond. In one embodiment the disulfide bond is formed without the addition of a redox active agent.

In one embodiment the conjugate comprises a therapeutic or detectable moiety. In one embodiment the therapeutic or detectable moiety is covalently conjugated to helicar motif amino acid sequence or the helicar motif amino acid sequence is incorporated into the therapeutic or detectable moiety.

In one embodiment the helicar motif amino acid sequence is conjugated to a polypeptide consisting of 5 to 500 amino acid residues. In one embodiment the polypeptide comprises 10 to 450 amino acid residues. In one embodiment the polypeptide comprises 12 to 450 amino acid residues. In one embodiment the polypeptide comprises 15 to 400 amino acids residues.

In one embodiment the helicar motif amino acid sequence is conjugated to a detectable label.

In one embodiment the helicar motif amino acid sequence is conjugated to the polypeptide, or to the detectable label, or to the payload via a linker. In one embodiment the linker is a non-peptidic linker. In one embodiment the linker is a peptidic linker.

One aspect as reported herein is an anti-helicar antibody that has in the light chain a cysteine residue in the CDR2 whereby the CDRs are determined according to Kabat.

In one embodiment the cysteine residue in the light chain CDR2 of the antibody is at position 55 or position 51 according to the light chain variable domain numbering of Kabat.

In one embodiment the cysteine residue in the light chain CDR2 of the antibody is at position 55 according to the light chain variable domain numbering of Kabat.

In one embodiment the antibody has in exactly one light chain variable domain a cysteine residue at position 55 or position 51 according to the light chain variable domain numbering of Kabat.

In one embodiment of all aspects the antibody is a humanized or human antibody.

In one embodiment the antibody is a full length antibody, or a Fab, or a scFv, or a scFv conjugated to an Fc-region.

In one embodiment the cysteine forms a disulfide bond with an isolated cysteine residue or an isolated homocysteine residue.

One aspect as reported herein is an immunoconjugate comprising the conjugate as reported herein and a cytotoxic agent.

One aspect as reported herein is a pharmaceutical formulation comprising the conjugate as reported herein and a pharmaceutically acceptable carrier.

The conjugate as reported herein for use as a medicament.

The conjugate as reported herein for the treatment of cancer.

The conjugate as reported herein for the treatment of diabetes.

The conjugate as reported herein for the treatment of adiposities.

The conjugate as reported herein for the treatment of an inflammatory disease.

The conjugate as reported herein for the treatment of a metabolic disease.

The conjugate as reported herein for the treatment of a viral disease.

One aspect as reported herein is the use of a conjugate as reported herein in the manufacture of a medicament.

One aspect as reported herein is the use of a conjugate as reported herein as diagnostic agent.

One aspect as reported herein is the use of a conjugate as reported herein comprising a therapeutic polypeptide to increase the stability of the therapeutic polypeptide.

One aspect as reported herein is the use of a conjugate as reported herein comprising a therapeutic polypeptide to increase the activity of the therapeutic polypeptide.

One aspect as reported herein is the use of a conjugate as reported herein comprising a therapeutic polypeptide to increase the in vivo half-life of the therapeutic polypeptide.

One aspect as reported herein is the use of a conjugate as reported herein in the treatment of a disease.

One aspect as reported herein is a method of treating an individual having a disease comprising administering to the individual an effective amount of a conjugate as reported herein.

One aspect as reported herein is a method of treating a disease in an individual comprising administering to the individual an effective amount of the conjugate as reported herein.

In one embodiment the disease is cancer.
In one embodiment the disease is diabetes.
In one embodiment the disease is adipositas.

One aspect as reported herein is a method of producing a conjugate as reported herein comprising the combination of an anti-helicar antibody comprising a first reactive group and an helicar motif amino acid sequence containing compound comprising a second reactive group, whereby the alpha carbon atom of the amino acid residue that bears the first reactive group is about 10 to 11 Angstrom apart from the atom of the helicar motif amino acid sequence containing compound.

One aspect as reported herein is a method of producing a conjugate as reported herein comprising the steps of
  combining in solution an anti-helicar antibody, which specifically binds to a helicar motif amino acid sequence and which comprises a first reactive group at one amino acid residue in the CDR2, with a helicar motif amino acid sequence containing compound comprising a second reactive group, wherein the helicar motif amino acid sequence containing compound comprises a payload, such as a peptide consisting of 5 to 500 amino acids or a detectable label, and
  recovering of the conjugate from the solution.

One aspect as reported herein is a method for producing an anti-helicar antibody for the formation of a conjugate as reported herein, comprising the step of
  cultivating a cell comprising a nucleic acid encoding the anti-helicar antibody, and
  recovering the anti-helicar antibody from the cell or the cultivation medium,
  wherein in the anti-helicar antibody the residue in the light chain CDR2 is mutated to cysteine that has in the X-ray structure of the non-covalent complex of the anti-helicar antibody and the helicar motif amino acid sequence containing compound a distance of 10 to 11 Angstrom between the alpha-carbon atom of the amino acid residue in the antibody CDR2 and the atom of the helicar motif amino acid sequence containing compound atom between which the covalent bond is to be formed.

One aspect as reported herein is a method for identifying a position in an anti-helicar antibody CDR2 that can be mutated to cysteine for the formation of a covalent bond between the residue in the antibody CDR2 and the bound helicar motif amino acid sequence containing compound comprising the step of providing a crystal structure of the non-covalent complex of the anti-helicar antibody and the helicar motif amino acid sequence containing compound, and identifying an amino acid residue in the CDR2 of the anti-helicar antibody and in the helicar motif amino acid sequence containing compound with a distance of 10 to 11 Angstrom between the alpha-carbon atoms of the amino acid residue in the antibody CDR2 and the atom in the helicar motif amino acid sequence containing compound, wherein the identified position is the position in an antibody CDR2 that can be mutated to cysteine for the formation of a covalent bond between the residue in the antibody CDR2 and the bound helicar motif amino acid sequence containing compound.

One aspect as reported herein is a bispecific anti-helicar antibody for targeted delivery of a helicar motif amino acid sequence containing compound to a target cell, wherein the bispecific antibody comprises a first binding specificity (site) that specifically binds to the helicar motif amino acid sequence containing compound and a second binding specificity that specifically binds to a cell surface marker of the target cell.

One aspect as reported herein is the use of a complex consisting of a helicar motif amino acid sequence containing compound and an antibody that has a first binding specificity that specifically binds to a helicar motif amino acid sequence and a second binding specificity that specifically binds to a blood brain barrier receptor for delivering the helicar motif amino acid sequence containing compound to the brain.

In one embodiment the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

In one embodiment the bispecific antibody is a full length antibody comprising two binding sites.

In one embodiment the bispecific antibody is a full length antibody to which one or two scFvs or scFabs have been fused and that comprises three or four binding sites.

In one embodiment the bispecific antibody is an antibody fragment. In one embodiment the antibody fragment is selected from F(ab')2 and diabodies.

In one embodiment the bispecific antibody is a humanized or a human antibody.

In one embodiment the bispecific antibody is free of effector function. In one embodiment the bispecific antibody has no functional Fc-region. In one embodiment the bispecific antibody has no Fc-region. In one embodiment the bispecific antibody has an Fc-region of the human IgG1 subclass with the mutations L234A, L235A and P329G, wherein the positions are determined according to the Fc-region numbering of Kabat (Kabat EU index). In one embodiment the bispecific antibody has an Fc-region of the human IgG4 subclass with the mutations S228P, L235E and P329G, wherein the positions are determined according to the Fc-region numbering of Kabat (Kabat EU index).

In one embodiment the bispecific antibody comprises
   a) one binding site for the helicar motif amino acid sequence containing compound and one binding site for the blood brain barrier receptor, or
   b) two binding sites for the helicar motif amino acid sequence containing compound and one binding site for the blood brain barrier receptor, or
   c) one binding site for the helicar motif amino acid sequence containing compound and two binding sites for the blood brain barrier receptor, or
   d) two binding sites for the helicar motif amino acid sequence containing compound and two binding sites for the blood brain barrier receptor.

In cases b) and c) of the previous embodiment one heavy chain of the bispecific antibody comprises a hole mutation and the respective other chain comprises a knob mutation.

In one preferred embodiment the bispecific antibody comprises two binding sites for the helicar motif amino acid sequence containing compound and one or two binding sites for the blood brain barrier receptor.

In one embodiment the helicar motif amino acid sequence containing compound comprises between the hapten and the payload a linker. In one embodiment the linker is a peptidic linker. In one embodiment the linker is a chemical linker (non-peptidic linker).

It has been found that by the covalent coupling of a helicar motif amino acid sequence containing compound to an anti-helicar motif amino acid sequence containing compound antibody a stabilization and PK-property improvement of the compound can be achieved.

In one embodiment the bispecific antibody and the helicar motif amino acid sequence containing compound each comprise a functional group whereby upon binding of the helicar motif amino acid sequence containing compound by the bispecific antibody a covalent bond is formed between the helicar motif amino acid sequence containing compound and the bispecific antibody.

In one embodiment the bispecific antibody comprises a functional group at an amino acid residue in the CDR2 of the antibody, whereby the CDR2 is determined according to Kabat. In one embodiment the functional group at an amino acid residue in the CDR2 of the antibody is a thiol group. In one embodiment the bispecific antibody comprises a cysteine amino acid residue in the CDR2 of the antibody.

In one embodiment of all aspects the helicar motif amino acid sequence containing compound comprises a functional group in the helicar motif amino acid sequence or if present in the linker between the helicar motif amino acid sequence and the compound.

In one embodiment the functional group is a thiol, or a maleimide, or a haloacetyl. In one embodiment the functional group in the helicar motif amino acid sequence or if present in the linker is a thiol group.

In one embodiment of all aspects the covalent bond is between a cysteine residue in the CDR2 of the antibody and the thiol group in the helicar motif amino acid sequence containing compound. In one embodiment the covalent bond is a disulfide bond. In one embodiment the covalent bond is a disulfide bond and it is formed without the addition of redox active agents.

In one embodiment of all aspects the CDR2 is the light chain CDR2. In one embodiment the cysteine residue in the light chain CDR2 of the antibody is at position 51 or at position 55 according to the light chain variable domain numbering of Kabat. In one preferred embodiment the cysteine residue in the light chain CDR2 of the antibody is at position 55 according to the light chain variable domain numbering of Kabat.

It has been found that any compound can be used in the helicar motif amino acid sequence containing compound upon derivatization of the helicar amino acid sequence with a cysteine comprising the functional group for the formation of the covalent disulfide bond between the helicar motif amino acid sequence containing compound and the cysteine residue in the light chain CDR2 of the antibody. The location of the cysteine residue (thiol functional group) in the helicar motif amino acid sequence has the advantage that it is not necessary to re-engineer the synthesis and the position of the cysteine residue in the light chain CDR2 of the antibody if the payload is changed.

In one embodiment of all aspects exactly one covalent bond is formed per light chain CDR2.

In one embodiment of all aspects the compound is selected from a binding moiety, a labeling moiety, and a biologically active moiety.

In one embodiment of all aspects the biologically active moiety is selected from the group comprising antibodies, polypeptides, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), locked nucleic acids (LNAs), ribozymes, and small molecules, or active fragments of any of the foregoing.

In one embodiment of all aspects the compound is a nucleic acid or nucleic acid derivative. In one embodiment the nucleic acid is an iRNA or a LNA.

In one embodiment of all aspects the compound is a polypeptide.

In one embodiment the compound is a small molecule (non-polypeptide biologically active moiety).

In one embodiment the biologically active moiety is a polypeptide. In one embodiment the polypeptide is consisting of 5 to 500 amino acid residues. In one embodiment the polypeptide comprises 10 to 450 amino acid residues. In one embodiment the polypeptide comprises 15 to 400 amino acid residues. In one embodiment the polypeptide comprises 18 to 350 amino acids residues.

In one embodiment the bispecific antibody comprises a first binding specificity that specifically binds to a helicar motif amino acid sequence containing compound (anti-helicar motif amino acid sequence binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment the bispecific antibody has two binding specificities that specifically bind to the helicar motif amino acid sequence containing compound (two anti-helicar motif amino acid sequence binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

DESCRIPTION OF THE FIGURES

FIG. 2A-2B: Scheme of SDS-PAGE self-fluorescence band pattern (without further staining of the SDS-PAGE gel): FIG. 2A: If no covalent bond is formed between the antibody and the hapten-fluorophore conjugate both under reducing or non-reducing conditions one self-fluorescent band at the molecular weight of free hapten-fluorophore conjugate can be detected. FIG. 2B: If a covalent bond is formed between the antibody and the hapten-fluorophore conjugate under non-reducing conditions one self-fluorescent band at the combined molecular weight of the antibody and the hapten-fluorophore conjugate can be detected. Under reducing conditions the disulfide bridges in the conjugate of the antibody and the hapten-fluorophore conjugate (haptenylated compound) are cleaved and one self-fluorescent band at the molecular weight of free hapten-fluorophore conjugate can be detected.

FIG. 3: Conjugate formation of hapten-binding Cys-mutated antibodies with hapten-Cys-fluorescent label conjugates (haptenylated compound) in the presence of redox active agents: oxidation agent (glutathione disulfide, GSSG) and reducing agent (dithioerythritol, DTE): Antibody complexation and subsequent covalent linkage at defined positions is detected by fluorescence signals in SDS PAGE analyses. Non-reducing (upper images) and reducing (lower images) SDS-PAGE analyses were performed as described in Example 3. Covalently antibody linked haptens are detectable as larger sized protein bound signals at the appropriate positions under non-reduced conditions. These signals detach from protein upon reduction and are visible as small entities under reducing conditions.

Left: fluorescence image
Right: Coomassie blue staining
Series 1: anti-digoxigenin antibody with 52bC mutation
Series 2: anti-digoxigenin antibody with wild-type residue at position 52b
(A) covalent coupling with 3 mM DTE and 10 mM GSSG;
(B) covalent coupling with 0.3 mM DTE and 1 mM GSSG;
(C) covalent coupling with 0.03 mM DTE and 0.1 mM GSSG.

Figure 1:
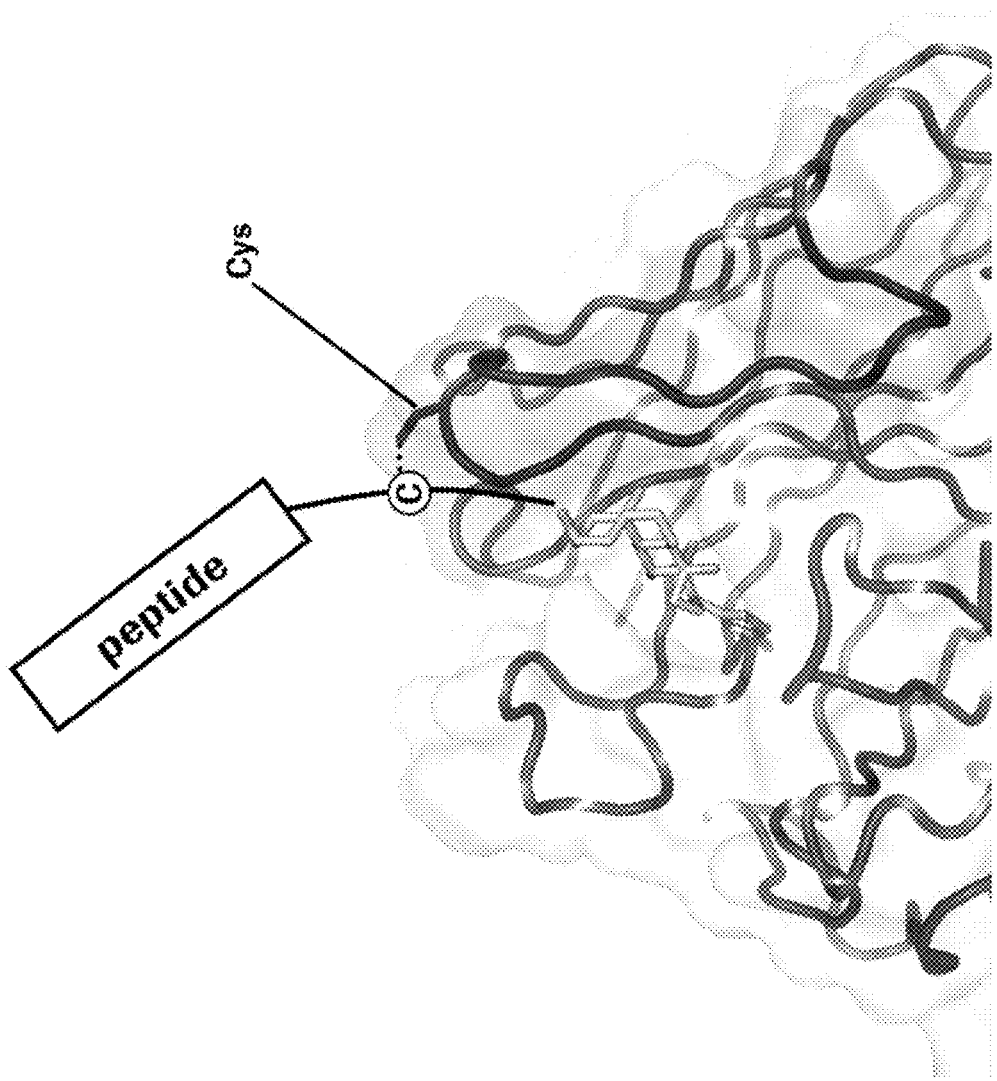
FIG. 1: Introduction of SH functionalities in the hapten as well as in the antibody at appropriate positions allow the antibody and the hapten to form a covalent bond in between resulting in a conjugate.
Figure 4:
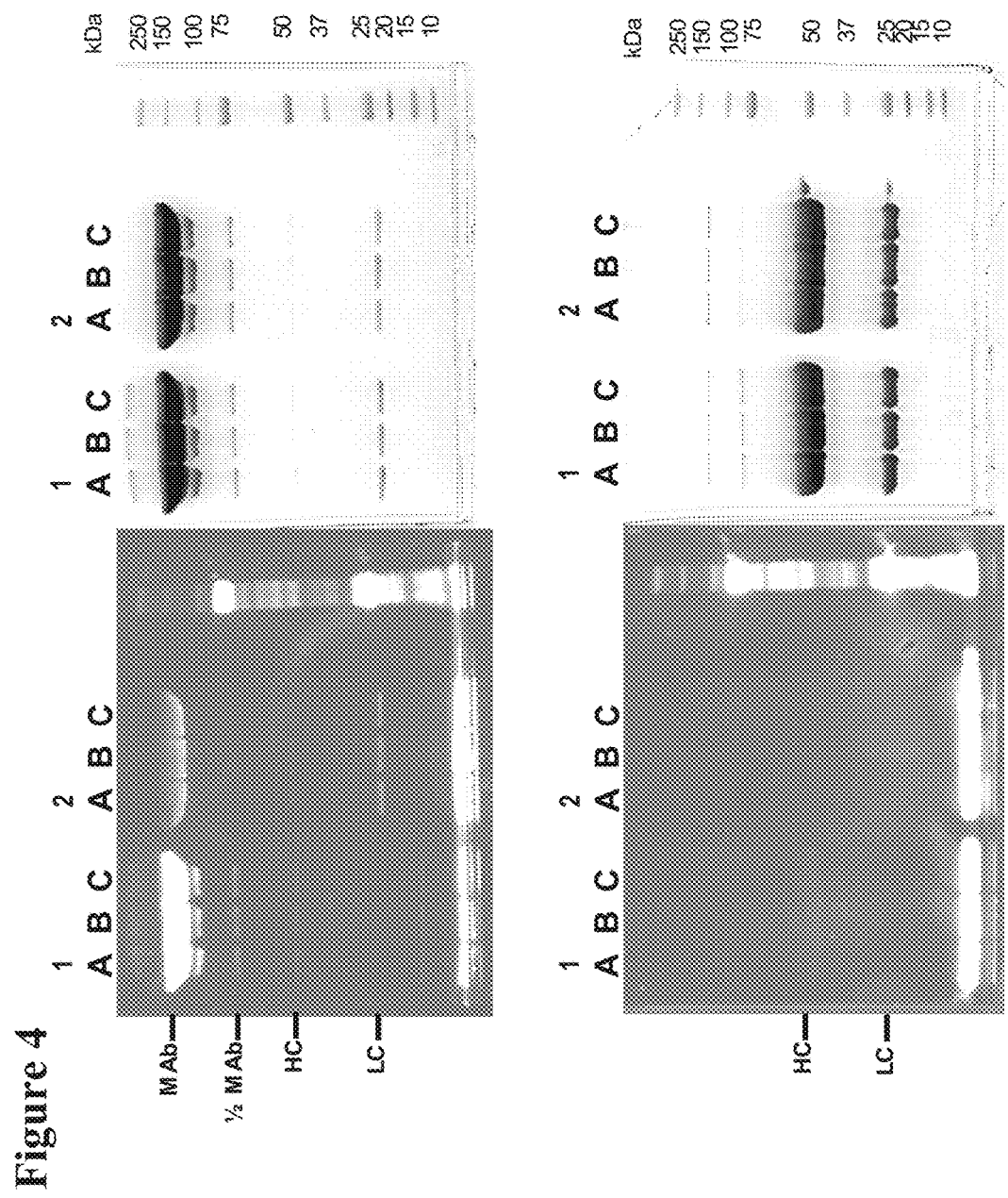

FIG. 4: Complex formation of hapten-binding Cys mutated antibodies with hapten-Cys-fluorescent label conjugates in the presence solely of an oxidation agent (glutathione disulfide, GSSG) but in the absence of reducing agents or in the absence of both: Antibody complexation and subsequent covalent linkage at defined positions is detected by fluorescence signals in SDS PAGE analyses. Non-reducing (upper images) and reducing (lower images) SDS-PAGE analyses were performed as described in Example 4. Covalently antibody linked haptens are detectable as larger sized protein bound signals at the appropriate positions under non-reduced conditions. These signals detach from protein upon reduction and are visible as small entities under reducing conditions.

Left: fluorescence image
Right: Coomassie blue staining
Series 1: anti-digoxigenin antibody with 52bC mutation
Series 2: anti-digoxigenin antibody with wild-type residue at position 52b
(A) no additives
(B) covalent coupling with 1 mM GSSG;
(C) covalent coupling with 0.1 mM GSSG.

Figure 5A:
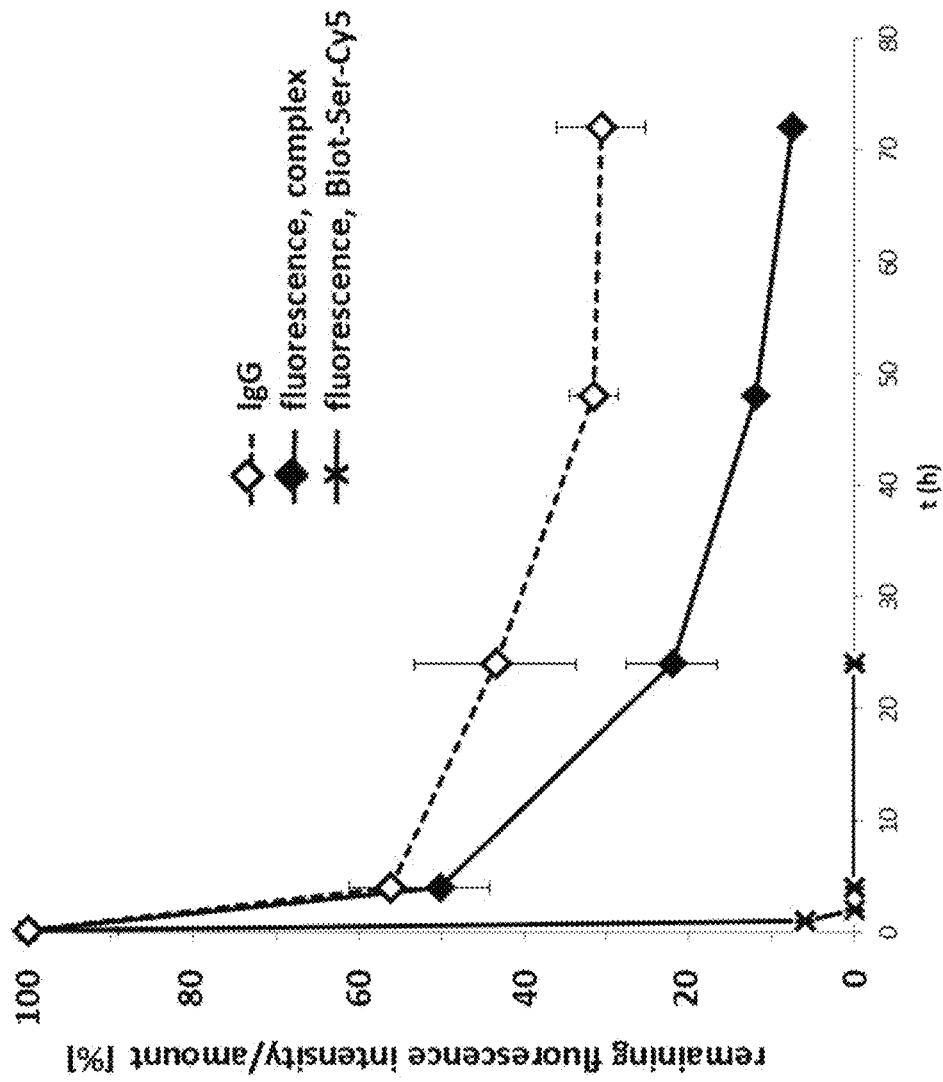
Figure 5B:
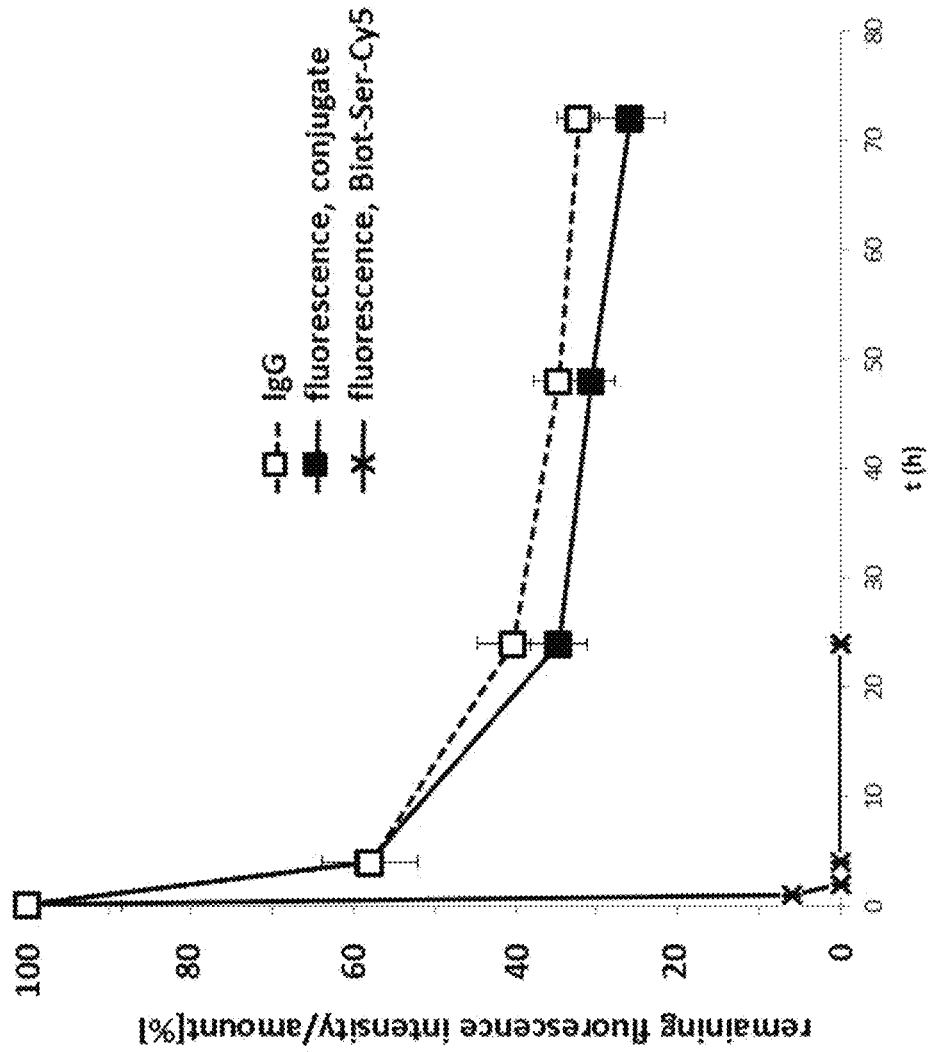

FIG. 5A-5B: Results of in vivo blood PK study with covalent conjugates and non-covalent complexes compared to non-complexed antigen/hapten; the relative remaining fluorescence intensity (%, solid marks) of Cy5-mediated fluorescence of Biotin-Cy5 non-covalent complexes (FIG. 5A) and covalent (SS-bridged) conjugates (FIG. 5B), as well as of non-complexed Biotin-Ser-Cy5 (asterix) is shown; the fluorescence signal at time point t=0.08 h was set to 100%; additionally, the relative remaining amount of human IgG in the mouse serum samples is shown (open marks); IgG serum concentration (mg/ml) at t=0.08 h was set to 100%.

Figure 6:
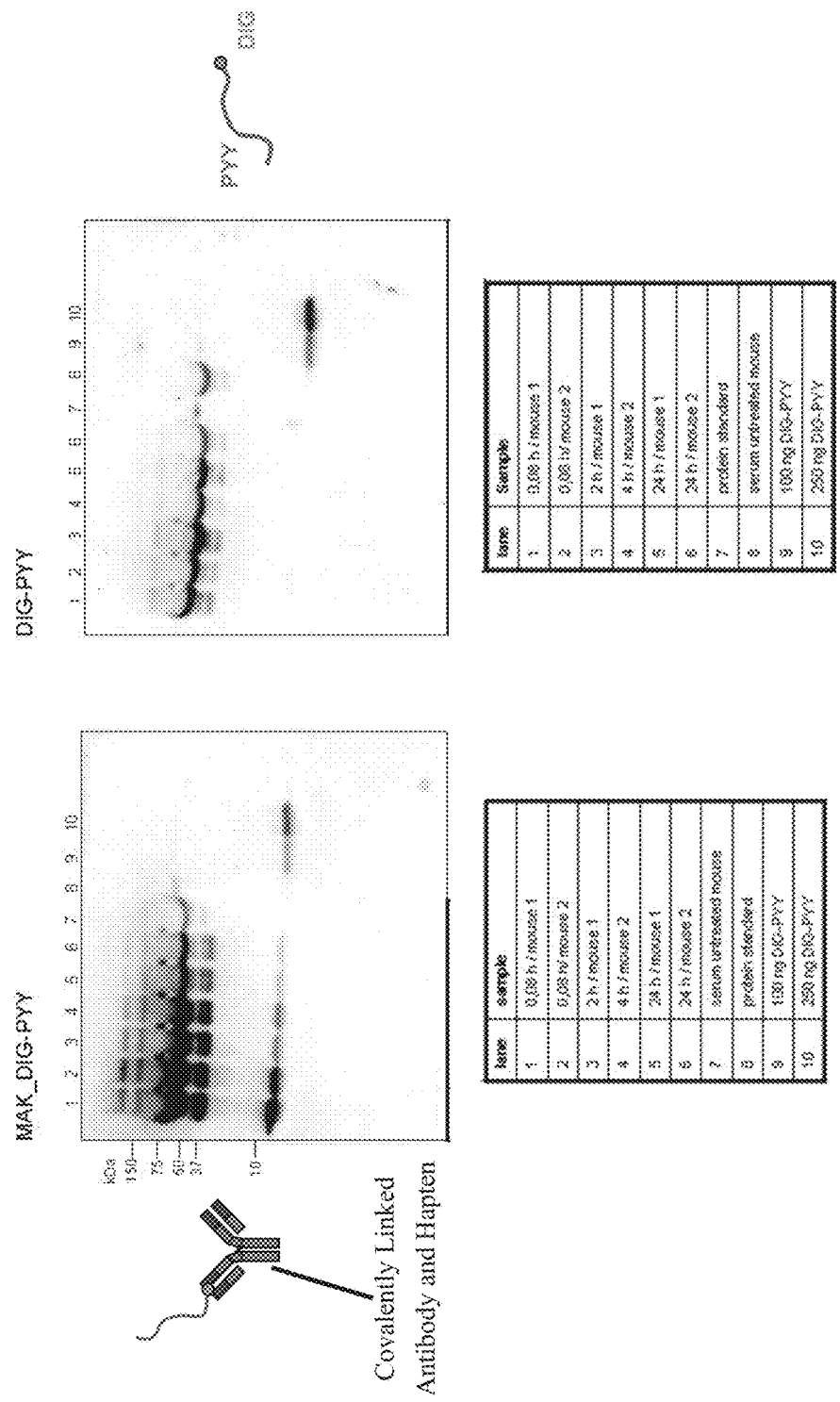

FIG. 6: Western blot of the determination of the amount of digoxigenylated PYY polypeptide in the serum of mice.

Figure 7:
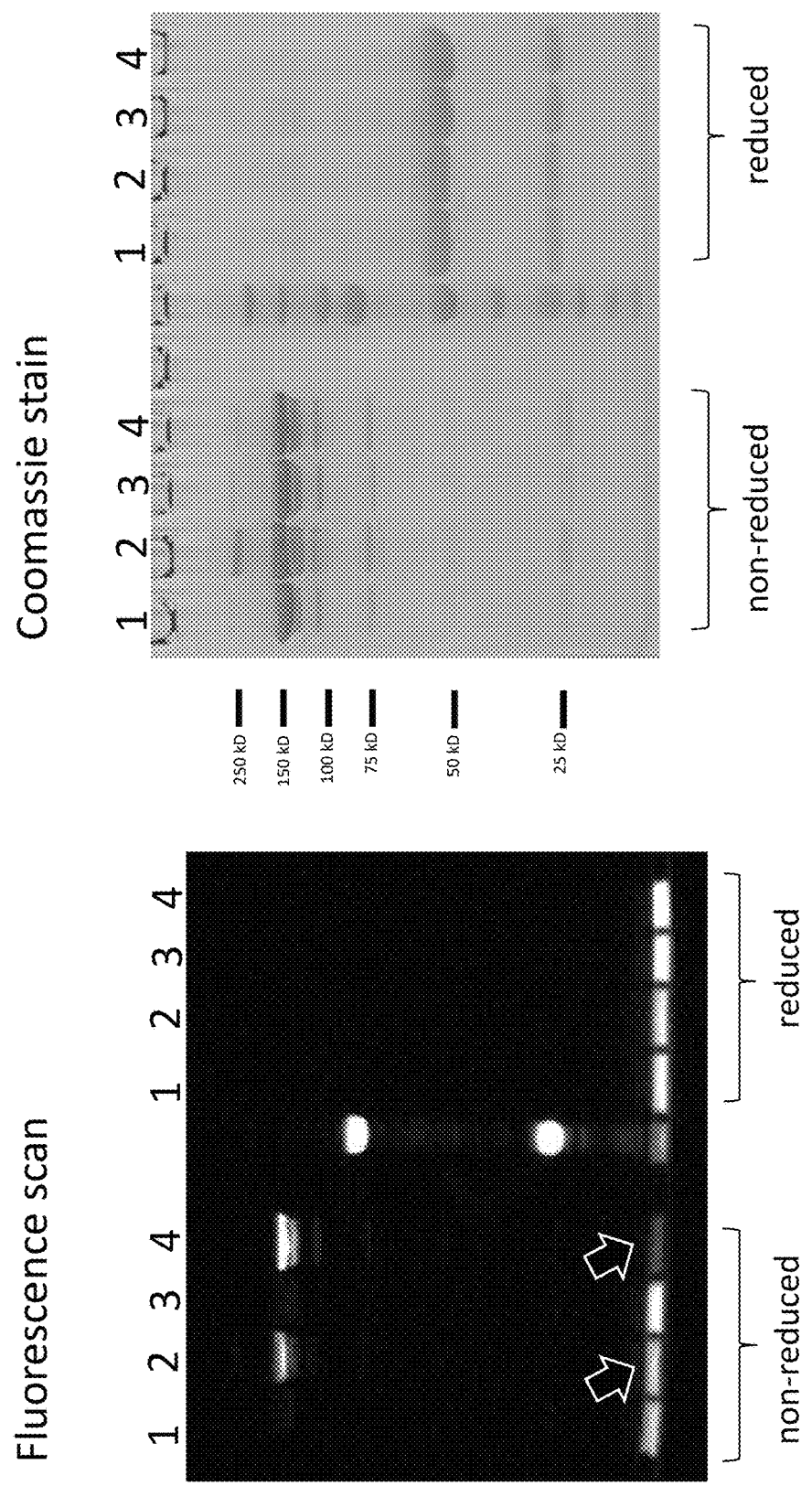

FIG. 7: Analysis of affinity-driven complexation of haptenylated compounds with anti-hapten antibodies.

Antibody complexation and subsequent covalent linkage at defined positions is directed by fluorescence signals in SDS PAGE analyses, which were carried out as described in Example 11.

Left: fluorescent image with non-reduced (left side of gel) and reduced (right side of gel) samples.

Right: Coomassie blue staining.

1: humanized anti-digoxigenin antibody+biotin-Cys-Cy5
2: humanized anti-digoxigenin antibody VH52bC+biotin-Cys-Cy5
3: humanized anti-biotin antibody+biotin-Cys-Cy5
4: humanized anti-biotin antibody VH53C+biotin-Cys-Cy5

The white arrows mark the excess (uncoupled) biotin-Cys-Cy5, which is significantly higher when anti-digoxigenin antibody VH52bC is used, because the conjugation reaction is not affinity driven in this case.

Figure 8:
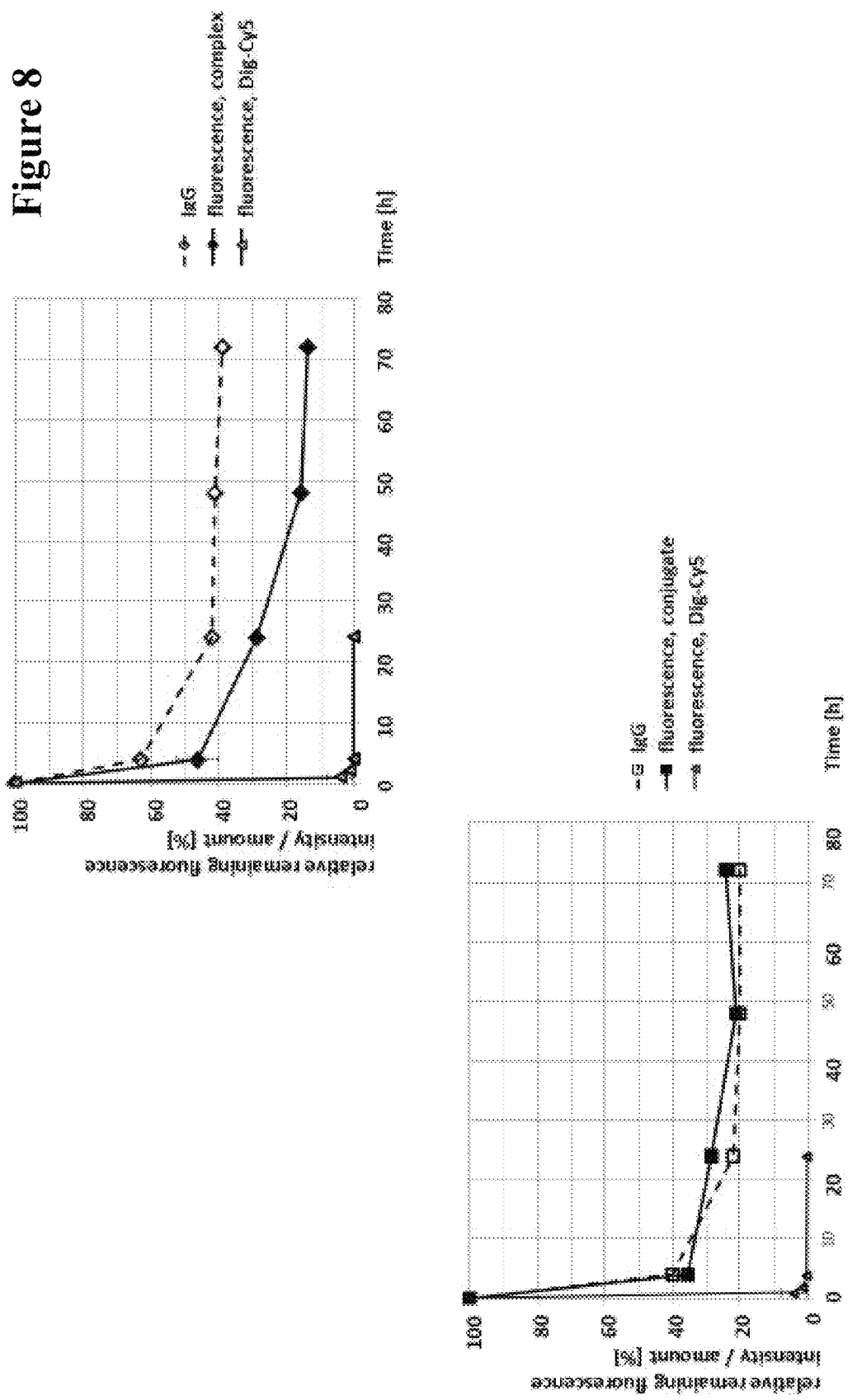

FIG. 8: Relative remaining fluorescence intensity (%) of Cy5-mediated fluorescence of Dig-Cy5 non-covalent complexes and covalent (disulfide-bridged) conjugates, as well as of non-complexed Dig-Cy5; the fluorescence signal at time point t=0.08 h was set to 100%; additionally, the relative remaining amount of human IgG in the mouse serum samples is shown; IgG serum concentration (mg/ml) at t=0.08 h was set to 100%.

Figure 9:
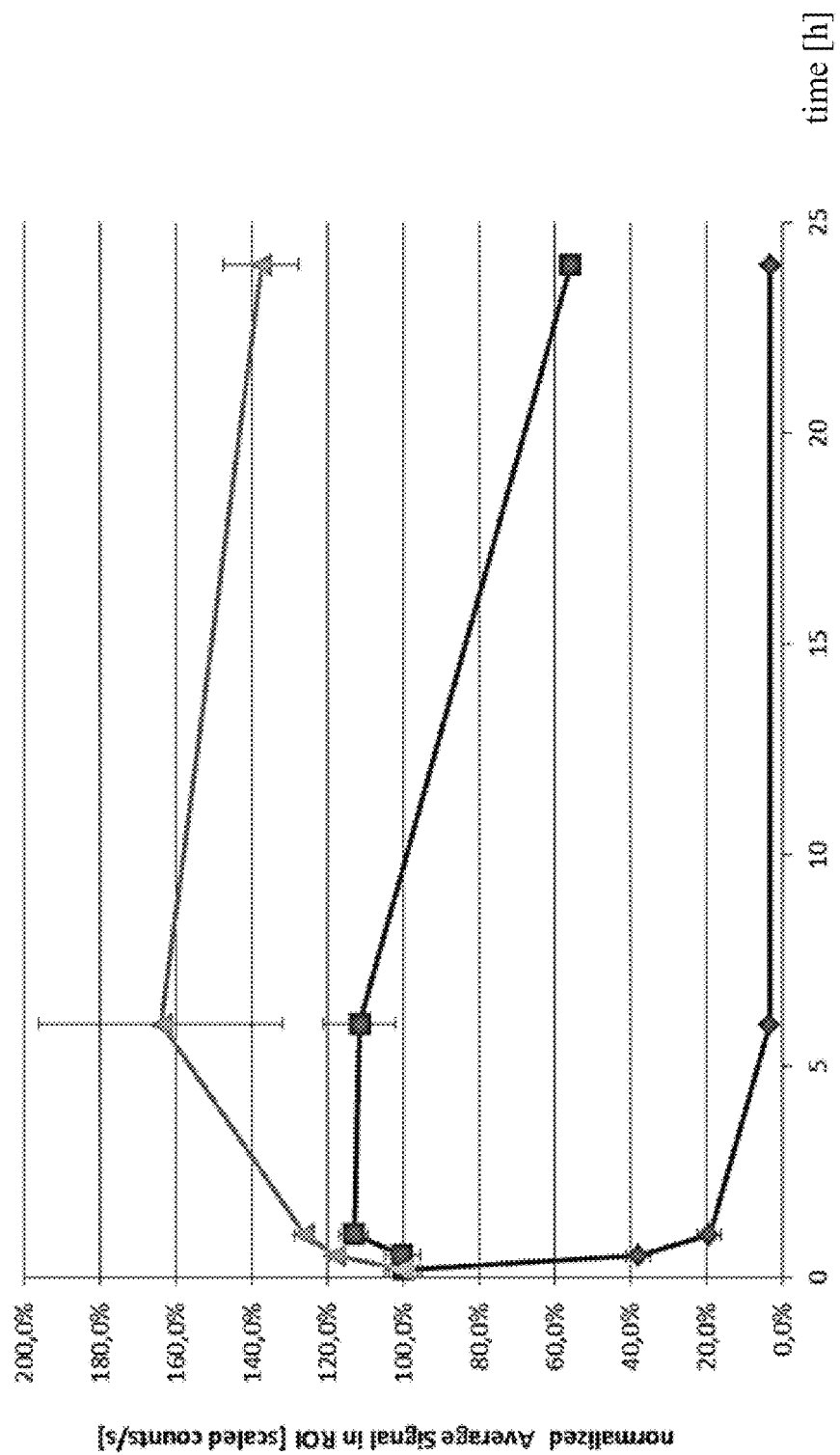

FIG. 9: Pharmacokinetics under in vivo-like conditions of Cy5-mediated fluorescence of Biotin-Cy5 of non-covalent complexes and of covalent (disulfide-bridged) conjugates, as well as of non-complexed Biotin-Cy5, determined by non-invasive eye imaging; solid diamond: biotin-Cy5, solid square biotin-Cy5+anti-biotin antibody (complex); triangle: Cy5-Biotin-anti-biotin antibody conjugate.

Figure 10:
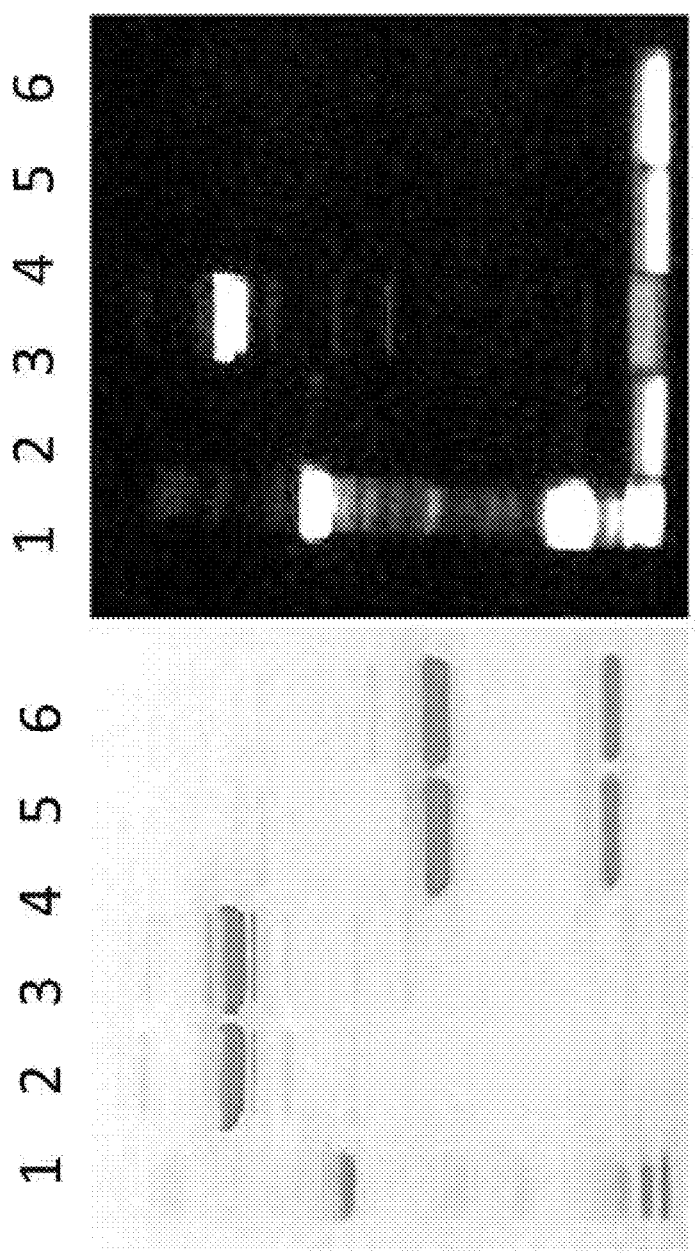

FIG. 10: Formation of covalent complexes between biotin-binding antibodies and Biotin-Cys-Cy5 is demonstrated by non-reducing and reducing SDS PAGE; the coupling reaction was performed in murine serum at 37° C. for 1 hr. Cy5 appears coupled to the H-chain under non-reducing conditions only in samples that contained Biotin-Cys-Cy5 and Cys-mutated antibody; these covalent conjugates disintegrate upon reduction (right lanes); lanes 1: Molecular weight marker; 2-3 non-reducing—2: anti-Biotin antibody (without Cys mutation)+Biotin-Cys-Cy5 (complex); 3: anti-Biotin antibody-Cys+Biotin-Cys-Cy5 (conjugate); 4-5 reducing—5: anti-Biotin antibody (without Cys mutation)+Biotin-Cys-Cy5 (complex); 6: anti-Biotin antibody-Cys+Biotin-Cys-Cy5 (conjugate).

Figure 11:
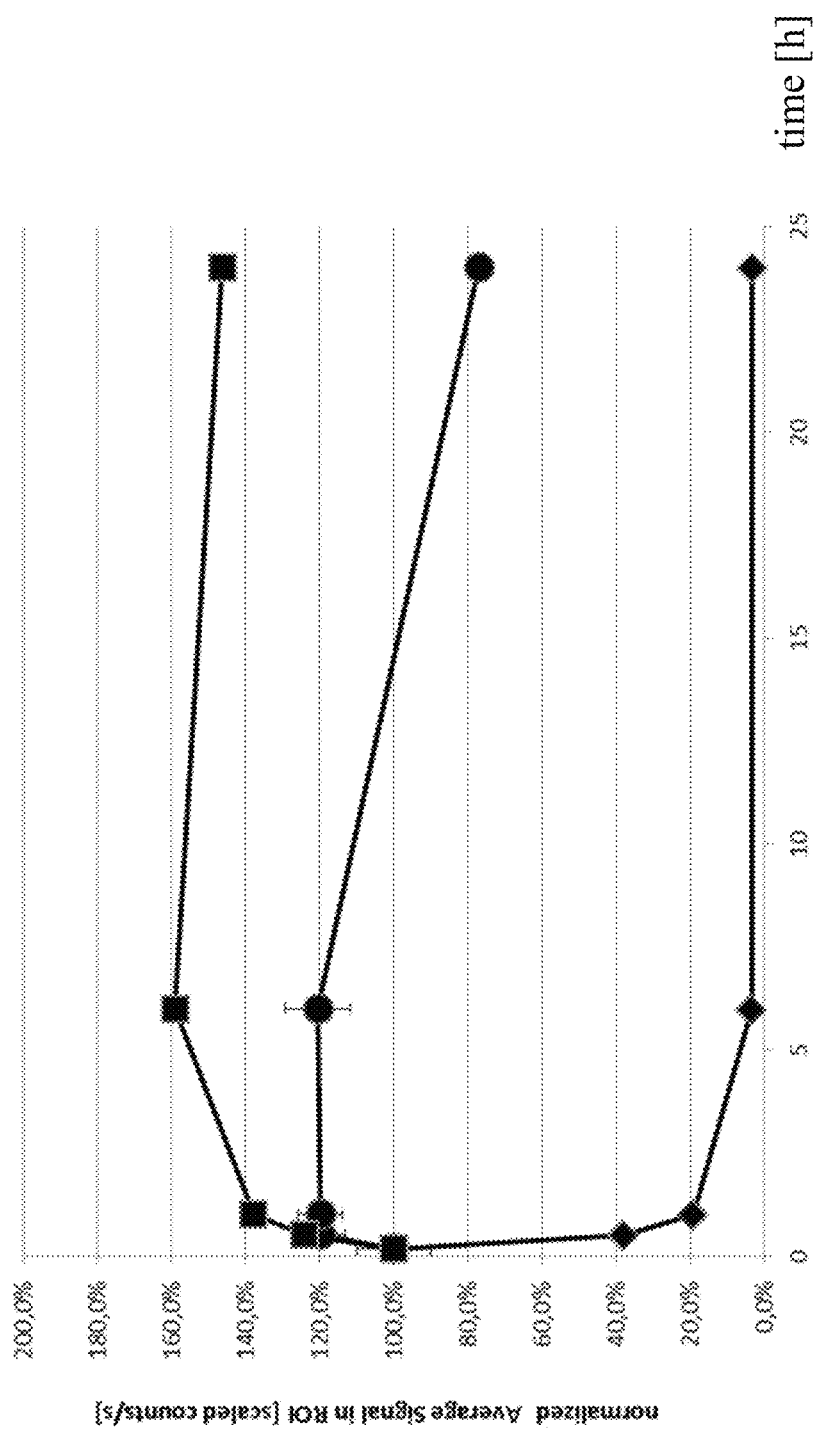

FIG. 11: In vivo pharmacokinetics of Cy5-mediated fluorescence of Biotin-Cy5 of non-covalent complexes and of covalent (disulfide-bridged) conjugates, as well as of non-complexed Biotin-Cy5, determined by non-invasive eye imaging; solid diamond: biotin-Cy5, solid circle: biotin-Cy5 administered 24 hours after administration of anti-biotin antibody (in vivo complex formation); solid square: biotin-Cys-Cy5 administered 24 hours after administration of anti-biotin antibody-Cys (in vivo conjugate formation).

Figure 12:
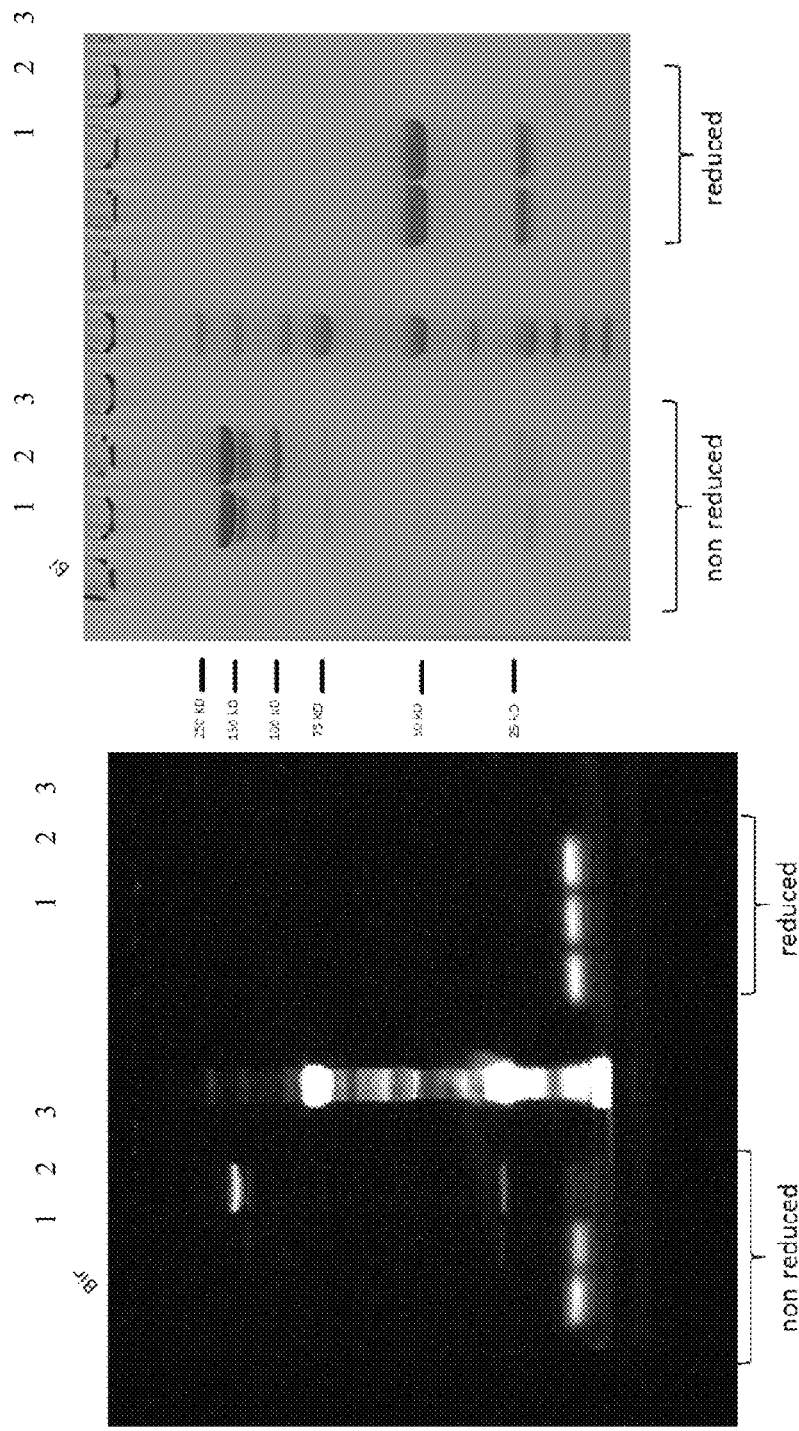

FIG. 12: SDS PAGE gel of the coupling of antibody 0155 with the helicar motif amino acid sequence cysteine variant 2 using a 2.5 molar excess of helicar motif amino acid sequence containing compound form the covalent complex 0156; 1=helicar motif amino acid sequence cysteine variant 2; 2=antibody 0019; 3=antibody 0155.

Figure 13:
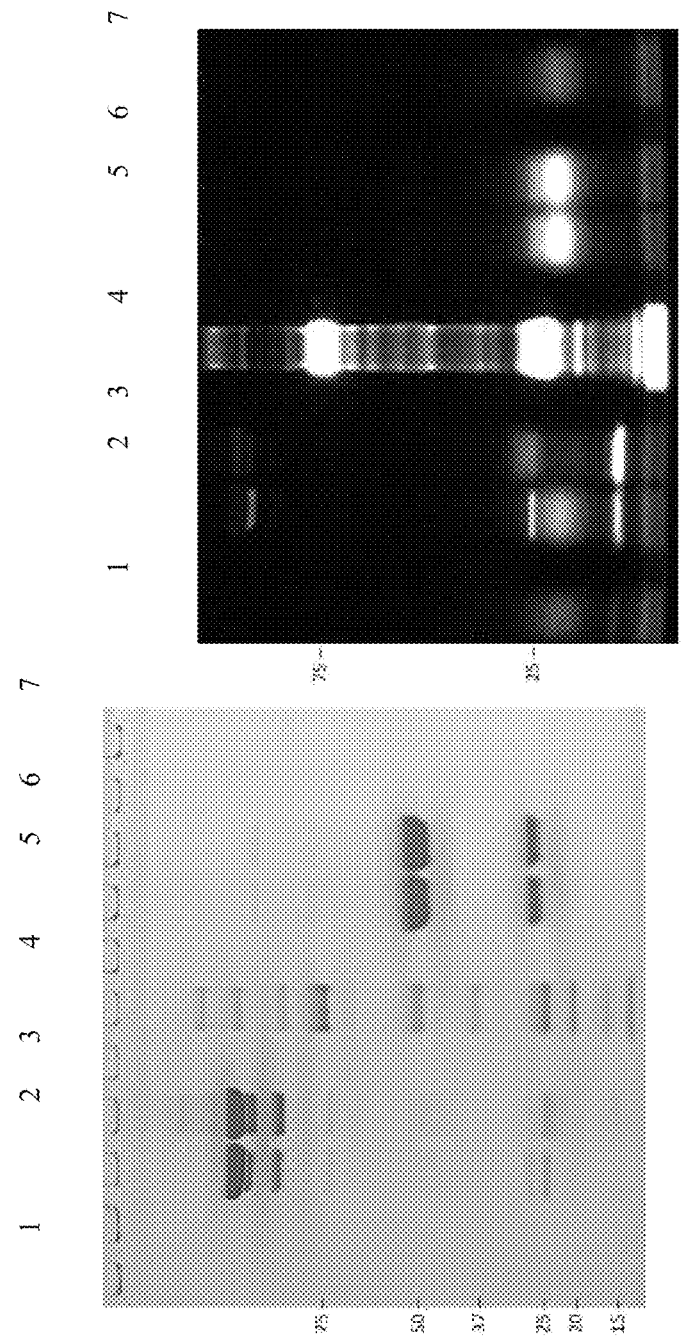

FIG. 13: SDS PAGE gel of the coupling of antibody 0157 with the helicar motif amino acid sequence cysteine variant 1; 1=helicar motif amino acid sequence cysteine variant 1 (oxidized); 2=control coupling (oxidized); 3=covalent conjugate (oxidized); 4=molecular weight marker; 5=covalent conjugate (reduced); 6=control coupling (reduced); 7=helicar motif amino acid sequence cysteine variant 1 (reduced).

Figure 14:
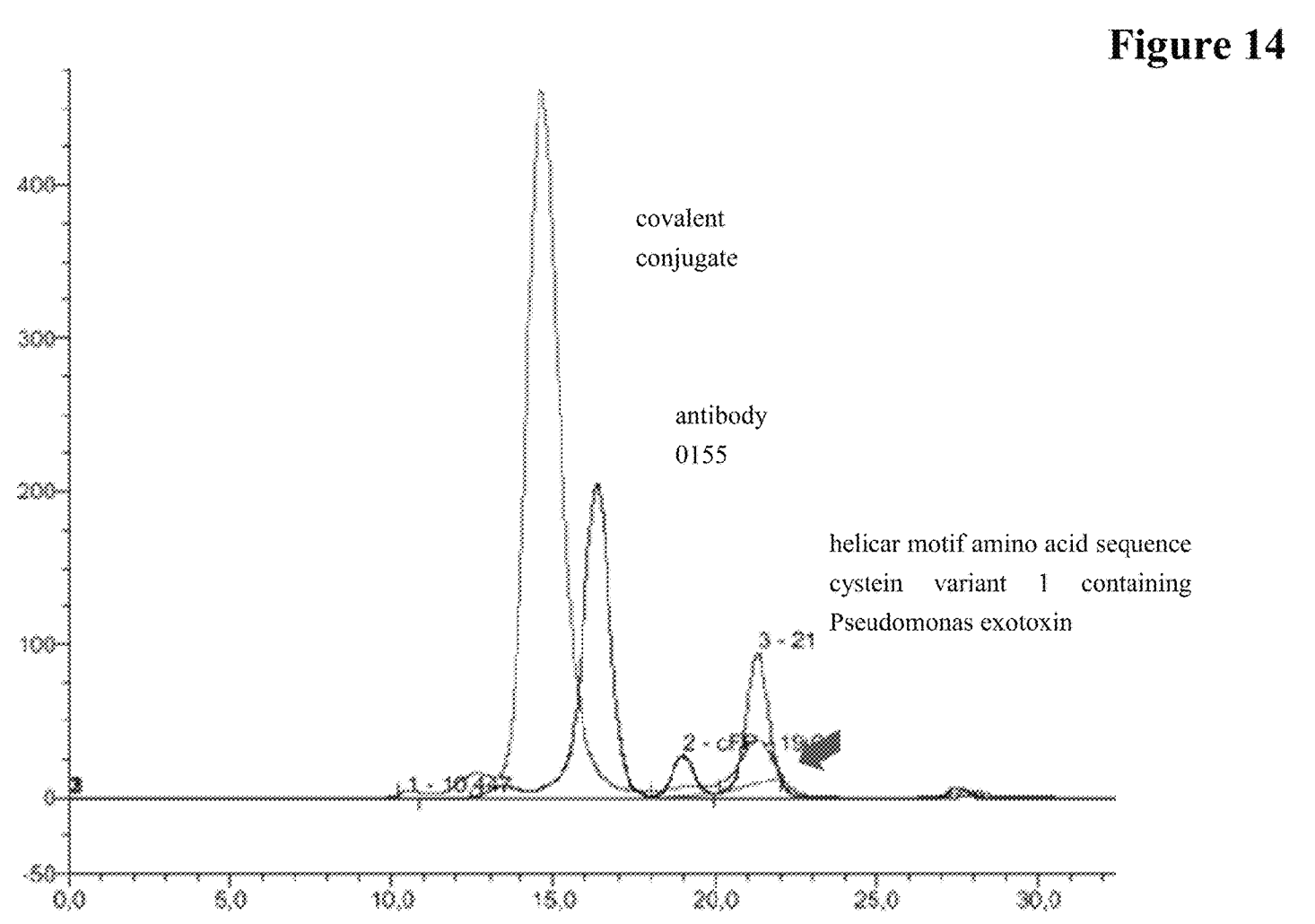

FIG. 14: SEC chromatogram of antibody 0155, the helicar motif amino acid sequence cysteine variant 1 containing *Pseudomonas* exotoxin molecule LR8M with the C-terminal lysine residue deleted of SEQ ID NO: 28 and the covalent conjugate thereof.

Figure 15:
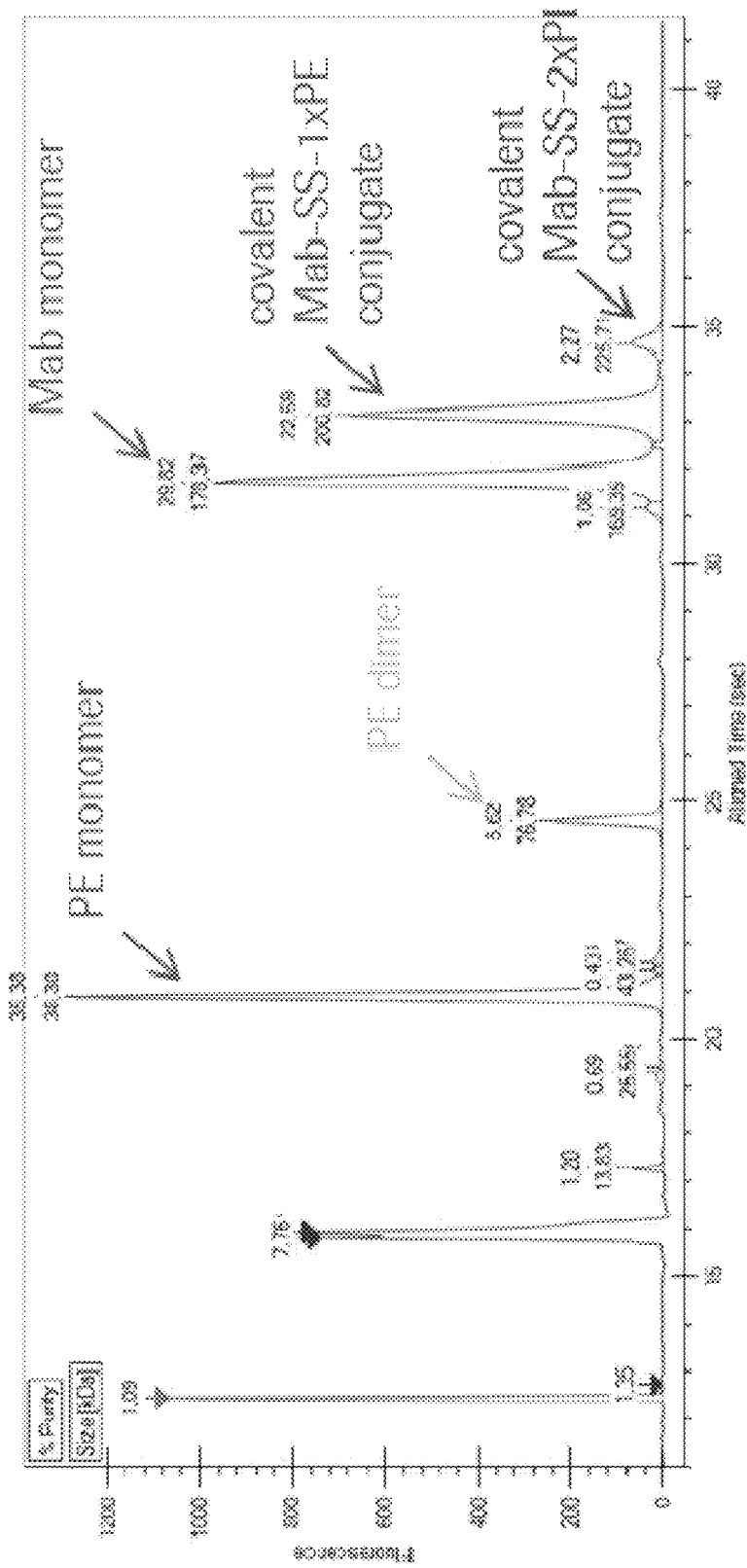

FIG. 15: Analysis of the conjugation efficiency by SDS-CE, Caliper, for the non reduced samples.

DETAILED DESCRIPTION OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "amino acid" denotes the group of carboxy α-amino acids, either occurring naturally, i.e. which directly or in form of a precursor can be encoded by a nucleic acid, or occurring non-naturally. The individual naturally occurring amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophane (Trp, W), tyrosine (Tyr, Y), and valine (Val, V). Examples of non-naturally occurring amino acids include, but are not limited to, Aad (alpha-aminoadipic acid), Abu (aminobutyric acid), Ach (alpha-aminocyclohexane-carboxylic acid), Acp (alpha-aminocyclopentane-carboxylic acid), Acpc (1-Aminocyclopropane-1-carboxylic acid), Aib (alpha-aminoisobutyric acid), Aic (2-Aminoindane-2-carboxylic acid; also called 2-2-Aic), 1-1-Aic (1-aminoindane-1-carboxylic acid), (2-aminoindane-2-carboxylic acid), allylglycine (allyl Gly), alloisoleucine (allo-Ile), Asu (alpha-aminosuberic acid, 2-aminooctanedioc acid), Bip (4-phenyl-phenylalanine-carboxylic acid), BnHP ((2S,4R)-4-hydroxy-proline), Cha (beta-cyclohexylalanine), Cit (citrulline), cyclohexylglycine (Chg), cyclopentylalanine, beta-cyclopropyl alanine, Dab (1,4-Diaminobutyric acid), Dap (1,3-Diaminopropionic acid), p (3,3-diphenylalanine-carboxylic acid), 3,3-Diphenyl alanine, Di-n-propylglycine (Dpg), 2-Furylalanine, Homocyclohexylalanine (HoCha), Homocitrulline (HoCit), Homocycloleucine, Homoleucin (HoLeu), Homoarginine (HoArg), Homoserine (HoSer), Hydroxyproline, Lys(Ac), (1) Nal (1-Naphtyl Alanine), (2) Nal (2-Naphtyl Alanine), 4-MeO-Apc (1-amino-4-(4-methoxyphenyl)-cyclohexane-1-carboxylic acid), Nor-leucine (Nle), Nva (Norvaline), Omathine, 3-Pal (alpha-amino-3-pyridylalanine-carboxylic acid), 4-Pal (alpha-amino-4-pyridylalaninecarboxylic acid), 3,4,5,F3-Phe (3,4,5-Trifluoro-phenylalanine), 2,3,4,5,6,F5-Phe (2,3,4,5,6-Pentafluorophenylalanine), Pqa (4-oxo-6-(1-piperazinyl)-3(4H)-quinazoline-acetic acid (CAS 889958-08-1)), Pyridylalanine, Quinolylalanine, Sarcosine (Sar), Thiazolylalanine, Thienylalanine, Tic (alpha-amino-1,2,3,4,tetrahydroisoquinoline-3-carboxylic acid), Tic(OH), Tle (tertbutyl-Glycine), and Tyr(Me).

The term "amino acid sequence variant" refers to polypeptides having amino acid sequences that differ to some extent from a native sequence polypeptide. Ordinarily, amino acid sequence variants will possess at least about 70% sequence identity with the native sequence polypeptide. In one embodiment the variant has about 80% or more sequence identity with the native sequence polypeptide. In one embodiment the variant has about 90% or more sequence identity with the native sequence polypeptide. In one embodiment the variant has about 95% or more sequence identity with the native sequence polypeptide. In one embodiment the variant has about 98% or more sequence identity with the native sequence polypeptide. The amino acid sequence variants possess substitutions, deletions, and/or insertions at certain positions within the amino acid sequence of the native amino acid sequence. Amino acids are designated by the conventional names, one-letter and three-letter codes.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody fragment" denotes a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "biotin", short "BI", denotes 5-[(3aS,4S,6aR)-2-oxohexahydro-1H-thieno[3,4-d]imidazol-4-yl]pentanoic acid. Biotin is also known as vitamin H or coenzyme R.

The term "bispecific antibodies" denotes antibodies which have two different (antigen/helicar) binding specificities. In one embodiment bispecific antibodies as reported herein are specific for two different antigens, i.e. a helicar motif amino acid sequence containing compound and a non-helicar motif amino acid sequence containing antigen.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, ι, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "digoxigenin", short "DIG", denotes 3-[(3S,5R,8R,9S,10S,12R,13S,14S,17R)-3,12,14-trihydroxy-10,13-dimethyl-1,2,3,4,5,6,7,8,9,11,12,15,16,17-tetradecahydro-cyclopenta[a]-phenanthren-17-yl]-2H-furan-5-one (CAS number 1672-46-4). Digoxigenin (DIG) is a steroid found exclusively in the flowers and leaves of the plants *Digitalis purpurea, Digitalis orientalis* and *Digitalis lanata* (foxgloves) (Polya, G., Biochemical targets of plant bioactive compounds, CRC Press, New York (2003) p. 847).

The term "effector functions" denotes those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "effective amount" of an agent, e.g., a pharmaceutical formulation, denotes an amount effective, at dosages and for periods of time necessary, to achieve the desired therapeutic or prophylactic result.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The term "fluorescein", short "FLUO", denotes 6-hydroxy-9-(2-carboxyphenyl)-(3H)-xanthen-3-on, alternatively 2-(6-hydroxy-3-oxo-(3H)-xanthen-9-yl)-benzoic acid. Fluorescein is also known as resorcinolphthalein, C.I. 45350, solvent yellow 94, D & C yellow no. 7, angiofluor, Japan yellow 201, or soap yellow.

The term "framework", short "FR", denotes heavy and light chain variable domain amino acid residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "free cysteine amino acid" denotes a cysteine amino acid residue which has been engineered into a parent antibody, has a thiol functional group (SH), and is not paired as an intramolecular disulfide bridge. Nevertheless, a free cysteine amino acid can be pair as intramolecular disulfide bridge, e.g. with glutathione.

The term "full length antibody" denotes an antibody having a structure substantially similar to a native antibody structure or having heavy chains that contain an Fc-region as defined herein. Native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "full length antibody" is an antibody comprising a VL and VH domain, as well as a light chain constant domain (CL) and heavy chain constant domains, CH1, CH2 and CH3. The constant domains may be native sequence constant domains (e.g., human native sequence constant domains) or an amino acid sequence variant thereof. The full length antibody may have one or more "effector functions" which refer to those biological activities attributable to the Fc constant region (a native sequence Fc-region or amino acid sequence variant Fc-region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B-cell receptor and BCR.

The term "hapten" denotes a small molecule that can elicit an immune response only when attached to a large carrier such as a protein. Exemplary haptens are aniline, o-, m-, and p-aminobenzoic acid, quinone, histamine-succinyl-glycine (HSG), hydralazine, halothane, indium-DTPA, fluorescein, biotin, digoxigenin, theophylline and dinitrophenol. In one embodiment the hapten is biotin or digoxigenin or theophylline or carborane or bromodeoxyuridine.

The term "helicar motif amino acid sequence" denotes an amino acid sequence that has the amino acid sequence of SEQ ID NO: 01 or is a variant thereof that is specifically bound by an anti-helicar antibody that has a variable heavy chain domain of SEQ ID NO: 04 and a light chain variable domain of SEQ ID NO: 05.

The term "a helicar motif amino acid sequence that is conjugated to" or "helicar motif amino acid sequence containing compound" denotes to a helicar motif amino acid sequence which is covalently linked to a further moiety such as a polypeptide or a label. An activated helicar motif amino acid sequence derivative can be used as starting material for the formation of such conjugates. In one embodiment the linker comprises a) one or more (in one embodiment three to six) methylene-carboxy-methyl groups (—$CH_2$—C(O)—), and/or b) from 1 to 10 (in one embodiment from 1 to 5) amino acid residues (in one embodiment selected from glycine, serine, glutamate, β-alanine, γ-aminobutyric acid, ε-aminocaproic acid or lysine), and/or c) one or more (in one embodiment one or two) compounds having the structural formula $NH_2$—[$(CH_2)_n$O]$_x$$CH_2$—$CH_2$—COOH in which n is 2 or 3 and x is 1 to 10, in one embodiment 1 to 7. The last element results (at least partly) in a linker (part) of the formula —NH—[$(CH_2)_n$O]$_x$$CH_2$—$CH_2$—C(O)—. One example of such a compound is e.g. 12-amino-4,7,10-trioxadodecanoic acid (results in a TEG (triethylenglycol) linker). In one embodiment the linker further comprises a maleimido group. The linker has a stabilizing and solubilizing effect since it contains charges or/and can form hydrogen bridges. In addition it can sterically facilitate the binding of the anti-helicar antibody to the helicar motif amino acid sequence containing compound. In one embodiment the linker is located at a side chain of an amino acid of the helicar motif amino acid sequence (e.g. conjugated to a lysine or cysteine side chain via an amino or thiol group). In one embodiment the linker is located at the amino terminus or at the carboxy terminus of the helicar amino acid sequence. The position of the linker on the conjugated compound (=payload) is typically chosen at a region where the biological activity of the payload is not affected. Therefore the attachment position of the linker depends on the nature of the payload and the relevant structure elements which are responsible for the biological activity. The biological activity of the payload to which the helicar motif amino acid sequence is attached can be tested in an in vitro assay.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "monospecific antibody" denotes an antibody that has one or more binding sites each of which has the same binding specificity, i.e. binds to the same antigen or helicar motif amino acid sequence.

A "naked antibody" refers to an antibody that is not conjugated to a heterologous moiety (e.g., a cytotoxic moiety) or radiolabel. The naked antibody may be present in a pharmaceutical formulation.

The term "package insert" is used to refer to instructions customarily included in commercial packages of therapeutic products, that contain information about the indications, usage, dosage, administration, combination therapy, contraindications and/or warnings concerning the use of such therapeutic products.

A "parent antibody" is an antibody comprising an amino acid sequence from which one or more amino acid residues are replaced by one or more cysteine residues. The parent antibody may comprise a native or wild-type sequence. The parent antibody may have pre-existing amino acid sequence modifications (such as additions, deletions and/or substitutions) relative to other native, wild-type, or modified forms of an antibody. The parent antibody binds specifically to a helicar motif amino acid sequence. A parent antibody may be directed additionally also against a target antigen of interest, e.g. a biologically important polypeptide. Antibodies directed against non-polypeptide antigens are also contemplated.

The term "payload" denotes any molecule or combination of molecules whose activity it is desired to be delivered (in)to and/or localize at a cell. Payloads include, but are not limited to labels, cytotoxins (e.g. Pseudomonas exotoxin, ricin, abrin, Diphtheria toxin, and the like), enzymes, growth factors, transcription factors, drugs, radionuclides, ligands, antibodies, liposomes, nanoparticles, viral particles, cytokines, and the like.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamylamines including altretamine, triethylenemelamine, trietylenephosphoramide, triethylenethiophosphoramide and trimethylomelamine; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitroureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("AraC"); cyclophosphamide; thiotepa; taxanes, e.g. paclitaxel (TAXOL®, Bristol-Myers Squibb Oncology, Princeton, N.J.) and docetaxel (TAXOTERE®, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-II; 35 topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

An "anti-angiogenic agent" refers to a compound which blocks, or interferes with to some degree, the development of blood vessels. The anti-angiogenic agent may, for instance, be a small molecule or an antibody that binds to a growth factor or growth factor receptor involved in promoting angiogenesis. The anti-angiogenic factor is in one embodiment an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and -P; mullerian-inhibiting substance; mouse gonadotropin-associated peptide; inhibin; activin; vascular endothelial growth factor; integrin; thrombopoietin (TPO); nerve growth factors such as NGF-p; platelet growth factor; transforming growth factors (TGFs) such as TGF-a and TGF-p; insulin-like growth factor-I and -II; erythropoietin (EPO); osteoinductive factors; interferons such as interferon-a, -P, and -y; colony stimulating factors (CSFs) such as macrophage-CSF (M-CSF); granulocyte-macrophage-CSF (GM-CSF); and granulocyte-CSF (GCSF); interleukins (ILs) such as IL-I, IL-1a, IL-2, IL-3, IL-4, IL-5, IL-6, IL-7, IL-8, IL-9, IL-IO, IL-II, IL-12; a tumor necrosis factor such as TNF-α or TNF-P; and other polypeptide factors including LIF and kit ligand (KL). As used herein, the term cytokine includes proteins from natural sources or from recombinant cell culture and biologically active equivalents of the native sequence cytokines.

The term "fMLP" denotes the tripeptide consisting of N-formylmethionine, leucine and phenylalanine. In one embodiment the effector moiety is fMLP or a derivative thereof.

The term "prodrug" refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, Vol. 14, 615th Meeting Belfast (1986) pp. 375-382 and Stella, et al., "Prodrugs: A Chemical Approach to Targeted Drug Delivery", Directed Drug Delivery, Borchardt, et al., (eds.), pp. 247-267, Humana Press (1985). The prodrugs that can be used as effector moiety include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described herein.

The term "cytotoxic moiety" refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington, D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject, A pharmaceutically acceptable carrier includes, but is not limited to, a buffer, excipient, stabilizer, or preservative.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters.

The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

All polypeptide sequences are written according to the generally accepted convention whereby the alpha-N-terminal amino acid residue is on the left and the alpha-C-terminal amino acid residue is on the right. As used herein, the term "N-terminus" refers to the free alpha-amino group of an amino acid in a polypeptide, and the term "C-terminus" refers to the free a-carboxylic acid terminus of an amino acid in a polypeptide. A polypeptide which is N-terminated with a group refers to a polypeptide bearing a group on the alpha-amino nitrogen of the N-terminal amino acid residue. An amino acid which is N-terminated with a group refers to an amino acid bearing a group on the alpha-amino nitrogen.

Unless indicated otherwise by a "D" prefix, e.g., D-Ala or N-Me-D-Ile, or written in lower case format, e.g., a, i, 1, (D versions of Ala, Ile, Leu), the stereochemistry of the alpha-carbon of the amino acids and aminoacyl residues in polypeptides described in this specification and the appended claims is the natural or "L" configuration. The Cahn-Ingold-Prelog "R" and "S" designations are used to specify the stereochemistry of chiral centers in certain acyl substituents at the N-terminus of the polypeptides. The designation "R,S" is meant to indicate a racemic mixture of the two enantiomeric forms. This nomenclature follows that described in Cahn, R. S., et al., Angew. Chem. Int. Ed. Engl. 5 (1966) 385-415.

The term "single-chain Fv", short "scFv", denotes an antibody fragment that comprise the VH and VL domains of antibody, wherein these domains are present in a single polypeptide chain. In one embodiment, the Fv polypeptide further comprises a polypeptide linker between the VH and VL domains which enables the scFv to form the desired structure for antigen binding. For a review of scFv, see Plueckthun in The Pharmacology of Monoclonal Antibodies, vol. 113, Rosenburg and Moore (Eds), Springer-Verlag, New York, pp. 269-315 (1994).

The term "theophylline", short "THEO", denotes 1,3-dimethyl-7H-purine-2,6-dione. Theophylline is also known as dimethylxanthine.

The term "treatment" (and grammatical variations thereof such as "treat" or "treating") denotes a clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "x-valent", e.g. "mono-valent" or "bi-valent" or "tri-valent" or "tetra-valent", denotes the presence of a specified number of binding sites, i.e. "x", in an antibody molecule. As such, the terms "bivalent", "tetravalent", and "hexavalent" denote the presence of two binding site, four binding sites, and six binding sites, respectively, in an antibody molecule. The bispecific antibodies as reported herein are at least "bivalent" and may be "trivalent" or "multivalent" (e.g. "tetravalent" or "hexavalent"). In one embodiment the bispecific antibody as reported herein is bivalent, trivalent, or tetravalent. In one embodiment the bispecific antibody is bivalent. In one embodiment the bispecific antibody is trivalent. In one embodiment the bispecific antibody is tetravalent.

In certain aspects and embodiments the antibodies as reported herein have two or more binding sites and are bispecific. That is, the antibodies may be bispecific even in cases where there are more than two binding sites (i.e. that the antibody is trivalent or multivalent). The term bispecific antibodies includes, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for a helicar motif amino acid sequence, a second binding site is specific for a non-helicar motif amino acid sequence antigen, and vice versa.

The term "variable region" denotes the domain of an antibody heavy or light chain that is involved in binding the antibody to its antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector" denotes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Conjugates as Reported Herein

In one aspect the invention is based on the finding that a covalent conjugate comprising an helicar motif amino acid sequence containing compound and an anti-helicar motif amino acid sequence antibody that specifically binds to the helicar motif amino acid sequence can be obtained by the formation of a covalent bond between a properly placed functional group in the helicar motif amino acid sequence and a functional group in a variable domain of the antibody, especially in the CDR2 of the antibody, whereby the CDR2 is determined according to the variable domain numbering according to Kabat.

In one embodiment the helicar motif amino acid sequence containing compound is a conjugate comprising a helicar motif amino acid sequence, a linker and a payload.

In certain embodiments the functional group may contain electron deficient double bonds or a thiol. In one embodiment the functional group is a maleimide or a cysteine.

As the conjugates as reported herein can be used a therapeutic agent in humans also a humanized variant of the above antibody that specifically binds to the helicar motif amino acid sequence is provided herein.

Covalent conjugates of a helicar motif amino acid sequence containing compound and an anti-helicar motif amino acid sequence antibody may confer benign biophysical behavior and improved PK properties to the helicar motif amino acid sequence containing compound. Furthermore, in case a bispecific antibody is used, the conjugates can be used to target the helicar motif amino acid sequence containing compound to cells which display the antigen that is recognized by the second binding specificity of the bispecific antibody. Such conjugates are composed of one anti-helicar motif amino acid sequence binding specificity and one further (non-helicar motif amino acid sequence) antigen binding specificity. The stoichiometric ratio of antibody to helicar motif amino acid sequence containing polypeptide depends on the format of the bispecific antibody and can be 1:1, 1:2, 2:1, 2:2, 2:4 and 4:2 (antibody: helicar motif amino acid sequence containing polypeptide).

It is desired that the biologically active compound in the helicar motif amino acid sequence containing compound retains good biological activity despite being conjugated to the helicar motif amino acid sequence, as well as being conjugated to the antibody. It is also desired (in case of bispecific targeting modules) that the cell surface target binding site of the bispecific antibody retains its binding specificity and affinity in the presence of the covalently conjugated helicar motif containing compound.

The reactive group in the helicar motif amino acid sequence may be any reactive group, such as e.g. a maleimide, e.g. N-ethyl maleimide (NEM), a iodoacetamide, a pyridyl disulfide, or other reactive conjugation partner (see e.g. Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labeling: A Practical Approach, Academic Press, London; Means (1990) Bioconjugate Chem. 1:2; Hermanson, G. in Bioconjugate Techniques (1996) Academic Press, San Diego, pp. 40-55 and 643-671).

The reactive group on the antibody is limited to those that can be selectively, i.e. position specifically, generated. Therefore, it is limited to the side chain groups of the amino acid residues cysteine, serine, asparagine, glutamine, tyrosine, lysine, arginine, aspartic acid, and glutamic acid.

For the formation of a covalent conjugate between the anti-helicar motif amino acid sequence antibody and the helicar motif amino acid sequence containing compound both have to be modified by the introduction of a reactive group. Upon binding of the helicar motif amino acid sequence by the anti-helicar motif amino acid sequence antibody the two reactive groups are brought in close proximity allowing the formation of a covalent bond. In one embodiment the modification is the introduction of a thiol functionality in each of the compounds. In one embodiment the thiol compound is a cysteine residue.

The position to be mutated must simultaneously meet two requirements: (i) the coupling positions should be in proximity to the binding region to utilize the helicar motif amino acid sequence positioning effect for directed coupling, and (ii) the mutation and coupling position must be positioned in a manner that helicar motif amino acid sequence binding by itself is not affected. These requirements for finding a suitable position are de facto 'contradicting' each other because requirement (i) is best served by a position close to the binding site, while requirement (ii) is most safely achieved by positions that are distant from the binding site.

Despite these virtually excluding requirements, a position was identified that can be mutated without affecting helicar motif amino acid sequence positioning, and which nevertheless simultaneously allow directed covalent coupling.

One position is located at position VL55 according to the Kabat numbering of the light chain variable domain.

One position is located at position VL51 according to the Kabat numbering of the light chain variable domain.

These positions are applicable to the helicar motif amino acid sequence antibody and, thus, it is not required to start from scratch every time a new covalent conjugate has to be made. Only the helicar motif amino acid sequence as to be introduced in/conjugate to the payload.

The antibodies modified as reported herein retain the helicar motif amino acid sequence binding capability of their parent (i.e. wild-type) antibody counterparts. Thus, the engineered antibody is capable of binding, in one embodiment it is capable of specifically binding, to the helicar motif amino acid sequence.

The terms "binding specificity" or "an antibody that binds to" denote that the molecule comprising the binding specificity or an antibody can form a complex with a further molecule in a specific manner. The binding can be detected in an in vitro assay, such as in a plasmon resonance assay (BIAcore, GE-Healthcare Uppsala, Sweden). The affinity of the complex formation is defined by the terms $k_a$ (rate constant for the association of the compounds to form the complex), $k_D$ (dissociation constant, dissociation of the complex), and $K_D$ ($k_D$/ka). Binding or specifically binding means a binding affinity ($K_D$) of about $10^{-7}$ M or less, in one embodiment of about $10^{-8}$ M to about $10^{-13}$ M, in one embodiment of about $10^{-9}$ M to about $10^{-13}$ M. Thus, an antibody that binds to the helicar motif amino acid sequence to form a complex as reported herein specifically binds to the helicar motif amino acid sequence with a binding affinity ($K_D$) of about $10^{-8}$ mol/l or less, in one embodiment of about $10^{-8}$ mol/l to about $10^{-13}$ mol/l.

It has been found that the formation of a covalent bond between a cysteine-modified anti-helicar motif amino acid sequence antibody and a cysteine-modified helicar motif amino acid sequence containing compound bearing the cysteine residue in the helicar motif amino acid sequence takes place upon binding of the antibody to the helicar motif amino acid sequence without the requirement of the addition of reducing and/or oxidizing agents if the formed bond is a disulfide bond. Thus, the disulfide bridge between the two compounds is formed spontaneously upon formation of the non-covalent complex. Therefore, a method for the formation of a covalent complex as reported herein simply requires the mixing of the two compounds. The only prerequisite for the formation of the disulfide bond is a proper orientation of the two compounds with respect to each other.

The engineered antibodies as reported herein may be site-specifically and efficiently covalently conjugated (coupled) with a helicar motif amino acid sequence comprising a reactive group.

Replacement of the amino acid residue at position VL55 or VL51, respectively, (according to the Kabat numbering scheme) with a cysteine residue resulted in anti-helicar motif amino acid sequence antibody derivatives with heavy chain variable region sequences that are listed in SEQ ID NO: 06 and SEQ ID NO: 07.

One aspect as reported herein is an anti-helicar motif amino acid sequence antibody that is a humanized antibody. In one embodiment the anti-helicar motif amino acid sequence antibody comprises a humanized heavy chain variable domain derived from the heavy chain variable domain that has the amino acid sequence of SEQ ID NO: 04 and a humanized light chain variable domain derived from a light chain variable domain that has the amino acid sequence of SEQ ID NO: 05.

One aspect as reported herein is an anti-helicar motif amino acid sequence antibody that is a humanized antibody. In one embodiment the anti-helicar motif amino acid sequence antibody comprises a humanized heavy chain variable domain derived from the heavy chain variable domain that has the amino acid sequence of SEQ ID NO: 04 and a humanized light chain variable domain derived from a light chain variable domain that has the amino acid sequence of SEQ ID NO: 06.

One aspect as reported herein is an anti-helicar motif amino acid sequence antibody that is a humanized antibody. In one embodiment the anti-helicar motif amino acid sequence antibody comprises a humanized heavy chain variable domain derived from the heavy chain variable domain that has the amino acid sequence of SEQ ID NO: 04 and a humanized light chain variable domain derived from a light chain variable domain that has the amino acid sequence of SEQ ID NO: 07.

One aspect as reported herein is an anti-helicar motif amino acid sequence antibody that comprises CDRs as in the variable domain of SEQ ID NO: 04 for the heavy chain and as in any of the variable domains of SEQ ID NO: 05, or SEQ ID NO: 06, or SEQ ID NO: 07 for the light chain variable domain and further comprises an acceptor human framework, e.g. a human immunoglobulin framework or a human consensus framework.

One aspect as reported herein is an anti-helicar motif amino acid sequence antibody that comprises hypervariable loops as in the variable domain of SEQ ID NO: 04 for the heavy chain and as in any of the variable domains of SEQ ID NO: 05, or SEQ ID NO: 06, or SEQ ID NO: 07 for the light chain variable domain and further comprises an acceptor human framework, e.g. a human immunoglobulin framework or a human consensus framework.

For example, PYY was modified to comprise the helicar motif amino acid sequence and complexed by an anti-helicar motif amino acid sequence antibody in order to get advantage of the pharmacokinetic properties of the antibody and to avoid the intrinsic instability of the PYY.

The structural investigation of the $PYY_{3-36}$ peptide (Nygaard, R., et al., Biochem. 45 (2006) 8350-8357; SEQ ID NO: 26) reveals a helical motif (helicar-like motif amino acid sequence) for the central amino acids. As the N-terminal isoleucine and the modified C-terminus have been described as essential for the functional activity of the peptide, the central helix was modified in order to reflect the amino acids in the helicar motif amino acid sequence.

| | | | |
|---|---|---|---|
| PYY (3-36) (SEQ ID NO. 26) | 3 IKPEAPGEDASPEELNRYYASLRHYLNLVTRQRYNH2 | | 36 |
| Helicar motif | AHLENEVARLKK | | |
| PYY_helicar (SEQ ID NO: 27) | IKPEAPGEDASPEAHLANEVARLHYLNLVTRQRYNH2 (YNH2 = tyrosine amide) | | |

| | binding [$K_d$] | soluble in PBS | |
|---|---|---|---|
| PYY(3-36) (SEQ ID NO: 26) | — | + | PYY wild-type |
| PYY_helicar (SEQ ID NO: 27) | 12 nM | + | helicar motif engineered PYY |

The full IgG1 anti-helicar motif amino acid sequence antibody 0019 and the modified PYY peptide PYY_helicar was obtained in vitro by applying a small excess of the peptide to the antibody solution. The complex 0052 was formed. The stoichiometry of the complex was determined by SEC-Malls analytical experiments to be 1.6 peptides complexed on one bivalent antibody.

The antibody 0019, the PYY(3-36) wild-type, the PYY_helicar and the complex 0052 were tested for their effect on to the Y2Receptor family.

As the 12-mer peptide (helicar motif amino acid sequence) is a relatively rigid entity (at least when complexed by a specific anti-helicar motif amino acid sequence antibody) it has been found that a structurally specific design for the disulfide bridge has to be used. As the complex formation and the thereafter effected covalent coupling is between two recombinantly produced entities, the artificial cysteine residues introduced for the formation of a covalent disulfide bond are not produced necessarily as free cysteine

| | NPY2R | NPY1R | NPY4R | NPY5R |
|---|---|---|---|---|
| Ac-Ile-Lys-Pqa-Arg-His-Tyr-Leu-Asn-Trp-Val-Thr-Arg-Gln-(NMe)-Arg-Try-NH2 * 4 HOAc | 1.0 nM | inactive | inactive | inactive |
| PYY_helicar (IKPEAPGEDASPEAHLANEVARLH YLNLVTRQRYNH2) (SEQ ID NO: 27) | 6.38 nM | inactive | inactive | inactive |
| PYY(3-36) (IKPEAPGEDASPEELNRYYASLRHY LNLVTRQRYNH2) (SEQ ID NO: 26) charge 1 | 0.05 nM | 168 nM | 162 nM | 170 nM |
| PYY(3-36) (IKPEAPGEDASPEELNRYYASLRHY LNLVTRQRYNH2) (SEQ ID NO: 26) charge 2 | 0.05 nM | 160 nM | 131 nM | 202 nM |
| anti-helicar motif amino acid sequence antibody (0019) | inactive | inactive | inactive | inactive |
| anti-helicar motif amino acid sequence antibody-PYY_helicar complex (0052) | 0.93 nM | inactive | inactive | inactive |

As demonstrated (Hoffmann, E., et al., J. Cont. Rel. 171 (2013) 48-56.) the peptides complexed by an antibody have a prolonged half-life in vivo. Moreover and surprisingly, the complex demonstrates a slightly better affinity for the NPY2R receptor compared to the non-complexed peptide; the antibody stabilizes the polypeptide and presents the peptide in its fixed biologically active conformation.

In order to increase the in vitro and in vivo stability of the complex between the anti-helicar motif amino acid sequence antibody and the helicar motif amino acid sequence containing compound, the formation of a disulfide bridge upon binding has been used.

The first step is a specific recognition step (high affinity interaction), i.e. the formation of the helicar motif amino acid sequence containing compound-anti-helicar motif amino acid sequence antibody complex. This is followed in the second step by a spontaneous shuffling of a disulfide bridge to form the stability improved covalent complex.

residues but are expressed in a reduced from, i.e. conjugated to a free cysteine or homo cysteine amino acid.

The position in the amino acid sequence of the anti-helicar motif amino acid sequence antibody variable domain where the artificial free cysteine residue is introduced is critical. A non-exposed cysteine in the antibody variable domain amino acid sequence has more probability to be expressed as a free cysteine (not conjugated), whereas an exposed cysteine residue close to the binding pocket can abolish the binding of the 12-mer peptide (helicar motif amino acid sequence) due to a steric hindrance induced by the cysteine conjugation to an additional moiety like a free cysteine.

In order to identify a suitable position which has minimum risk of steric hindrance and strong affinity reduction, different positions for the introduction of the artificial cysteine residue in the helicar motif amino acid sequence have been tested. The cysteine residue has been introduced at the C-terminal end of the 12 mer (helicar motif amino acid sequence) in order to have the major part of the paratope unchanged. The peptides have been synthesized and fused to a fluorescent motif

```
wild-type:                AHLENEVARLKK (SEQ ID NO: 1)

cysteine variant 1:       AHLENEVARCKK (SEQ ID NO: 2)
                       -> AHLENEVARCKK (5-Fluo)-OH cysteine variant 2:       AHLENEVARLCK (SEQ ID NO: 03)
                       -> AHLENEVARLCK (5-Fluo)-OH x TFA
```

On the antibody, a structural design has been done to allow the formation of the disulfide bridge for both designed peptides including each a cysteine in different 3D environment.

The 12-mer helical peptide AHLENEVARLKK (helicar motif amino acid sequence) is modeled into the VH and the VH domains. At the C-terminus of the peptide the residues L10 and K11 are identified as possible position and in the light chain variable domain the positions N55 and G51 according to the light chain numbering of Kabat are identified.

The bivalent antibody 0155 (N55C) was coupled to the helicar motif amino acid sequence cysteine variant 2. On the SDS page (denaturing condition, see FIG. 12) the fluorescence is seen only on the antibody 0155; in the reducing condition, only the small peptide is visible.

The covalent conjugation of the helicar motif amino acid sequence containing fluorescent compound to the anti-helicar motif amino acid sequence antibody was successful.

The coupling of antibody 0157 (G51C) with the helicar motif amino acid sequence cysteine variant 1 was not resulting in the expected covalent complex. The fluorescence is not seen in the expected lane but on the reference which should be negative in this experiment (see FIG. 13).

The covalent conjugation of the helicar motif amino acid sequence containing fluorescent compound to the anti-helicar motif amino acid sequence antibody 0157 was not successful. Without being bound by this theory it is assumed that in this case the antibody cysteinylation is too deep in the binding pocket to allow the helicar motif amino acid sequence containing fluorescent compound to bind efficiently and deliver the nucleophilic thiol group in an appropriate position to attack the C51.

The helicar based methodology becomes particularly attractive when considering the formation of a covalent complex with a recombinantly produced helicar motif amino acid sequence containing polypeptide.

As the conjugation of the antibody 0155 containing the VL-N55C mutation with the helicar motif amino acid sequence cysteine variant 1 (AHLENEVARLCK; SEQ ID NO: 02) has much better performed compared to the alternative (G51C on VL with helicar motif amino acid sequence cysteine variant 2 (AHLENEVARCKK; SEQ ID NO: 03)), the conjugation of 0155 with a helicar motif amino acid sequence cysteine variant 1 containing polypeptide was further investigated. The polypeptide contained the helicar motif amino acid sequence cysteine variant 1 (AHLENEVARLCK; SEQ ID NO: 02) fused to the N-terminus.

Antibody 0155 is covalently conjugated with the helicar motif amino acid sequence cysteine variant 1 containing *Pseudomonas* exotoxin molecule LR8M with the C-terminal lysine residue deleted of SEQ ID NO: 28. The SEC chromatogram is shown in FIG. 14. The conjugation efficiency is analyzed by SDS-CE, Caliper, for the non reduced samples (see FIG. 15).

In conclusion, the anti-helicar motif amino acid sequence monoclonal antibody can be used to complex peptides, small molecules with peptidic linker, and recombinant proteins via a high affinity recognition of a 12-mer helicar motif amino acid sequence. Peptides with propensity to fold as helix can be modified to mimic the original 12-mer helicar motif amino acid sequence AHLENEVARLKK (SEQ ID NO: 01) and are thereafter complexable with the anti-helicar motif amino acid sequence monoclonal antibody. In addition to the high affinity complexation, covalent conjugation is enabled with a cysteine variant of SEQ ID NO: 01 containing a cysteine and a modified anti-helicar motif amino acid sequence antibody containing a cysteine in the CDRs via formation a stable disulfide bond. Recombinant proteins expressed by different system can be conjugated afterwards in vitro without particular reactions conditions but via spontaneous disulfide bridge shuffling.

Antibody Affinity

In certain embodiments, the anti-helicar motif amino acid sequence antibody as reported herein itself or the anti-helicar motif amino acid sequence antibody in the complex as reported herein has a dissociation constant (Kd) of ≤1 μM, ≤100 nM, ≤about 10 nM (e.g. of about $10^{-6}$M or less, e.g. from about $10^{-6}$M to about $10^{-13}$ M, e.g., from about $10^{-8}$M to about $10^{-10}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes.

Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/ml (about 0.2 μM) before injection at a flow rate of 5 μl/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Antibody Fragments

In certain embodiments, an anti-helicar motif amino acid sequence antibody provided herein or in a conjugate as reported herein is an anti-helicar motif amino acid sequence antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 93/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

Chimeric and Humanized Antibodies

In certain embodiments, an anti-helicar motif amino acid sequence antibody provided herein or the anti-helicar motif amino acid sequence antibody in a conjugate as reported herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

Library-Derived Antibodies

Anti-helicar motif amino acid sequence antibodies of the invention or anti-helicar motif amino acid sequence antibodies in the conjugate as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

Antibody Formats

The above outlined anti-helicar motif amino acid sequence antibodies and anti-helicar motif amino acid sequence antibody fragments can be combined in multiple ways to generate different antibody formats.

For example, one or more scFv antibody fragments can be fused to the C-terminus of one or more polypeptide chains of a complete antibody. Especially to each heavy chain C-terminus or to each light chain C-terminus a scFv antibody fragment can be fused.

For example, one or more antibody Fab fragments can be fused to the C-terminus of one or more polypeptide chains of a complete antibody. Especially to each heavy chain C-terminus or to each light chain C-terminus an antibody Fab fragment can be fused.

For example, one scFv and one antibody Fab fragment can be fused to the N-termini of an antibody Fc-region.

For example one scFv or antibody Fab fragment can be fused to an N-terminus of an antibody Fc-region and one scFv or antibody Fab fragment can be fused to the C-terminus of the respective other chain of an antibody Fc-region.

Multispecific Antibodies

A wide variety of recombinant antibody formats have been developed, e.g. tetravalent bispecific antibodies by fusion of, e.g., an IgG antibody format and single chain domains (see e.g. Coloma, M. J., et al., Nature Biotech 15 (1997) 159-163; WO 01/077342; and Morrison, S. L., Nature Biotech 25 (2007) 1233-1234).

Also several other formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N. and Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent FV antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multi specific and multivalent antigen-binding polypeptides are reported in WO 97/001580. WO 92/004053 reports homoconjugates, typically prepared from monoclonal antibodies of the IgG class which bind to the same antigenic determinant are covalently linked by synthetic cross-linking. WO 91/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multi-valent carriers of bi-specific antibodies, i.e., each molecule of a targetable construct can serve as a carrier of two or more bi-specific antibodies. Genetically engineered bispecific tetravalent antibodies are reported in WO 95/009917. In WO 2007/109254 stabilized binding molecules that consist of or comprise a stabilized scFv are reported.

In certain embodiments, an anti-helicar motif amino acid sequence antibody provided herein or the anti-helicar motif amino acid sequence antibody in a conjugate as reported herein is a multispecific antibody, e.g. a bispecific antibody. Multispecific antibodies are monoclonal antibodies that have binding specificities for at least two different sites. In certain embodiments, one of the binding specificities is for a helicar motif amino acid sequence and the other is for any other (non-helicar motif amino acid sequence) antigen. Bispecific antibodies may also be used to localize cytotoxic agents to cells. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

In one embodiment the CH3 domains of the heavy chains of the bispecific antibody are altered by the "knob-into-holes" technology which is described in detail with several examples in e.g. WO 96/027011, WO 98/050431, Ridgway J. B., et al., Protein Eng. 9 (1996) 617-621, Merchant, A. M., et al., Nat Biotechnol 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681, Atwell, S., et al. J. Mol. Biol. 270 (1997) 26-35) and increases the yield.

In one embodiment of all aspects the bispecific antibody is characterized in that
the CH3 domain of one heavy chain and the CH3 domain of the other heavy chain each meet at an interface which comprises an original interface between the antibody CH3 domains,
wherein said interface is altered to promote the formation of the bispecific antibody, wherein the alteration is characterized in that
a) the CH3 domain of one heavy chain is altered,
so that within the original interface the CH3 domain of one heavy chain that meets the original interface of the CH3 domain of the other heavy chain within the bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus, the bispecific antibodies as reported herein are in one embodiment characterized in that
the CH3 domain of the first heavy chain of the full length antibody and the CH3 domain of the second heavy chain of the full length antibody each meet at an interface which comprises an alteration in the original interface between the antibody CH3 domains,
wherein i) in the CH3 domain of the first heavy chain
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and wherein ii) in the CH3 domain of the second heavy chain
an amino acid residue is replaced with an amino acid residue having a smaller side chain volume, thereby generating a cavity within the interface of the second CH3 domain within which a protuberance within the interface of the first CH3 domain is positionable.

In one embodiment the amino acid residue having a larger side chain volume is selected from the group consisting of arginine (R), phenylalanine (F), tyrosine (Y), tryptophane (W).

In one embodiment the amino acid residue having a smaller side chain volume is selected from the group consisting of alanine (A), serine (S), threonine (T), valine (V).

In one embodiment both CH3 domains are further altered by the introduction of cysteine (C) as amino acid in the corresponding positions of each CH3 domain such that a disulfide bridge between both CH3 domains can be formed.

In one embodiment the bispecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C mutation into the CH3 domain of the "knobs chain" and a E356C mutation or a S354C mutation into the CH3 domain of the "hole chain" (numbering according to the EU index of Kabat et al., Sequences of Proteins of Immunological Interest, 5th ed., Public Health Service, National Institutes of Health, Bethesda, Md. (1991)).

In one embodiment the bispecific antibody comprises Y349C, T366W mutations in one of the two CH3 domains and E356C, T366S, L368A, Y407V mutations in the other of the two CH3 domains. In one embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering according to EU index of Kabat; (Kabat, E. A., et al., Sequences of Proteins of Immunological Interest, 5th ed., Public Health Service, National Institutes of Health, Bethesda, Md. (1991))). Further knobs-in-holes technologies as described by EP 1 870 459 A1, can be used alternatively or additionally. Thus another example for the bispecific antibody are R409D, K370E mutations in the CH3 domain of the "knobs chain" and D399K, E357K mutations in the CH3 domain of the "hole chain" (numbering according to EU index of Kabat; (Kabat, E. A., et al., Sequences of Proteins of Immunological Interest, 5th ed., Public Health Service, National Institutes of Health, Bethesda, Md. (1991)).

In one embodiment the bispecific antibody comprises a T366W mutation in the CH3 domain of the "knobs chain" and T366S, L368A, Y407V mutations in the CH3 domain of the "hole chain" and additionally R409D, K370E mutations in the CH3 domain of the "knobs chain" and D399K, E357K mutations in the CH3 domain of the "hole chain".

In one embodiment the bispecific antibody comprises Y349C, T366W mutations in one of the two CH3 domains and S354C, T366S, L368A, Y407V mutations in the other of the two CH3 domains or the bispecific antibody comprises Y349C, T366W mutations in one of the two CH3 domains and S354C, T366S, L368A, Y407V mutations in the other of the two CH3 domains and additionally R409D, K370E mutations in the CH3 domain of the "knobs chain" and D399K, E357K mutations in the CH3 domain of the "hole chain". Such knob and hole mutations in the CH3 domain are typically used in human heavy chain constant regions of SEQ ID NO: 08, SEQ ID NO: 09, SEQ ID NO: 10, or SEQ ID NO: 11 (human IgG1 subclass allotypes (Caucasian and Afro-American or mutants L234A/L235A, and L234A/L235A/P329G), SEQ ID NO: 12, SEQ ID NO: 13, or SEQ ID NO: 14 (human IgG4 subclass or mutants S228P, L235E, and S228P/L235E/P329G) (numbering according to the EU index of Kabat et al., Sequences of Proteins of Immunological Interest, 5th ed., Public Health Service, National Institutes of Health, Bethesda, Md. (1991).

In one embodiment the bispecific antibody comprises human heavy chain constant regions of SEQ ID NO: 08, SEQ ID NO: 09, SEQ ID NO: 10, or SEQ ID NO: 11, SEQ ID NO: 12, SEQ ID NO: 13, or SEQ ID NO: 14 further including such "knob" and "hole" mutations in the CH3 domain (e.g. Y349C, T366W mutations in one of the two CH3 domains and S354C, T366S, L368A, Y407V mutations in the other of the two CH3 domains) (numbering according to the EU index of Kabat et al., Sequences of Proteins of Immunological Interest, 5th ed., Public Health Service, National Institutes of Health, Bethesda, Md. (1991).

In one embodiment the bispecific antibody comprises human light chain constant regions of SEQ ID NO: 15 or SEQ ID NO: 16.

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to a helicar motif amino acid sequence as well as another, different antigen (see US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one embodiment the first binding specificity of the bispecific antibody is to a helicar motif amino acid sequence and the second binding specificity is to a non-helicar motif amino acid sequence antigen. In one embodiment the non-helicar motif amino acid sequence antigen is selected from the leukocyte markers, CD2, CD3, CD4, CD5, CD6, CD7, CD8, CD11a,b,c, CD13, CD14, CD18, CD19, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CD56, CD58, CD69, CD72, CTLA-4, LFA-1 and TCR; the histocompatibility antigens, MHC class I or II, the Lewis Y antigens, SLex, SLey, SLea, and SLeb; the integrins, VLA-1, VLA-2, VLA-3, VLA-4, VLA-5, VLA-6, $\alpha V\beta 3$, and LFA-1, Mac-1, and p150,95, $\alpha V\beta 1$, gpIIbIIIa $\alpha R \beta 3$, $\alpha 6\beta 4$, $\alpha V\beta 5$, $\alpha V\beta 6$, and $\alpha V$ 62 7; the selectins, L-selectin, P-selectin, and E-selectin and their counter receptors VCAM-1, ICAM-1, ICAM-2, and LFA-3; the interleukins, IL-1, IL-2, IL-3, IL-4, IL-5, IL-6, IL-7, IL-8, IL-9, IL-10, IL-11, IL-12, IL-13, IL-14, and IL-15; the interleukin receptor is selected from the group consisting of IL-1R, IL-2R, IL-3R, IL-4R, IL-5R, IL-6R, IL-7R, IL-8R, IL-9R, IL-10R, IL-11R, IL-12R, IL-13R, IL-14R, and IL-15R; the chemokine is selected from the group consisting of PF4, RANTES, MIP1$\alpha$, MCP1, NAP-2, Gro$\alpha$, Gro$\beta$, and IL-8; the growth factor is selected from the group consisting of TNFalpha, TGFbeta, TSH, VEGF/VPF, VEGFA, VEGFB, VEGF111, VEGF121, VEGF165, VEGF189, VEGF206, PTHrP, EGF family, PDGF family, endothelin, Fibrosin (FSF-1), human Laminin, and gastrin releasing peptide (GRP), PLGF, HGH, HGHR; the growth factor receptor is selected from the group consisting of TNFalphaR, RGFbetaR, TSHR, VEGFR/VPFR, EGFR, PTHrPR, PDGFR family, EPO-R, GCSF-R and other hematopoietic receptors; the interferon receptor is selected from the group consisting of IFNC$\alpha$R, IFN$\beta$R, and IFN$\lambda$R; the Ig and its receptor is selected from the group consisting of IgE, Fc$\gamma$RI, and Fc$\gamma$RII; the tumor antigen is selected from the group consisting of her2-neu, mucin, CEA and endosialin; the allergen is selected from the group consisting of house dust mite antigen, lol p1 (grass) antigens, and urushiol; the viral polypeptide is selected from the group consisting of CMV glycoproteins B, H, and gCIII, HIV-1 envelope glycoproteins, RSV envelope glycoproteins, HSV envelope glycoproteins, HPV envelope glycoproteins, Hepatitis family surface antigens; the toxin is selected from the group consisting of *pseudomonas* endotoxin and osteopontin/uropontin, snake venom, spider venom, and bee venom conotoxin; the blood factor is selected from the group consisting of complement C3b, complement C4a, complement C4b-9, Rh factor, fibrinogen, fibrin, and myelin associated growth inhibitor; and the enzyme is selected from the group consisting of cholesterol ester transfer polypeptide, membrane bound matrix metalloproteases, and glutamic acid decarboxylase (GAD).

Antibody Variants

In certain embodiments, amino acid sequence variants of the antibodies provided herein are contemplated. For example, it may be desirable to improve the binding affinity and/or other biological properties of the anti-helicar motif amino acid sequence antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. Heavy chain CDR3 and light chain CDR3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein or comprised in a conjugate as reported herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 3), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371, 826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Helicar Motif Amino Acid Sequence Containing Compounds

The helicar motif amino acid sequence in a conjugate as reported herein may be conjugated to a therapeutic agent (drug), a cytotoxic agent (e.g. a toxin such as doxorubicin or pertussis toxin), a fluorophores such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent. Such a conjugate is denoted as helicar motif containing compound. The conjugation can be either directly or via an intervening linker.

a) Therapeutic Agent

The therapeutic agent (drug) of the conjugate can be any compound, moiety or group which has a cytotoxic or cytostatic effect. Drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary therapeutic agents include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *momordica charantia* inhibitor, curcin, crotin, *sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The helicar motif amino acid sequence containing compound can be a helicar motif amino acid sequence containing compound containing an additional label moiety. Any label moiety which can be covalently attached to the helicar motif amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a helicar motif amino acid sequence and containing a label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a helicar motif amino acid sequence containing label. The helicar motif amino acid sequence will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The helicar motif amino acid sequence can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the helicar motif amino acid sequence using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al. "Methods for the Preparation of Enzyme-Antibody Conjugates for use in Enzyme Immunoassay", in Methods in Enzym. (ed. by J. Langone & I T Van Vunakis), Academic Press, New York, 73 (1981) 147-166.

Examples of enzyme-substrate combinations (U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al Nuclear Medicine and Biology, 37(3) (2010) 289-297; Chen et al, Bioconjugate Chem. 15

(2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tscheshe, Ed., Walter DeGruyter, Berlin and New York; and Wong (1991) Chemistry of Protein Conjugation and Crosslinking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

Antibody Conjugates

The antibody in a conjugate as reported herein may be further conjugated, if it is not by itself one of the molecules, to a therapeutic agent (drug), a cytotoxic agent (e.g. a toxin such as doxorubicin or pertussis toxin), a fluorophores such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Immunoconjugates

The invention also provides immunoconjugates comprising an antibody as reported herein or a conjugate as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein or a complex as reported herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein or a complex as reported herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

Linker

The term "linker" denotes a bifunctional or multifunctional moiety which can be used to conjugate (link) the antibody or helicar motif amino acid sequence to other compounds, such as detectable labels or drugs. Helicar motif amino acid sequence conjugates can be conveniently prepared using a linker having reactive functionality for binding to the further compound and to the helicar motif amino acid sequence.

In one embodiment, a linker has a reactive site which has an electrophilic group that is reactive to a nucleophilic group present on the helicar motif amino acid sequence or the antibody or the further compound. A cysteine thiol group for example is reactive with an electrophilic group on a linker and forms a covalent bond to a linker. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, alpha-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

The linker may comprise amino acid residues which link the antigen (helicar motif amino acid sequence) to the payload. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or β-amino acids, such as e.g. β-alanine, or ω-amino acids such as 4-aminobutyric acid.

In another embodiment, the linker has a reactive functional group which has a nucleophilic group that is reactive to an electrophilic group present on the helicar motif amino acid sequence or the antibody (anti-helicar motif amino acid sequence antibody).

Useful electrophilic groups include, but are not limited to, aldehyde and ketone carbonyl groups. The heteroatom of a nucleophilic group of a linker can react with an electrophilic group on the helicar motif amino acid sequence or the antibody and form a covalent bond to an antigen (helicar motif amino acid sequence) or the antibody. Useful nucleophilic groups on a linker include, but are not limited to, hydrazide, oxime, amino, hydrazine, thiosemicarbazone, hydrazine carboxylate, and arylhydrazide. The electrophilic group on an antigen (helicar motif amino acid sequence) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate ($SO_3^-$) or ammonium or a polymer such as PEG, may increase water solubility of the reagent and facilitate the coupling reaction of the linker reagent with the antigen (helicar motif amino acid sequence) or the drug moiety, or facilitate the coupling reaction depending on the synthetic route employed.

The conjugates comprising a drug or label as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)$_3$, and BM(PEO)$_4$, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys(Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and helicar motif containing compounds including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a helicar motif containing compound include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

III. Nucleic Acid

The DNA encoding the amino acid sequence of the antibody as reported herein or of the compounds or part of the compounds as comprised in a conjugate as reported herein can be prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide.

Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such modified engineered antibodies. General guidance can be found in Sambrook et al., Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

IV. Expression and Purification

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody as reported herein, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals, N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

V. Methods and Compositions for Diagnostics and Detection

In certain embodiments, any of the antibodies, especially the bispecific antibodies, and conjugates as reported herein is useful for detecting the presence of one or more target molecules in a biological sample. The term "detecting" as used herein encompasses quantitative or qualitative detection. In one embodiment a biological sample comprises a cell or tissue.

In one embodiment, an antibody or conjugate as reported herein for use in a method of diagnosis or detection is provided. In certain embodiments, the method comprises contacting the biological sample with an antibody or conjugate as reported herein under conditions permissive for binding of the antibody or the conjugate to the target, and detecting whether a complex is formed between the antibody or the conjugate and the target. Such method may be an in vitro or in vivo method.

In certain embodiments, labeled antibodies or conjugates are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

VI. Pharmaceutical Formulations

Pharmaceutical formulations of an antibody or conjugate as reported herein are prepared by mixing such antibody or conjugate having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody or conjugate, which matrices are in the form of shaped articles, e.g. films, or microcapsules.

The formulations to be used for in vivo administration are generally sterile. Sterility may be readily accomplished, e.g., by filtration through sterile filtration membranes.

VII. Therapeutic Methods and Compositions

Any of the antibodies or conjugates reported herein may be used in therapeutic methods.

In one aspect, an antibody or a conjugate as reported herein for use as a medicament is provided. In further aspects, an antibody or a conjugate as reported herein for use in treating a disease is provided. In certain embodiments, an antibody or a conjugate as reported herein for use in a method of treatment is provided. In certain embodiments, the invention provides an antibody or a conjugate as reported herein for use in a method of treating an individual comprising administering to the individual an effective amount of the antibody or the conjugate as reported herein. In one such embodiment, the method further comprises administering to the individual an effective amount of at least one additional therapeutic agent, e.g., as described below. An "individual" according to any of the above embodiments may be a human.

In a further aspect, the invention provides for the use of an antibody or a conjugate as reported herein in the manufacture or preparation of a medicament. In one embodiment, the medicament is for treatment of a disease. In a further embodiment, the medicament is for use in a method of treating a disease comprising administering to an individual having a disease an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a disease. In one embodiment, the method comprises administering to an individual having such a disease an effective amount of an antibody or a conjugate as reported herein. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the antibodies or conjugates as reported herein, e.g., for use in any of the above therapeutic methods. In one embodiment, a pharmaceutical formulation comprises any of the antibodies or conjugates as reported herein and a pharmaceutically acceptable carrier. In another embodiment, a pharmaceutical formulation comprises any of the antibodies or conjugates as reported herein and at least one additional therapeutic agent, e.g., as described below.

Antibodies and conjugates as reported herein can be used either alone or in combination with other agents in a therapy.

For instance, an antibody or conjugate as reported herein may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies and conjugates as reported herein can also be used in combination with radiation therapy.

An antibody or conjugate as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or conjugates as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or conjugate need not be, but is optionally formulated with one or more agents currently used to prevent or treat the disorder in question. The effective amount of such other agents depends on the amount of antibody or conjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or conjugate as reported herein (when used alone or in combination with one or more other additional therapeutic agents) will depend on the type of disease to be treated, the type of antibody or conjugate, the severity and course of the disease, whether the antibody or conjugate is administered for preventive or therapeutic purposes, previous therapy, the patient's clinical history and response to the antibody or conjugate, and the discretion of the attending physician. The antibody or conjugate is suitably administered to the patient at one time or over a series of treatments. Depending on the type and severity of the disease, about 1 µg/kg to 15 mg/kg (e.g. 0.5 mg/kg-10 mg/kg) of antibody or conjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or conjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an antibody or a conjugate as reported herein.

VIII. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or a complex as reported herein. The label or package insert indicates that the composition is used for treating the condition of choice. Moreover, the article of manufacture may comprise (a) a first container with a composition contained therein, wherein the composition comprises an antibody or a complex as reported herein; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an antibody or a conjugate as reported herein.

IX. Specific Embodiments

1. A conjugate comprising a helicar motif amino acid sequence containing compound and an antibody that specifically binds to the helicar motif amino acid sequence characterized by a covalent bond between the helicar motif amino acid sequence containing compound and an amino acid residue in the CDR2 of the anti-helicar antibody, whereby the CDR2 is determined according to Kabat.

2. A conjugate comprising a helicar motif amino acid sequence containing compound and an antibody that specifically binds to the helicar motif amino acid sequence of the helicar motif amino acid sequence containing compound (anti-helicar motif amino acid sequence antibody) characterized by a covalent bond between the helicar motif amino acid sequence containing compound and an amino acid residue in the CDR2 of the antibody, whereby the CDR2 is determined according to Kabat.
3. The conjugate according to any one of items 1 to 2, characterized in that the CDR2 is the light chain CDR2.
4. The conjugate according to any one of items 1 to 3, characterized in that the helicar motif amino acid sequence has the amino acid sequence AHLENEVARLKK (SEQ ID NO: 01) or is a variant thereof with one amino acid residue changed to cysteine.
5. The conjugate according to any one of items 1 to 4, characterized in that the helicar motif amino acid sequence has the amino acid sequence AHLENEVARLKK (SEQ ID NO: 01) wherein one amino acid residue of the three C-terminal amino acid residues is changed to cysteine.
6. The conjugate according to any one of items 1 to 5, characterized in that the helicar motif amino acid sequence has the amino acid sequence of AHLENEVARCKK (SEQ ID NO: 02) or AHLENEVARLCK (SEQ ID NO: 03).
7. The conjugate according to any one of items 1 to 6, characterized in that the helicar motif amino acid sequence containing compound comprises a helicar motif amino acid sequence, optionally a linker, and a payload.
8. The conjugate according to any one of items 1 to 7, characterized in that the helicar motif amino acid sequence containing compound is a polypeptide comprising the helicar motif amino acid sequence either fused to one of its termini or within the polypeptide sequence.
9. The conjugate according to any one of items 1 to 8, characterized in that the covalent bond is between the helicar motif amino acid sequence containing compound and an amino acid residue in the CDR2 of the antibody.
10. The conjugate according to any one of items 1 to 9, characterized in that the covalent bond is between a functional group in the helicar motif amino acid sequence containing compound and the amino acid residue in the CDR2 of the antibody.
11. The conjugate according to any one of items 1 to 10, characterized in that the functional group is in the helicar motif amino acid sequence.
12. The conjugate according to any one of items 1 to 11, characterized in that the covalent bond is between a cysteine residue in the light chain CDR2 of the antibody and a functional group in the helicar motif amino acid sequence containing compound.
13. The conjugate according to item 12, characterized in that the cysteine residue in the light chain CDR2 of the antibody is at position 55 or position 51 according to the light chain variable domain numbering of Kabat.
14. The conjugate according to any one of items 12 to 13, characterized in that the cysteine residue in the light chain CDR2 of the antibody is at position 55 according to the light chain variable domain numbering of Kabat.
15. The conjugate according to any one of items 1 to 14, characterized in that the covalent bond is a disulfide bond.
16. The conjugate according to item 15, characterized in that the disulfide bond is between a cysteine residue in the helicar motif amino acid sequence and a cysteine residue in the CDR2 of the light chain of the anti-helicar antibody.
17. The conjugate according to any one of items 1 to 16, characterized in that the helicar motif amino acid sequence has the amino acid sequence of SEQ ID NO: 02.
18. The conjugate according to any one of items 1 to 17, characterized in that the antibody is a bispecific antibody comprising a first binding specificity to a non-helicar antigen and a second binding specificity to helicar motif amino acid sequence.
19. The conjugate according to item 18, characterized in that the (non-helicar) antigen is a cell surface antigen.
20. The conjugate according to item 19, characterized in that the cell surface antigen is a tumor associated antigen.
21. The conjugate according to any one of items 18 to 20, characterized in that the bispecific antibody is a full length antibody to which at one or both heavy chain C-termini a scFv or a dsscFv or a scFab or a dsscFab or a combination thereof has been fused either directly or via a peptidic linker.
22. The conjugate according to any one of items 18 to 21, characterized in that the bispecific antibody is a full length antibody.
23. The conjugate according to any one of items 18 to 22, characterized in that one heavy chain of the bispecific antibody comprises a hole mutation and the respective other chain comprises a knob mutation.
24. The conjugate according to any one of items 7 to 23, characterized in that the payload is selected from a binding moiety, a labeling moiety, and a biologically active moiety.
25. The conjugate according to any one of items 1 to 24, characterized in that the antibody is a full length antibody.
26. The conjugate according to any one of items 1 to 25, characterized in that the antibody is a humanized or a human antibody.
27. The conjugate according to any one of items 1 to 26, characterized in that the constant region of the antibody is of the IgG1 subclass or of the IgG4 subclass.
28. The conjugate according to any one of items 1 to 27, characterized in that the antibody has a constant region of the IgG1 subclass with an alanine at position 234 and 235 and with a glycine at position 329 with numbering according to the EU index of Kabat.
29. The conjugate according to any one of items 1 to 27, characterized in that the antibody has a constant region of the IgG4 class with a proline at position 228, a glutamic acid at position 235 and a glycine at position 329 with numbering according to the EU index of Kabat.
30. The conjugate according to any one of items 1 to 24, characterized in that embodiment the antibody is an antibody fragment.
31. The conjugate according to item 30, characterized in that the fragment is a Fab or a $(Fab)_2$.
32. The conjugate according to any one of items 1 to 31, characterized in that the conjugate comprises exactly one covalent bond per light chain CDR2.
33. The conjugate according to any one of items 1 to 32, characterized in that the helicar motif amino acid sequence containing compound comprises a reactive group that can form a covalent bond with the thiol group of the cysteine residue in the CDR2 of the antibody.
34. The conjugate according to any one of items 1 to 33, characterized in that the reactive group is a thiol, or a maleimide, or a haloacetyl.
35. The conjugate according to any one of items 1 to 34, characterized in that the covalent bond is a disulfide bond.

36. The conjugate according to item 35, characterized in that the disulfide bond is formed without the addition of a redox active agent.
37. The conjugate according to any one of items 1 to 36, characterized in that the conjugate comprises a therapeutic or detectable moiety.
38. The conjugate according to item 37, characterized in that the therapeutic or detectable moiety is covalently conjugated to helicar motif amino acid sequence or the helicar motif amino acid sequence is incorporated into the therapeutic or detectable moiety.
39. The conjugate according to any one of items 1 to 38, characterized in that the helicar motif amino acid sequence is conjugated to a polypeptide consisting of 5 to 500 amino acid residues.
40. The conjugate according to item 39, characterized in that the polypeptide comprises 10 to 450 amino acid residues.
41. The conjugate according to any one of items 39 to 40, characterized in that the polypeptide comprises 12 to 450 amino acid residues.
42. The conjugate according to any one of items 39 to 41, characterized in that the polypeptide comprises 15 to 400 amino acids residues.
43. The conjugate according to any one of items 1 to 42, characterized in that the helicar motif amino acid sequence is conjugated to a detectable label.
44. The conjugate according to any one of items 1 to 43, characterized in that the helicar motif amino acid sequence is conjugated to the polypeptide, or to the detectable label, or to the payload via a linker.
45. The conjugate according to item 44, characterized in that the linker is a non-peptidic linker.
46. The conjugate according to item 44, characterized in that the linker is a peptidic linker.
47. An anti-helicar antibody that has in the light chain a cysteine residue in the CDR2 whereby the CDRs are determined according to Kabat.
48. The anti-helicar antibody according to item 47, characterized in that the cysteine residue in the light chain CDR2 of the antibody is at position 55 or position 51 according to the light chain variable domain numbering of Kabat.
49. The anti-helicar antibody according to any one of items 47 to 48, characterized in that the cysteine residue in the light chain CDR2 of the antibody is at position 55 according to the light chain variable domain numbering of Kabat.
50. The anti-helicar antibody according to any one of items 47 to 49, characterized in that the antibody has in exactly one heavy chain variable domain a cysteine residue at position 55 or position 51.
51. The anti-helicar antibody according to any one of items 47 to 50, characterized in that the antibody is a humanized or human antibody.
52. The anti-helicar antibody according to any one of items 47 to 51, characterized in that the antibody is a full length antibody, or a Fab, or a scFv, or a scFv conjugated to an Fc-region.
53. The anti-helicar antibody according to any one of items 47 to 52, characterized in that the cysteine forms a disulfide bond with an isolated cysteine residue or an isolated homocysteine residue.
54. An immunoconjugate comprising the conjugate according to any one of items 1 to 46 and a cytotoxic agent.
55. A pharmaceutical formulation comprising the conjugate according to any one of items 1 to 46 and a pharmaceutically acceptable carrier.
56. The conjugate according to any one of items 1 to 46 for use as a medicament. 57. The conjugate according to any one of items 1 to 46 for the treatment of cancer. 58. The conjugate according to any one of items 1 to 46 for the treatment of diabetes.
59. The conjugate according to any one of items 1 to 46 for the treatment of adiposities.
60. The conjugate according to any one of items 1 to 46 for the treatment of an inflammatory disease.
61. The conjugate according to any one of items 1 to 46 for the treatment of a metabolic disease.
62. The conjugate according to any one of items 1 to 46 for the treatment of a viral disease.
63. The use of a conjugate according to any one of items 1 to 46 in the manufacture of a medicament.
64. The use of a conjugate according to any one of items 1 to 46 as diagnostic agent.
65. The use of a conjugate according to any one of items 1 to 46 comprising a therapeutic polypeptide to increase the stability of the therapeutic polypeptide.
66. The use of a conjugate according to any one of items 1 to 46 comprising a therapeutic polypeptide to increase the activity of the therapeutic polypeptide.
67. The use of a conjugate according to any one of items 1 to 46 comprising a therapeutic polypeptide to increase the in vivo half-life of the therapeutic polypeptide.
68. The use of a conjugate according to any one of items 1 to 46 in the treatment of a disease.
69. A method of treating an individual having a disease comprising administering to the individual an effective amount of a conjugate according to any one of items 1 to 46.
70. A method of treating a disease in an individual comprising administering to the individual an effective amount of the conjugate according to any one of items 1 to 46.
71. The method according to any one of items 68 to 70, characterized in that the disease is cancer.
72. The method according to any one of items 68 to 70, characterized in that the disease is diabetes.
73. The method according to any one of items 68 to 70, characterized in that the disease is adipositas.
74. A method of producing a conjugate according to any one of items 1 to 46 comprising the combination of an anti-helicar antibody comprising a first reactive group and an helicar motif amino acid sequence containing compound that has a second reactive group whereby the alpha carbon atom of the amino acid residue that bears the first reactive group is about 10 to 11 Angstrom apart from the atom of the helicar motif amino acid sequence containing compound to which the linker is fused.
75. A method of producing a conjugate according to any one of items 1 to 46 comprising the steps of
   combining in solution an anti-helicar antibody that specifically binds to a helicar motif amino acid sequence and comprises a reactive group at one amino acid residue in the CDR2 with a helicar motif amino acid sequence containing compound comprising a reactive group, wherein the helicar motif amino acid sequence containing compound comprises a payload, such as a peptide consisting of 5 to 500 amino acids or a detectable label, and
   recovering of the conjugate from the solution.
76. A method for producing an anti-helicar antibody for the formation of a conjugate according to any one of items 1 to 46, comprising the step of cultivating a cell comprising a nucleic acid encoding the anti-helicar antibody, and recovering the anti-helicar antibody from the cell or the cultivation medium, wherein in the anti-helicar antibody the residue in the light chain CDR2 is mutated to cysteine that has in the X-ray structure of the non-covalent complex of the anti-helicar antibody and the helicar motif amino acid sequence containing compound a distance of 10 to 11 Angstrom between the alpha-carbon atom of the amino acid residue in the antibody CDR2 and the atom of the helicar motif amino acid sequence containing compound atom between which the covalent bond is to be formed.

77. A method for identifying a position in an anti-helicar antibody CDR2 that can be mutated to cysteine for the formation of a covalent bond between the residue in the antibody CDR2 and the bound helicar motif amino acid sequence containing compound comprising the step of providing a crystal structure of the non-covalent complex of the anti-helicar antibody and the helicar motif amino acid sequence containing compound, and identifying an amino acid residue in the CDR2 of the anti-helicar antibody and in the helicar motif amino acid sequence containing compound with a distance of 10 to 11 Angstrom between the alpha-carbon atoms of the amino acid residue in the antibody CDR2 and the atom in the helicar motif amino acid sequence containing compound, wherein the identified position is the position in an antibody CDR2 that can be mutated to cysteine for the formation of a covalent bond between the residue in the antibody CDR2 and the bound helicar motif amino acid sequence containing compound.

78. A bispecific anti-helicar antibody for targeted delivery of a helicar motif amino acid sequence containing compound to a target cell, wherein the bispecific antibody comprises a first binding site that specifically binds to the helicar motif amino acid sequence containing compound and a second binding specificity that specifically binds to a cell surface marker of the target cell.

The disclosure of all references cited herein is herewith incorporated by reference.

The following examples, figures and sequences are provided to aid the understanding of the present invention, the true scope of which is set forth in the appended claims. It is understood that modifications can be made in the procedures set forth without departing from the spirit of the invention.

EXAMPLES

For the amino acid sequences, synthesis and purification of the anti-hapten antibodies and haptenylated compounds as used in the examples below please see WO 2014/006124.

Example 1

Binding of Recombinant Humanized Anti-Biotin Antibody to Biotin-Labeled Compound (Haptenylated Compound)

In order to determine whether the humanization procedure and the subsequent introduction of cysteine mutations resulted in derivatives that had retained full binding activity the following experiments were performed.

The binding properties of the recombinant anti-biotin antibody derivatives were analyzed by biolayer interferometry (BLI) technology using an Octet QK instrument (Fortebio Inc.). This system is well established for the study of molecule interactions. BLi-technology is based on the measurement of the interference pattern of white light reflected from the surface of a biosensor tip and an internal reference. Binding of molecules to the biosensor tip is resulting in a shift of the interference pattern which can be measured. To analyze if the humanization procedure described above diminished the ability of the anti-biotin antibody to bind to biotin, the properties of the chimeric and the humanized versions of the antibody in their ability to bind to a biotinylated protein were compared directly. Binding studies were performed by capturing anti-biotin antibody on anti-huIgG Fc antibody Capture (AHC) Biosensors (Fortebio Inc.). First, biosensors were incubated in an antibody solution with a concentration of 0.5 mg/ml in 20 mM histidine, 140 mM NaCl, pH 6.0 for 1 min. Thereafter, the biosensors were incubated for 1 min. in 1×PBS pH 7.4 to reach a stable baseline. Binding was measured by incubating the antibody-coated biosensors in a solution containing biotinylated protein with a concentration of 0.06 mg/ml in 20 mM histidine, 140 mM NaCl, pH 6.0 for 5 min. Dissociation was monitored for 5 min. in 1×PBS pH 7.4. The resulting binding curves for chimeric and humanized anti-biotin antibodies were compared directly.

The humanized version of the antibody showed equal or even better binding of the biotinylated antigen than the chimeric antibody. The same is true for the humanized antibody with the Cys mutation at Kabat position VH53. The biotinylated protein showed residual unspecific binding to the biosensors which was reduced when the biosensors were coated with Herceptin, which does not bind biotin. Thus, the functionality of the anti-biotin antibody was retained in its humanized variant (which is defined by the sequences as depicted in SEQ ID NO: 19 and 20, SEQ ID NO: 21 and 22).

Surface Plasmon Resonance

Surface plasmon resonance measurement was performed on a BIAcore® T200 instrument (GE Healthcare Biosciences AB, Sweden) at 25° C. Around 4300 resonance units (RU) of the capturing system (10 µg/ml Anti-human Capture (IgG Fc) from Human Antibody Capture Kit, BR-1008-39, GE Healthcare Biosciences AB, Sweden) were coupled on a CM3 chip (GE Healthcare, BR-1005-36) at pH 5.0 by using the standard amine coupling kit supplied by GE Healthcare (BR-1000-50). The running buffer for amine coupling was HBS-N (10 mM HEPES, pH 7.4, 150 mM NaCl, GE Healthcare, BR-1006-70). Running and dilution buffer for the followed binding study was PBS-T (10 mM phosphate buffered saline including 0.05% Tween 20) pH 7.4. The humanized anti-biotin antibody was captured by injecting a 2 nM solution for 60 sec at a flow rate of 5 Biotinylated siRNA was diluted with PBS-T at concentrations of 0.14-100 nM (1:3 dilution series). Binding was measured by injecting each concentration for 180 sec at a flow rate of 30 µl/min, dissociation time 600 sec. The surface was regenerated by 30 sec washing with a 3 M $MgCl_2$ solution at a flow rate of 5 The data were evaluated using BIAevaluation software (GE Healthcare Biosciences AB, Sweden). Bulk refractive index differences were corrected by subtracting the response obtained from an anti-human IgG Fc surface. Blank injections were also subtracted (=double referencing). For calculation of KD and kinetic parameters the Langmuir 1:1 model was used.

Kinetic binding analysis by surface plasmon resonance (SPR) was carried out for humanized anti-biotin antibody SEQ ID NO: 19 and 20 and humanized anti-biotin antibody VH53C SEQ ID NO: 21 and 22. Anti-biotin antibodies at a concentration of 2 nM were captured by anti-human IgG Fc antibody which was bound to a CM3 sensor chip. Binding of biotinylated siRNA (Mw: 13868 Da) was recorded at the concentrations 0.41, 1.23, 3.7, 11.1, 33.3, 100 and 300 nM. Measurements were carried out in duplicates. The calculated $K_D$ for humanized anti-biotin antibody and humanized anti-biotin antibody VH53C were 0.633 nM and 0.654 nM, respectively.

Example 2

Generation of Non-Covalent Complexes of Haptenylated Compounds with Anti-Hapten Antibodies General Method:

The generation of complexes of anti-hapten antibodies with haptenylated compounds (=haptens conjugated to a payload) shall result in defined complexes and it shall be assure that the compound (=payload) in these complexes retains its activity. For the generation of complexes of haptenylated compounds with the respective anti-hapten antibody the haptenylated compound was dissolved in $H_2O$ to a final concentration of 1 mg/ml. The antibody was concentrated to a final concentration of 1 mg/ml (4.85 µM) in 20 mM histidine buffer, 140 mM NaCl, pH=6.0. Haptenylated payload and antibody were mixed to a 2:1 molar ratio (compound to antibody) by pipetting up and down and incubated for 15 minutes at RT.

Alternatively, the haptenylated compound was dissolved in 100% DMF to a final concentration of 10 mg/ml. The antibody was concentrated to a final concentration of 10 mg/ml in 50 mM Tris-HCl, 1 mM EDTA, pH 8.2. Haptenylated compound and antibody were mixed to a 2.5:1 molar ratio (compound to antibody) by pipetting up and down and incubated for 60 minutes at RT and 350 rpm.

Exemplary Method for the Formation of Complexes of Haptenylated Fluorescent Dyes and Anti-Hapten Antibodies—Non-Covalent Digoxigenin-Cy5 Complex Humanized and murine anti-digoxigenin antibody or bispecific anti-digoxigenin antibody derivatives were used as antibody components. For the generation of complexes of digoxigenylated Cy5 with the anti-digoxigenin antibodies the Cy5-digoxigenin conjugate was dissolved in PBS to a final concentration of 0.5 mg/ml. The antibody was used in a concentration of 1 mg/ml (about 5 µM) in a buffer composed of 20 mM histidine and 140 mM NaCl, pH 6. Digoxigenylated Cy5 and antibody were mixed at a 2:1 molar ratio (digoxigenylated Cy5 to antibody). This procedure resulted in a homogenous preparation of complexes of defined composition.

The complexation reaction can be monitored by determining the fluorescence (650/667 nm) of the antibody-associated fluorophore on a size exclusion column. The results of these experiments demonstrate that complexation only occurs if the antibody contains binding specificities for digoxigenin. Antibodies without binding specificities for digoxigenin do not bind the digoxigenin-Cy5 conjugate. An increasing signal can be observed for bivalent anti-digoxigenin antibodies until a digoxigenin-Cy5 conjugate to antibody ratio of 2:1. Thereafter, the composition dependent fluorescence signals reach a plateau.

Exemplary Method for the Formation of Complexes of Haptenylated Fluorescent Dyes and Anti-Hapten Antibodies—Biotin-Cy5/Chimeric Anti-Biotin Antibody (Human IgG Subclass) Complex For the generation of complexes of biotin-derivatized-Cy5 (Biotin-Cys-Cy5) containing a cysteinylated linker, 0.16 mg of Biotin-Cys-Cy5 were dissolved in 100% DMF to a concentration of 10 mg/ml. 1 mg of the antibody was used in a concentration of 10.1 mg/ml (about 69 µM) in a buffer composed of 50 mM Tris-HCl, 1 mM EDTA, pH 8.2. Biotin-Cys-Cy5 and antibody were mixed at a 2.5:1 molar ratio (Biotin-Cys-Cy5 to antibody) and incubated for 60 min at RT, shaken at 350 rpm. The resulting conjugate was analyzed by SDS-PAGE as described in Example 3a. Detection of fluorescence was carried out as described in Example 3a.

Exemplary Method for the Formation of Conjugates of Biotinylated Fluorescent Dyes and Anti-Biotin Antibodies—Biotin-Ser-Cy5/Humanized Anti-Biotin Antibody:

For the generation of complexes of biotin-derivatized-Cy5 (Biotin-Ser-Cy5) containing a serine residue within the linker, 0.61 mg of Biotin-Ser-Cy5 were dissolved in 20 mM histidine, 140 mM NaCl, pH 6.0 to a concentration of 10 mg/ml. 18.5 mg of the humanized anti-biotin antibody was used in a concentration of 10 mg/ml (about 69 µM) in a buffer composed of 50 mM Tris-HCl, 1 mM EDTA, pH 8.2. Biotin-Ser-Cy5 and antibody were mixed at a 2.5:1 molar ratio (Biotin-Ser-Cy5 to antibody) and incubated for 60 min at RT, shaken at 350 rpm. The sample was then subjected to size exclusion chromatography using Superdex 200 16/60 high load prep grade column (GE Healthcare) with a flow rate of 1.5 ml/min and 20 mM histidine, 140 mM NaCl, pH 6.0 as the mobile phase. Peak fractions were collected and analyzed by SDS-PAGE for purity. The dye to antibody ratio was calculated by (1) measuring the absorbance of the samples at the wavelength 280 nm (protein) and 650 nm (Cy5); (2) using the formula: $A_{650}$ of labeled protein/ε(Cy5) *protein concentration (M)=moles dye per mole protein, where ε(Cy5)=250000 $M^{-1}cm^{-1}$, $A_{650}$ of the complex=47.0 and the protein concentration is 86.67 µM. The resulting ratio of dye to antibody molecule was 2.17 which indicates that all antibody paratopes are saturated with Biotin-Cy5 molecules.

Exemplary Method for the Formation of Complexes of Haptenylated Polypeptides and Anti-Hapten Antibodies—Digoxigenin-PYY(3-36)/Anti-Digoxigenin Antibody Complex For the generation of non-covalent complexes of digoxigenylated polypeptides with an anti-digoxigenin antibody the murine hybridoma-derived antibody (lyophilisate from 10 mM $KPO_4$, 70 mM NaCl; pH 7.5) was dissolved in 12 ml water and dialyzed against a solution comprising 20 mM histidine, 140 mM NaCl, pH 6.0 to yield 300 mg ($2\times10^{-6}$ mol) in 11 ml buffer (c=27.3 mg/ml). Digoxigenin-PYY(3-36) conjugate (11.57 mg, $4\times10^{-6}$ mol, 2 eq.) was added in 4 portions of 2.85 mg within 1 h and incubated for another hour at room temperature. After completion of the complexation reaction, the complexes were purified by size exclusion chromatography via a Superdex 200 26/60 GL column (320 ml) in 20 mM histidine, 140 mM NaCl, at pH 6.0 at a flow rate of 2.5 ml/min. The eluted complex was collected in 4 ml fractions, pooled and sterilized over a 0.2 µm filter to give 234 mg of the complex at a concentration of 14.3 mg/ml. In a similar manner, for generation of complexes of the humanized anti-digoxigenin antibody the antibody was adjusted to a concentration of 10.6 mg/ml (9.81 mg, 6.5× $10^{-8}$ mol in 0.93 ml) in 20 mM histidine, 140 mM NaCl, pH 6.0. 0.57 mg=$1.97\times10^{-7}$ mol=3.03 eq. of the digoxigenylated polypeptide (DIG-PYY) were added to the antibody solution as lyophilisate. Polypeptide and antibody were incubated for 1.5 hrs. at room temperature. The excess of polypeptide was removed by size exclusion chromatography via a Superose 6 10/300 GL column in 20 mM histidine, 140 mM NaCl, at pH 6.0 at a flow rate of 0.5 ml/min. The eluted complex was collected in 0.5 ml fractions, pooled and sterilized over a 0.2 μm filter to give 4.7 mg of the complex at a concentration of 1.86 mg/ml.

The resulting haptenylated polypeptide-anti-hapten antibody complex was defined as monomeric IgG-like molecule via the occurrence of a single peak in a size exclusion chromatography. The resulting complex was defined as monomeric IgG-like molecule, carrying two Digoxigenin-PYY derivatives per antibody molecule. The defined composition of these peptide complexes was confirmed by size exclusion chromatography, which also indicated the absence of protein aggregates. The defined composition (and 2:1 polypeptide to protein ratio) of these bispecific peptide complexes was further confirmed by SEC-MALS (Size exclusion chromatography-Multi Angle Light Scattering). For SEC-MALS analysis, 100-500 μg of the respective sample was applied to a Superdex 200 10/300 GL size exclusion column with a flow rate of 0.25-0.5 ml/min with 1×PBS pH 7.4 as mobile phase. Light scattering was detected with a Wyatt MiniDawn TREOS/QELS detector, the refractive index was measured with a Wyatt Optilab rEX-detector. Resulting data was analyzed using the software ASTRA (version 5.3.4.14). The results of SEC MALLS analyses provide information about the mass, radius and size of the complex. These data were then compared with those of the corresponding non-complexed antibody. The results of these experiments demonstrate that exposure of Digoxigenylated-PYY to the anti-digoxigenin antibody results in complexes that contain two Digoxigenin-PYY derivatives per one antibody molecule. Thus, digoxigenylated PYY can be complexed with the anti-digoxigenin antibody at defined sites (binding region) and with a defined stoichiometry.

Characterization of the complex by surface plasmon resonance studies provided additional evidence that the complexation reaction generated defined and completely complexed molecules. The anti-digoxigenin antibody can be bound to the SPR chip which results in signal increases. Subsequent addition of digoxigenin-PYY conjugate results in further signal increases until all binding sites are completely occupied. At these conditions, addition of more Digoxigenin-PYY does not increase the signal further. This indicates that the complexing reaction is specific and that the signals are not caused by non-specific stickiness of the digoxigenylated polypeptide.

Exemplary Method for the Formation of Complexes of Haptenylated Polypeptides and Anti-Hapten Antibodies—Ac-PYY-PEG3-Cys-β-Ala-Biot/Chimeric Anti-Biotin Antibody Complex For the generation of non-covalent complexes of biotinylated-PYY-polypeptide containing a cysteinylated linker, 0.19 mg of Ac-PYY-PEG3-Cys-β-Ala-Biot were dissolved in 100% DMF to a concentration of 10 mg/ml. The antibody was used in a concentration of 10.7 mg/ml (about 73 μM) in a buffer composed of 50 mM Tris-HCl, 1 mM EDTA, pH 8.2. Ac-PYY-PEG3-Cys-β-Ala-Biot and antibody were mixed at a 2.5:1 molar ratio (Ac-PYY-PEG3-Cys-β-Ala-Biot to antibody) and incubated for 60 min at RT and 350 rpm. The resulting complex was defined as monomeric IgG-like molecule via the occurrence of a single peak in a size exclusion chromatography (95% monomer). The resulting complex was further analyzed by SDS-PAGE and subsequent Western Blot analysis. 10 μg of the complex were mixed with 4×LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 μm pore size, Invitrogen) for 40 min at 25V and 160 mA. The membrane was blocked in 1% (w/v) skim milk in 1×PBST (1×PBS+0.1% Tween20) for 1 h at RT. The membrane was washed 3× for 5 min in 1×PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Haptenylated Polypeptides and Anti-Hapten Antibodies—Ac-PYY-PEG3-Cys-PEG2-Biot/Chimeric Anti-Biotin Antibody Complex For the generation of non-covalent complexes of biotinylated-PYY-polypeptide containing a cysteinylated linker, 0.16 mg of Ac-PYY-PEG3-Cys-PEG2-Biot were dissolved in 100% DMF to a concentration of 10 mg/ml. The antibody was used in a concentration of 10.7 mg/ml (about 73 μM) in a buffer composed of 50 mM Tris-HCl, 1 mM EDTA, pH 8.2. Ac-PYY-PEG3-Cys-PEG2-Biot and antibody were mixed at a 2.5:1 molar ratio (Ac-PYY-PEG3-Cys-PEG2-Biot to antibody) and incubated for 60 min at RT and 350 rpm. The resulting complex was defined as 63% monomeric IgG-like molecule and 37% dimeric soluble aggregates via size exclusion chromatography. The resulting complex was further analyzed by SDS-PAGE and subsequent Western Blot analysis. 10 μg of the complex were mixed with 4×LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 μm pore size, Invitrogen) for 40 min at 25V and 160 mA. The membrane was blocked in 1% (w/v) skim milk in 1×PBST (1×PBS+0.1% Tween20) for 1 h at RT. The membrane was washed 3× for 5 min in 1×PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Haptenylated Polypeptides and Anti-Hapten Antibodies—Ac-PYY(PEG3-Cys-PEG2-5-Fluo)/Chimeric Anti-Fluorescein Antibody Complex For the generation of non-covalent complexes of fluorescein-conjugated-PYY-polypeptide containing a cysteinylated linker, 0.33 mg of Ac-PYY(PEG3-Cys-PEG2-5-Fluo were dissolved in 100% DMF to a concentration of 10 mg/ml. The antibody was used in a concentration of 9.99 mg/ml (about 68 μM) in a buffer composed of 50 mM Tris-HCl, 1 mM EDTA, pH 8.2. Ac-PYY(PEG3-Cys-PEG2-5-Fluo and antibody were mixed at a 2.5:1 molar ratio (Ac-PYY(PEG3-Cys-PEG2-5-Fluo) to antibody) and incubated for 60 min at RT and 350 rpm. The resulting complex was defined as 76% monomeric IgG-like molecule and 24% dimeric soluble aggregates via size exclusion chromatography. The resulting complex was further analyzed by SDS-PAGE and subsequent detection of fluorescein-related fluorescence in the polyacrylamide-gel. 8 μg of the complex were mixed with 4×LDS sample buffer (Invitrogen) and incubated at 95° C. for 5 min. Fluorescein-related fluorescence was recorded using a LumiImager F1 device (Roche) at an excitation wavelength of 645 nm.

Example 3

Generation of Defined Covalent Conjugates of Haptenylated Dyes or Polypeptides with an Anti-Hapten Antibody VH52bC/VH53C in the Presence of Redox Agents Exemplary Method for the Formation of Conjugates of Haptenylated Fluorescent Dyes and Anti-Hapten Antibodies—Dig-Cys-Ahx-Cy5/Anti-Digoxigenin Antibody VH52bC The generation of covalent conjugates of anti-hapten antibodies and haptenylated fluorescent dyes containing a cysteine-linker results in defined conjugates where a disulfide bridge is formed at a specific position between VH52bC in the CDR2 of the anti-hapten antibody and the cysteine in the linker between the hapten and the fluorescent dye. The conjugation reaction was carried out in the presence of redox reagents. Dig-Cys-Ahx-Cy5 was dissolved in 20 mM histidine, 140 mM NaCl, pH 6.0. Solubilization was facilitated by drop wise addition of 10% (v/v) acetic acid. The final concentration was adjusted to 0.4 mg/ml. The anti-digoxigenin antibody VH52bC in 20 mM histidine, 140 mM NaCl, pH 6.0 was brought to a concentration of 10 mg/ml. An anti-digoxigenin antibody was used as a control and was treated the same way as anti-digoxigenin antibody VH52bC. 4.7 nmol of each antibody was mixed with 2.5 molar equivalents of Dig-Cys-Ahx-Cy5. This was achieved by adding 11.7 nmol of this substance in 4 portions (2.9 nmol each) every 15 min. In between these additions, the samples were incubated at 25° C. while gently shaking. After addition of the last portion, 0.64 nmol of each antibody-Dig-Cys-Ahx-Cy5 complex was transferred to buffer containing the following redox reagents: 3 mM DTE (Dithioerythritol)+10 mM GSSG (oxidized Glutathione), 0.3 mM DTE+1 mM GSSG and 0.03 mM DTE+0.1 mM GSSG. All samples were incubated for 15 min in these conditions. After the incubation, samples were split into half (0.34 nmol each) and prepared for SDS gel electrophoresis. For this, 4×LDS sample buffer (Invitrogen) was added. For each sample also a reduced version was prepared by adding 10× NuPAGE sample reducing agent (Invitrogen). All samples were incubated at 70° C. for 5 min before electrophoresis on a 4-12% Bis-Tris polyacrylamide gel (NuPAGE, Invitrogen) with 1×MOPS buffer (Invitrogen). Cy5-related fluorescence in the gel was detected with a LumiImager F1 device (Roche) at an excitation wavelength of 645 nm. After detection of fluorescence, the gel was stained with SimplyBlue SafeStain (Invitrogen). Gels are shown in FIG. 3.

Site-specific disulfide bond formation was shown for anti-digoxigenin antibody VH52bC (FIG. 8, gels on top, lanes 1 A-C) with a low background fluorescence signal when anti-digoxigenin antibody without a cysteine in CDR2 was used (lanes 2 A-C). The background signals in the control reactions can be explained by coupling of Dig-Cys-Ahx-Cy5 to cysteines that are normally involved in the formation of antibody-interchain disulfide bonds. Increasing amounts of redox reagents substantially reduce disulfide bridges that connect antibody heavy and light chains, producing mainly ¾ antibodies (−1× LC), HC-dimers (−2× LC) and ½ antibodies (1× HC+1× LC). On the bottom of the gel fluorescence of Dig-Cys-Ahx-Cy5 that was not covalently linked to the antibody can be detected. The gels on the bottom of FIG. 8 show, that upon reduction of the samples, no Cy5-related fluorescence is detectable near the antibody heavy and light chains, indicating that the covalent linkage was indeed formed by a disulfide bridge. Coomassie stains of each gel show that the total amount of protein in each lane was equal.

Exemplary Method for the Formation of Conjugates of Haptenylated Fluorescent Dyes and Anti-Hapten Antibodies—Dig-Cvs-Cy5/Anti-Digoxigenin Antibody VH52bC Dig-Cys-Cy5 was dissolved in 8.3 mM HCl, 10% (v/v) DMF to a final concentration of 3.25 mg/ml. The anti-digoxigenin antibody VH52bC antibody in 20 mM histidine, 140 mM NaCl, pH 6.0 was brought to a concentration of 15 mg/ml. anti-digoxigenin antibody was used as a control and was treated the same way as anti-digoxigenin antibody VH52bC. 13.3 nmol of each antibody was mixed with 2 molar equivalents of Dig-Cys-Cy5 at a final antibody concentration of 10 mg/ml in the presence of 1 mM GSH (reduced glutathione) and 5 mM GSSG (reduced glutathione). This was achieved by adding 26.6 nmol of this substance in 2 portions every 5 min. In between these additions, the samples were incubated at RT while gently stirred. After addition of the last portion, the samples were incubated for 1 h at RT. The efficiency of the coupling reaction was evaluated by SDS-PAGE and subsequent recording of the Cy5-related fluorescence signal. 5, 10 and 20 µg of each sample were prepared for SDS-PAGE. For this, 4×LDS sample buffer (Invitrogen) was added. All samples were incubated at 70° C. for 5 min before electrophoresis on a 4-12% Bis-Tris polyacrylamide gel (NuPAGE, Invitrogen) with 1×MOPS buffer (Invitrogen). Cy5-related fluorescence in the gel was detected with a LumiImager F1 device (Roche) at an excitation wavelength of 645 nm. After detection of fluorescence, the gel was stained with SimplyBlue SafeStain (Invitrogen).

Exemplary Method for the Formation of Conjugates of Haptenylated Polypeptides and Anti-Hapten Antibodies—PEG3-PYY(PEG3-Cvs-4Abu-Dig)/Humanized Anti-Digoxigenin Antibody VH52bC For the generation of conjugates of digoxigenin-derivatized-PYY-polypeptide containing a cysteinylated linker, 1.4 mg of PEG3-PYY(PEG3-Cys-4Abu-Dig) were dissolved in 100% DMF to a concentration of 10 mg/ml. 1 mg of the antibody was used in a concentration of 10 mg/ml (about 68 µM) in a buffer composed of 5 mM Tris-HCl, 1 mM EDTA, 1 mM GSH, 5 mM GSSG, pH 8.2. PEG3-PYY(PEG3-Cys-4Abu-Dig) and antibody were mixed at a 2:1 molar ratio (PEG3-PYY(PEG3-Cys-4Abu-Dig) to antibody) and incubated for 60 min at RT, stirred at 100 rpm. The resulting conjugate was analyzed by mass spectrometry. 43% of the detected species was identified as antibody coupled to 2 polypeptide molecules, 46% was antibody coupled to 1 polypeptide molecule and 11% was identified as uncoupled antibody.

Example 4

Generation of Defined Covalent Conjugates of Haptenylated Dyes and Polypeptides with an Anti-Hapten Antibody VH52bC/VH53C in the Absence of Redox Agents For the generation of covalent anti-hapten antibody/haptenylated polypeptide or haptenylated dye disulfide-linked conjugates it is necessary to (i) couple the hapten (e.g. digoxigenin, fluorescein, biotin or theophylline) via a suitable a reactive group (such as e.g. cysteine, maleimide) containing linkers to the polypeptide or dye that allows the polypeptide to be exposed above the antibody surface and hence to retain its activity, and (ii) generate covalent site specific conjugates of the haptenylated polypeptides with the anti-hapten antibody with a cysteine mutation (=antibody VH52bC/VH53C) in which the biological activity of the polypeptide is retained, and (iii) to carry out the reaction in the absence of a reducing agent in order to avoid the reduction of antibody inter-chain disulfide bridges.

General Method:

The generation of conjugates of anti-hapten antibodies with haptenylated compounds shall result in conjugates with defined stoichiometry and it shall be assured that the compound in these conjugates retains its activity. For the generation of conjugates of haptenylated compounds with the respective anti-hapten antibody the haptenylated compound was dissolved in 100% DMF to a final concentration of 10 mg/ml. The anti-hapten antibody VH52bC/VH53C was brought to a concentration of 10 mg/ml in 50 mM Tris-HCl, 1 mM EDTA, pH=8.2. Haptenylated compound and anti-hapten antibody VH52bC/VH53C were mixed in a 2.5:1 molar ratio (compound to antibody) by pipetting up and down and incubated for 60 minutes at RT and 350 rpm.

A polypeptide conjugated to the hapten via a cysteine containing linker is termed hapten-Cys-polypeptide or polypeptide-Cys-hapten in the following. The polypeptide may either have a free N-terminus or a capped N-terminus e.g. with an acetyl-group (Ac-polypeptide-Cys-hapten) or a PEG-residue (PEG-polypeptide-Cys-hapten).

A fluorescent dye conjugated to the hapten via a cysteine containing linker is termed dye-Cys-hapten or hapten-Cys-dye in the following.

Exemplary Method for the Formation of Conjugates of Haptenylated Fluorescent Dyes and Anti-Hapten Antibodies—Dig-Cys-Ahx-Cy5/Anti-Digoxigenin Antibody VH52bC Samples were prepared exactly as described in Example 3a, with the difference that antibody-Dig-Cys-Ahx-Cy5 complexes were transferred to buffer containing either no redox compounds, 0.1 mM GSSG (oxidized glutathione) or 1 mM GSSG. The resulting fluorescence-scanned and Coomassie stained polyacrylamide gels are shown in FIG. 4. All three conditions show a similar specificity for site-specific disulfide bond formation (FIG. 4, top gels, lanes 1 A-C) with a low level of background reactions (FIG. 4, lanes 2 A-C). This confirms that formation of the disulfide bond can be accomplished without the need of reducing agents. This significantly stabilizes the antibody/reduces antibody disintegration, as only residual amounts of ¾ antibodies (~1× LC), HC-dimers (~2× LC) and ½ antibodies (1× HC+1× LC) are detected in comparison to Example 3.

Exemplary Method for the Formation of Conjugates of Haptenylated Fluorescent Dyes and Anti-Hapten Antibodies—Dig-Cys-Cy5/Anti-Digoxigenin Antibody VH52bC Samples were prepared exactly as described in Example 3b, with the difference that 13.3 nmol of antibody was mixed with 2 molar equivalents of Dig-Cys-Cy5 at a final antibody concentration of 10 mg/ml in the absence of redox reagents.

Exemplary Method for the Formation of Conjugates of Haptenylated Fluorescent Dyes and Anti-Hapten Antibodies—Biotin-Cys-Cy5/Chimeric Anti-Biotin Antibody VH53C For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the anti-biotin antibody VH53C was used in a concentration of 9.7 mg/ml (about 68 µM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 3a. Detection of fluorescence was carried out as described in Example 3a.

Exemplary Method for the Formation of Conjugates of Haptenylate Fluorescent Dyes and Anti-Hapten Antibodies—Biotin-Cys-Cy5/Humanized Anti-Biotin Antibody VH53C For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the humanized anti-biotin antibody VH53C was used in a concentration of 7.4 mg/ml (about 51 µM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 3a. Detection of fluorescence was carried out as described in Example 3a.

Exemplary Method for the Formation of Conjugates of Haptenylate Polypeptides and Anti-Hapten Antibodies—Ac-PYY(PEG3-Cys-4Abu-Dig)/Humanized Anti-Digoxigenin Antibody VH52bC For the generation of conjugates of digoxigenin-derivatized-PYY-polypeptide containing a cysteinylated linker, 2.4 mg of Ac-PYY(PEG3-Cys-4Abu-Dig) were dissolved in 20% acetate to a concentration of 5 mg/ml. 10 mg of the humanized anti-digoxigenin antibody VH52bC (68.4 nmol) was used in a concentration of 19.5 mg/ml (about 133 µM) in a buffer composed of 20 mM histidine, 140 mM NaCl, pH 6.0. Ac-PYY(PEG3-Cys-4Abu-Dig) and antibody were mixed at a 2:1 molar ratio (Ac-PYY(PEG3-Cys-4Abu-Dig) to antibody) and incubated for 60 min at RT, stirred at 100 rpm. The resulting conjugate was analyzed by mass spectrometry. 7.4% of the detected species was identified as antibody coupled to 2 peptide molecules, 40% was antibody coupled to 1 peptide molecule and 52% was identified as uncoupled antibody.

Exemplary Method for the Formation of Conjugates of Haptenylate Polypeptides and Anti-Hapten Antibodies—Ac-PYY(PEG3-Cys-βAla-Biot)/Chimeric Anti-Biotin Antibody VH53C For the generation of conjugates of biotin-derivatized-PYY-polypeptide containing a cysteinylated linker, 0.19 mg of Ac-PYY(PEG3-Cys-βAla-Biot) were dissolved in 100% DMF to a concentration of 10 mg/ml. 1 mg of the chimeric anti-biotin antibody VH53C was used in a concentration of 9.7 mg/ml (about 67 µM) in a buffer composed of 50 mM Tris-HCl, 1 mM EDTA, pH 8.2. Ac-PYY[PEG3-Cys-βAla-Biot and antibody were mixed at a 2.5:1 molar ratio (Ac-PYY[PEG3-Cys-βAla-Biot] to antibody) and incubated for 60 min at RT, shaken at 350 rpm. The resulting conjugate was analyzed by mass spectrometry. 87.7% of the detected species was identified as antibody coupled to 2 peptide molecules, 12.3% was identified as antibody coupled to 1 peptide molecule.

Exemplary Method for the Formation of Conjugates of Haptenylate Polypeptides and Anti-Hapten Antibodies—Ac-PYY(PEG3-Cys-PEG2-Biot)/Chimeric Anti-Biotin Antibody VH53C For the generation of conjugates of biotin-derivatized-PYY-polypeptide containing a cysteinylated linker, 0.16 mg of Ac-PYY(PEG3-Cys-PEG2-Biot) were dissolved in 100% DMF to a concentration of 10 mg/ml. 1 mg of the chimeric anti-biotin antibody VH53C was used in a concentration of 9.9 mg/ml (about 68 µM) in a buffer composed of 50 mM Tris-HCl, 1 mM EDTA, pH 8.2. Ac-PYY[PEG3-Cys-PEG2-Biot and antibody were mixed at a 2.5:1 molar ratio (Ac-PYY[PEG3-Cys-PEG2-Biot] to antibody) and incubated for 60 min at RT, shaken at 350 rpm. The resulting conjugate was analyzed by mass spectrometry. 100% of the detected species was identified as antibody coupled to 2 peptide molecules.

Exemplary Method for the Formation of Conjugates of Haptenylate Poly Peptides and Anti-Hapten Antibodies—Ac-PYY(PEG3-Cys-βAla-Biot)/Humanized Anti-Biotin Antibody VH53C For the generation of conjugates of biotin-derivatized-PYY-polypeptide containing a cysteinylated linker, 0.06 mg of Ac-PYY(PEG3-Cys-βAla-Biot) were dissolved in 100% DMF to a concentration of 10 mg/ml. 0.8 mg of the humanized anti-biotin antibody VH53C was used in a concentration of 9 mg/ml (about 62 μM) in a buffer composed of 50 mM Tris-HCl, 1 mM EDTA, pH 8.2. Ac-PYY[PEG3-Cys-βAla-Biot and antibody were mixed at a 2.5:1 molar ratio (Ac-PYY[PEG3-Cys-βAla-Biot] to antibody) and incubated for 60 min at RT, shaken at 350 rpm. The resulting conjugate was analyzed by mass spectrometry. 62.2% of the detected species was identified as antibody coupled to 2 peptide molecules, 33.9% was identified as antibody coupled to 1 peptide molecule and 3.9% was identified as uncoupled antibody.

Exemplary Method for the Formation of Conjugates of Haptenylate Polypeptides and Anti-Hapten Antibodies—Ac-PYY(PEG3-Cvs-PEG2-Biot)/Humanized Anti-Biotin Antibody VH53C For the generation of conjugates of biotin-derivatized-PYY-polypeptide containing a cysteinylated linker, 0.08 mg of Ac-PYY(PEG3-Cys-PEG2-Biot) were dissolved in 100% DMF to a concentration of 10 mg/ml. 0.8 mg of the humanized anti-biotin antibody VH53C was used in a concentration of 9 mg/ml (about 62 μM) in a buffer composed of 50 mM Tris-HCl, 1 mM EDTA, pH 8.2. Ac-PYY[PEG3-Cys-PEG2-Biot and antibody were mixed at a 2.5:1 molar ratio (Ac-PYY[PEG3-Cys-PEG2-Biot] to antibody) and incubated for 60 min at RT, shaken at 350 rpm. The resulting conjugate was analyzed by mass spectrometry. 71.4% of the detected species was identified as antibody coupled to 2 peptide molecules, 26% was identified as antibody coupled to 1 peptide molecule and 2.5% was identified as uncoupled antibody.

Exemplary Method for the Formation of Conjugates of Haptenylate Polypeptides and Anti-Hapten Antibodies—Ac-PYY(PEG3-Cvs-PEG2-Fluo)/Anti-Fluorescein Antibody VH52bC For the generation of conjugates of biotin-derivatized-PYY-polypeptide containing a cysteinylated linker, 0.33 mg of Ac-PYY[PEG3-Cys-PEG2-Fluo were dissolved in 100% DMF to a concentration of 10 mg/ml. 1 mg of the anti-fluorescein antibody VH52bC was used in a concentration of 9.3 mg/ml (about 63 μM) in a buffer composed of 50 mM Tris-HCl, 1 mM EDTA, pH 8.2. Ac-PYY[PEG3-Cys-PEG2-Fluo and antibody were mixed at a 2.5:1 molar ratio (Ac-PYY[PEG3-Cys-PEG2-Fluo] to antibody) and incubated for 60 min at RT, shaken at 350 rpm. The resulting conjugate was analyzed by mass spectrometry. 95% of the detected species was identified as antibody coupled to 2 peptide molecules, 5% was identified as antibody coupled to 1 peptide molecule.

Exemplary Method for the Formation of Conjugates of Haptenylate Polypeptides and Anti-Hapten Antibodies—Ac-PYY(PEG3-Cvs-PEG2-Fluo)/Anti-Fluorescein Antibody VH28C For the generation of conjugates of biotin-derivatized-PYY-polypeptide containing a cysteinylated linker, 0.33 mg of Ac-PYY[PEG3-Cys-PEG2-Fluo were dissolved in 100% DMF to a concentration of 10 mg/ml. 1 mg of the anti-fluorescein antibody VH28C was used in a concentration of 9.5 mg/ml (about 63 μM) in a buffer composed of 50 mM Tris-HCl, 1 mM EDTA, pH 8.2. Ac-PYY[PEG3-Cys-PEG2-Fluo and antibody were mixed at a 2.5:1 molar ratio (Ac-PYY[PEG3-Cys-PEG2-Fluo] to antibody) and incubated for 60 min at RT, shaken at 350 rpm. The resulting conjugate was analyzed by mass spectrometry. 100% of the detected species was identified as antibody coupled to two peptide molecules.

Example 5

Generation of Covalent Theophylline-Anti-Theophylline Antibody Complexes

To evaluate the formation of covalent antibody complexes that utilize theophylline and theophylline-binding antibodies as hapten recognition system, Theophyllin-Cys-Cy5 was generated as fluorescent payload, applying generally the synthesis and purification technologies that have been described for Digoxigenin-Cys-Cy5 or Biotin-Cys-Cy5, with the exception that the hapten has been exchanged against theophylline. To demonstrate the formation of a covalent disulfide, theophylline-binding antibodies were generated which contained a designed Cys at position 54 or 55 of the heavy chain variable region (anti-theophylline antibody-Cys). These antibody derivatives were complexed with Theophylline-Cys-Cy5 and subsequently subjected to SDS-PAGE under non-reducing and reducing conditions as described in Example 4. Under non-reducing conditions, disulfide-linked anti-theophylline-antibody complexed Cy5 was detected by its H-chain associated fluorescence within the gel in the same manner as described in Example 4. Covalent complexes had been formed as a consequence of the simple loading reaction in the same manner as the disulfides that were observed when using Digoxigenin, Fluorescein or Biotin as hapten. These complexes dissociated as expected upon reduction, i.e. released the payload from the H-chain only when the disulfide became reduced.

Example 6

Generation of Covalent Hapten-Antibody Complexes Under In-Vivo Like Conditions, and Evidence for Directed Disulfide-Formation In Vivo To evaluate the formation of covalent hapten-antibody complexes under in-vivo like conditions, anti-Biotin antibodies-Cys were incubated at 37° C. in murine serum with Biotin-Cys-Cy5 for 60 min. Subsequently, the antibody was captured from the murine serum by protein-A. Thereafter the captured antibodies were subjected to SDS-PAGE under non-reducing and reducing conditions as described in Example 4. Disulfide-linked antibody-complexed Cy5 was detected by its H-chain associated fluorescence within the gel in the same manner as described in Example 4. FIG. 10 demonstrates that covalent complexes between antibody form in serum at 37° C., i.e. under conditions that resemble the in-vivo conditions. These complexes dissociate as expected upon reduction, i.e. the payload is released from the H-chain only when the disulfide becomes reduced (FIG. 10). The observation that upon hapten-positioning a directed disulfide bond between antibody and payload can be formed even in the presence of serum is unexpected as serum contains a high amount of proteins, peptides and other compounds (which can interfere with disulfide-formation reactions). The observation that upon hapten-positioning a directed disulfide bond between antibody and payload can be formed in serum at 37° C. also opens the possibility to apply this PK-modulation system in a pre-targeting setting: separate application of antibody and hapten-payload, followed by in-vivo assembly of antibody complexes and subsequent disulfide formation.

To further evaluate potential in vivo 'pre-targeting' applications, the pharmacokinetics of Biotin-Cy5 was determined under pre-targeting conditions by the non-invasive optical imaging technology of the eye of animals as described in Example 10. In these experiments, the presence of Cy5 was determined non-invasive by optical imaging of the eye of animals, which revealed the fluorescence of Cy5 in the capillaries. The Cy5-mediated fluorescence values that we detected in the eye of mice 10 min. after injection of Biotin-Cy5 were set as 100% value, and fluorescence values measured at subsequent time points were expressed relative thereto. In this experiment, 1 mg antibody (either anti-Biotin antibody or anti-Biotin antibody-Cys (=Cys-mutant of anti-Biotin antibody)) was applied 24 hours before injection of Biotin-Cy5 and start of the eye imaging. The control group was not pre-injected with the anti-biotin antibody.

The results of these experiments are shown in FIG. 11: injection of Biotin-Cy5 into animals that did not receive pre-injected antibody was eliminated with a low serum half-life and low exposure levels (diamonds). The serum levels and half-life of Biotin-Cy5 that was injected into animals with 24 hours pre-injection of anti-Biotin antibody (without Cys mutation) were greatly increased. This shows that the antibody captures its antigen (with the payload) in the circulation, and prolongs the antigen's (and likewise of the conjugated payload) serum half-life. The relative serum level and half-life of Biotin-Cys-Cy5 that was injected into animals that were 24 hours pre-injected with the anti-Biotin antibody-Cys (i.e. an antibody containing the Cys mutation as reported herein for covalent payload coupling) were even further increased. In these samples, the relative Cy5 levels were not only higher than those of non-complexed compound, but also higher than the levels of complexed (but not disulfide-bonded) Cy5. Thus, hapten-complexed disulfide-linked payloads (which are formed under pre-targeting conditions in vivo) are more stable in the circulation, and can reach higher exposure levels, than non-covalent complexed payloads.

Example 7

Polypeptides in Conjugates and in Complexes with Anti-Hapten Antibody Retain Functionality We have previously shown that polypeptides which are part of non-covalent hapten-polypeptide conjugates and in complexes with anti-hapten antibodies retain functionality (WO2011/003557, WO 2011/003780 and PCT/EP2011/074273). To demonstrate that coupled peptides retain functionality also upon covalent disulfide-coupling, the biological activity of anti-digoxigenin antibody complexed polypeptides and their disulfide-conjugates with anti-digoxigenin antibody VH52bC were compared.

The therapeutically desired functionality of PYY-derived peptides is binding to and interfering with the signaling of its cognate receptor NPY2. Signaling via the NPY2 receptor is involved in and/or regulates metabolic processes.

To evaluate whether complexation or SS-conjugation of the polypeptide Dig-PYY with the anti-digoxigenin antibody or the conjugation of the polypeptide Dig-Cys-PYY with the anti-digoxigenin antibody VH52bC, respectively, affect its activity, we evaluated its ability to inhibit the Forskolin stimulated cAMP accumulation in HEK293 cells expressing the $NPY_2$ receptor (cAMP assay).

The following Table 2 shows the results of cAMP-assays that were performed to assess the biological activity of PYY(3-36), its Y2receptor specific modified analog moPYY, its antibody-complexed Dig-variant and its disulfide-conjugated Dig-Cys-derivative.

TABLE 2

| sample | day 1 $EC_{50}$ [nM] | day 2 $EC_{50}$ [nM] |
|---|---|---|
| $PYY_{wt}$ | 0.09 | 0.1 |
| moPYY | 0.14 | 0.15 |
| moPYY(Cys-Dig)-disulfide conjugated-anti-digoxigenin antibody VH52bC | 5.38 | 5.33 |
| moPYY(Dig)-anti-digoxigenin antibody complex | 9.26 | 12.55 |

For the cAMP agonist assay, the following materials were used: 384-well plate; Tropix cAMP-Screen Kit; cAMP ELISA System (Applied Biosystems, cat. #T1505; CS 20000); Forskolin (Calbiochem cat. #344270); cells: HEK293/hNPY2R; growth medium: Dulbecco's modified eagle medium (D-MEM, Gibco); 10% Fetal bovine serum (FBS, Gibco), heat-inactivated; 1% Penicillin/Streptomycin (Pen 10000 unit/mL: Strep 10000 mg/mL, Gibco); 500 µg/mL G418 (Geneticin, Gibco cat. #11811-031); and plating medium: DMEM/F12 w/o phenol red (Gibco); 10% FBS (Gibco, cat. #10082-147), heat-inactivated; 1% Penicillin/Streptomycin (Gibco, cat. #15140-122); 500 µg/mL G418 (Geneticin, Gibco, cat. #11811-031).

To perform the assay, on the first day, medium was discarded, and the monolayer cells were washed with 10 mL PBS per flask (T225). After decanting with PBS, 5 mL VERSENE (Gibco, cat #1504006) was used to dislodge the cells (5 min @ 37° C.). The flask was gently tapped and the cell suspension was pooled. Each flask was rinsed with 10 mL plating medium and centrifuged at 1000 rpm for 5 min. The suspension was pooled and counted. The suspension was resuspended in plating medium at a density of $2.0 \times 10^5$ cells/mL for HEK293/hNPY2R. 50 microliters of cells (HEK293/hNPY2R—10,000 cells/well) were transferred into the 384-well plate using Multi-drop dispenser. The plates were incubated at 37° C. overnight. On the second day, the cells were checked for 75-85% confluence. The media and reagents were allowed to come to room temperature. Before the dilutions were prepared, the stock solution of stimulating compound in dimethyl sulphoxide (DMSO, Sigma, cat #D2650) was allowed to warm up to 32° C. for 5-10 min. The dilutions were prepared in DMEM/F12 with 0.5 mM 3-Isobutyl-1-methylxanthine (IBMX, Calbiochem, cat #410957) and 0.5 mg/mL BSA. The final DMSO concentration in the stimulation medium was 1.1% with Forskolin concentration of 5 µM. The cell medium was tapped off with a gentle inversion of the cell plate on a paper towel. 50 µL of stimulation medium was placed per well (each concentration done in four replicates). The plates were incubated at room temperature for 30 min, and the cells were checked under a microscope for toxicity. After 30 min of treatment, the stimulation media was discarded and 50 µL/well of Assay Lysis Buffer (provided in the Tropix kit) was added. The plates were incubated for 45 min @ 37° C. 20 µL of the lysate was transferred from stimulation plates into the pre-coated antibody plates (384-well) from the Tropix kit. 10 µL of AP conjugate and 20 µL of anti-cAMP antibody were added. The plates were incubated at room temperature while shaking for 1 hour. The plates were then washed 5 times with Wash Buffer, 70 µL per well for each wash. The plates were tapped to dry. 30 μL/well of CSPD/Sapphire-II RTU substrate/enhancer solution was added and incubated for 45 min @ RT (shake). Signal for 1 sec/well in a Luminometer. (VICTOR-V) was measured.

The results of these assays (Table 2) show that the modified peptide derivative moPYY has a neglectable lower activity than the wild-type PYY. The $IC_{50}$ value of the cAMP assay was 0.09 nM for the wild-type PYY and 0.14 nM for the modified analog. Covalent disulfide-conjugation resulted to a slight reduction in biological activity. The $IC_{50}$ value was 5-36 nM for the conjugate. Surprisingly the covalent disulfide-conjugate is 2-fold more active than the non-covalent complex with an $IC_{50}$ value of 10.91 nM.

Example 8

Serum Stability of Complexes of Biotinylated Cy5 with Humanized Anti-Biotin Antibody in Comparison to Covalent Conjugates of Biotinylated Cy5 with Humanized Anti-Biotin Antibody VH53C The objective of the described peptide modification technology is to improve the therapeutic applicability of peptides. Major bottlenecks for therapeutic application of peptides are currently limited stability in vivo and/or short serum half-life and fast clearance. The PK parameters of antibody conjugates of fluorophores were determined in vivo and compare with the PK of non-covalent antibody-fluorophore complexes. Therefore, (i) the anti-biotin antibody VH53C was covalently conjugated to the biotinylated fluorophore Biot-Cys-Cy5, (ii) a non-covalent complex of the anti-biotin antibody with biotinylated fluorophore Biot-Cy5 was generated, (iii) the covalently conjugated and the non-covalently complexed compounds were applied to animals and (iv) the serum concentrations of the compounds over time in these animals was measured by determination of the fluorescence of Cy5 (A650), and that of the corresponding antibody by an ELISA method that specifically detects the humanized antibody.

Experimental Procedure

To analyze the influence on PK parameters of antibody-complexation of a small fluorescent substrate, 13 nmol of Cy5-biotin/humanized anti-biotin antibody VH53C-conjugate, or of the corresponding antibody non-covalently complexed compound, or of the fluorescent compound alone, in 20 mM histidine/140 mM NaCl, pH 6.0 were applied to six female mice (strain NRMI) for each substance. About 0.1 ml blood samples were collected after the following time points: 0.08 h, 4 h and 48 h for Mouse 1, 2, and 3 in a first group, and 0.08 h, 24 h and 72 h for Mouse 1, 2 and 3 in a second group. Serum samples of at least 50 μl were obtained after 1 h at RT by centrifugation (9300×g, 3 min, 4° C.). Serum samples were stored at −80° C.

To determine the amount of compound in the serum at the given time points the fluorescent properties of Cy5 are used: Cy5 related fluorescence in serum samples were measured in 120 μl quartz cuvettes at room temperature using a Cary Eclipse Fluorescence Spectrophotometer (Varian). Excitation wavelength was 640 nm, Emission was measured at 667 nm. Serum samples were diluted in 1×PBS to reach an appropriate range of Emission intensity. Blood serum of an untreated mouse in the same dilution in 1×PBS as the respective sample was used as a blank probe and did not show any fluorescence signal.

FIG. 5 shows the results of an analysis employing covalent conjugates, non-covalent complexes and non-complexed hapten-Cy5. The data is shown as relative (%) levels of Cy5-mediated fluorescence normalized to the (peak) serum levels 5 min after injection. For a compound of rather small molecular weight, non-complexed Biotin-Ser-Cy5 disappears rapidly from the serum. One hour after injection, only 6% of the fluorescence that was applied and detectable after 5 minutes in the serum was still detectable. At later time points, 2 hrs., 4 hrs. and 24 hrs. after injection, Cy5-mediated signals were not detectable.

Of the antibody-complexed compound four hours after injection, still approx. 50% of the fluorescence that was applied (5 min levels set to 100%) was detectable in the serum. Cy5-mediated fluorescence levels were also detectable at later time points with approx. 22% of the 5 min values detectable at 2 hrs. and approx. 12% detectable 48 hrs. after injection and 8% still detectable after 72 hrs. The antibody-conjugated compound shows a significantly longer in vivo half-life than the antibody-complexed compound. Four hours after injection 58% of the fluorescence that was applied (5 min. levels set to 100%) was still detectable in the serum (a factor of 1.16 higher than for the antibody-complexed compound). After 24 hrs. 35% (factor 1.6), after 48 hrs. 31% (factor 2.6) and after 72 hrs. 26% (factor 3.3) of the Cy5-mediated fluorescence was detected in serum. The comparable decrease of fluorescence for complexed and conjugated compounds in the first 24 hrs. of the experiments can be accounted for the early distribution which is similar for complexes and conjugates. After 24 hrs. the in vivo stability of antibody-conjugated compounds is responsible for the difference.

To determine the amount of human IgG antibody in the serum at the given time points, the following assay principle was used: human IgG1 antibodies in serum samples were captured on a solid phase (Maxisorb® microtiter plate, NUNC-Immuno™) coated with an anti-human kappa-chain monoclonal IgG antibody. Serum samples were diluted 1:$10^5$ and 1:$10^6$ and 100 μl of these dilutions were added to the wells. After incubation, wells were washed 3-times with 300 μl PBS/0.05% Tween 20 each. Detection of human IgG antibodies was carried out by first adding 100 μl of anti-human $C_H1$-domain IgG which is digoxigenylated at the C-terminus at a concentration of 0.25 μg/ml. After washing 3-times with 300 μl of 1×PBS/0.05% Tween 20 each, 100 μl of anti-digoxigenin antibody Fab-fragment conjugated to horse-radish peroxidase (HRP) was added at a concentration of 25 mU/mL. Finally, per well 100 μl of ABTS® were added. After 30 min. incubation at ambient temperature, the extinction (OD) was measured at 405 nm and 492 nm [405/492] in a commercial microtiter plate ELISA Reader (e.g. Tecan Sunrise).

FIG. 5 shows the Bio-Cy5 serum levels as well as the serum levels of human IgG in mice treated with antibody-biotin-Cy5-complexes and -conjugates. The data is shown as relative (%) human IgG levels normalized to the (peak) serum levels 5 min. after injection. The relative human IgG serum levels of both antibody-hapten-complexes and -conjugates are in-line with the relative fluorescence measured for the antibody-hapten conjugates. Thus, the Biotin-Cys-Cy5 compound shows a similar in vivo stability as the antibody it is conjugated to, which means that antibody-hapten conjugates stay intact in vivo. This is clearly not the case for antibody-hapten complexes for which the relative Cy5-mediated fluorescence decreases faster than the relative human IgG serum levels. This means that the complexes release the payload over time in vivo.

In summary, the in vivo stability of haptenylated compounds is significantly increased when bound by an anti-hapten antibody. However, antibody-hapten complexes are not completely stable in vivo as the decrease of the hapten- Cy5 serum levels is faster than the decrease of antibody serum levels. This is not the case for antibody-hapten-Cy5 conjugates, which show a similar in vivo behavior as normal IgG antibodies.

Dig-Peptide Serum Kinetic (Comparison of Non-Covalent Complex and Covalent Conjugate)

To analyze the influence on PK parameters of antibody-complexation and antibody conjugation of the digoxigenylated polypeptide, 32.1 nmol of the polypeptide, or of the corresponding antibody non-covalently complexed polypeptide in 20 mM histidine/140 mM NaCl pH 6.0 were applied to 2 female mice (strain NRMI) for each substance. The mice had a weight of 23 g and 25 g for MAK-DIG-PYY and 28 g and 26 g for DIG-PYY. About 0.1 ml blood samples were collected after the following time points: 0.08 h, 2 h and 24 h for Mouse 1 and 0.08 h, 4 h 24 h for Mouse 2. Serum samples of at least 40 µl were obtained after 1 h at RT by centrifugation (9300×g, 3 min, 4° C.). Serum samples were stored at −80° C.

The determination of the amount of digoxigenylated peptide in the serum at the given time points was difficult compared to the detection of Dig-Cy5 as no direct means to detect the polypeptide in serum samples was available. Therefore, a Western-Blot related assay to detect digoxigenylated peptide in serum was established. In a first step, the serum samples were separated on reducing SDS-PAGE. Because sample preparation included exposure of the serum to high concentrations of SDS and reducing agents, complexed Dig-polypeptide conjugates can become released from the (completely denatured/unfolded) anti-digoxigenin antibody, whereas covalently conjugates remained bound. To mediate the release of the polypeptide from the non-covalent antibody complex and separate the individual components by SDS-PAGE, 2 µl of each serum sample was diluted in 18 µl 20 mM histidine/140 mM NaCl pH 6.0, mixed with 6.7 µl of 4×LDS sample buffer and 3 µl of 10× sample reducing agent (NuPAGE, Invitrogen) for 5 min at 95° C. As a control, 2 µl of serum of an untreated mouse of the same strain was used. Samples were applied to a 4-12% Bis-Tris Gel (NuPAGE, Invitrogen) which was run at 200 V/120 mA for 20 minutes using 1×MES (Invitrogen) as a running buffer. Subsequently, separated polypeptides were blotted onto a PVDF membrane (0.22 µm pore size, Invitrogen) using the XCell Sure Lock® Mini-Cell system (Invitrogen) for 40 min at 25 V/130 mA. Membranes were blocked in 1% skim milk in 1×PBS+1% Tween20 (PBST) for 1 h at RT. Digoxigenylated polypeptides were subsequently detected on the membrane with an anti-digoxigenin antibody. For that, anti-digoxigenin antibody was applied to the membranes in a concentration of 13 µg/ml in 10 ml of 1% skim milk/PBST for 2 h at RT. Membranes were washed for 3×5 min in 1×PBST. Anti-mouse IgG Fab-fragments coupled to POD from the LumiLight$^{PLUS}$ Western Blotting Kit (Roche) was applied in a 1:25 dilution in 10 ml of 1% skim milk/PBST for 1 h at RT. Membranes were washed 3×5 min with 1×PBST. Detection was carried out by incubating the membranes in 4 ml LumiLight Western Blotting substrate for 5 min at RT. Chemiluminescence was detected with the LumiImager F1 (Roche) with an exposure time of 20 min.

The results of these analyses are shown in FIGS. 6A and 6B. The presence/amount of the digoxigenin polypeptide in murine serum at different time points has been determined. Mice that had received antibody complexed peptides (FIG. 6 left) showed strong signals at the earliest time point (5 min after administration). These signals were clearly assignable as shown by the size and location on the blot of the controls. In sera of mice that were treated with antibody-complexed polypeptide, polypeptide-associated signals were strongest at the early time points and decreased over time. Nevertheless, polypeptide was still detectable with good signals at all time points and even 24 hrs. after administration.

In mice that received non-complexed polypeptide, barely any signal associable to the small polypeptide was detectable even at the earliest time point. FIG. 6 shows in the right that under normal exposure conditions, no free polypeptide is visible on the blot. Contrast enhancement of the blot revealed the presence of some polypeptide 5 min after administration, however only in trace amounts. At later time points, no defined polypeptide band was detectable.

It can be seen that non-complexed polypeptide has a very short half-life in the serum of mice. Mice that received the same polypeptides but in antibody complexed form, show presence of these polypeptides in the serum for an increased period of time. Twenty four hours after injection polypeptide can be determined in the serum of these mice.

Example 9

Serum Half-Life of Covalently Linked Digoxigenin-Antibody Complexes and Digoxigenin-Binding IgGs To analyze if the covalent complexation further improves the PK-properties in view of the non-covalently linked hapten complexes, the PK parameters of anti-digoxigenin antibody-Digoxigenin-Cy5 complexes, as well as of the covalently linked [anti-digoxigenin antibody-Cys]-[Digoxigenin-Cys-Cy5] conjugates were determined in vivo. Therefore, Digoxigenin-Cy5 was determined using its fluorescence (A650), and the corresponding antibody was determined by an ELISA method that specifically detects the humanized antibody. Digoxigenin-Cy5 was applied as low molecular weight 'surrogate' for hapten-coupled peptides because its fluorescent properties allow easy and accurate detection in the serum.

In the same manner as described for Biotin-Cy5 or Biotin-Cys-Cy5 (see Example 8), Digoxigenin-Cy5 or antibody-complexed or additionally antibody-Cys-linked Digoxigenin-Cy5 were injected intravenously into female NRMI mice, followed by collection of blood at 0.08 h, 2 h, 4 h and 24 h. The Cy5-mediated fluorescence values detected for/in both mice 5 min. after injection (t=0.08 hrs.) was set as 100% value and fluorescence values measured at subsequent time points were expressed relative thereto.

The results of these experiments demonstrate that for Digoxigenin-Cy5 less than 10% of the fluorescence that was applied (5 min. value) was detectable 2 hours after injection. At later time points, 4 hrs. and 24 hrs., respectively, after injection no Cy5-mediated signals were detectable (see FIG. 8). In contrast to non-complexed compound, antibody-complexed compound was detectable at much higher levels and at later time points (FIG. 8). This indicates that antibody complexation significantly increases the serum half-life of the small compound Digoxigenin-Cy5. Furthermore, covalently linked payloads display a greater PK prolongation compared to the non-covalently linked complexes. A direct comparison of the Digoxigenin-Cy5 levels and antibody levels indicated payload loss from the antibody over time, with Cy5 levels decreasing faster than antibody levels. In contrast, covalently linked Digoxigenin-conjugates showed almost identical Cy5 and IgG serum half-lives (FIG. 8). This indicates that the disulfide-inked payloads remain stably connected to the antibodies while the non-covalent complexes dissociate over time.

Example 10

Serum Half-Life and Exposure Levels of Covalently Linked Hapten-Antibody Complexes and Complexes which are Only Attached Via the Hapten-Binding Site To analyze if the covalent complexation improves the PK-properties of non-covalently linked hapten complexes, the PK of a complex of anti-biotin antibody with Biotin-Cy5, as well as that of the covalently linked conjugate [anti-biotin-antibody-Cys]-[Biotin-Cys-Cy5] in vivo were determined. The presence of Cy5 was determined non-invasive by optical imaging of the eye of animals, which revealed the fluorescence of Cy5 in the capillaries. The Cy5-mediated fluorescence values that we detected in the eye of mice 10 min. after injection was set as 100% value, and fluorescence values measured at subsequent time points were expressed relative thereto. The results of these experiments are shown in FIG. 9: non-complexed Biotin-Cy5 by itself has a low serum half-life and low exposure levels. Antibody-complexed compound which was not covalently linked was detectable at much higher levels and with an extended half-life. Furthermore, covalently linked payloads displayed a greater PK prolongation, and higher serum levels compared to the non-covalently linked complexes. This indicates that hapten-complexed disulfide-linked payloads are more stable in the circulation, and can reach higher exposure levels, than non-covalent complexed payloads.

Example 11

Peptide-Complexation and Covalent Conjugation with Antibodies that Bind Different Haptens The application of hapten binding modules to couple haptenylated compounds (=payloads) to targeting vehicles is one technical possibility by which hapten-mediated delivery can be realized. The concept can be expanded to further haptens or other entities that capture compounds and connect them to the targeting module. For example, for polypeptide delivery or stabilization, mono- or bispecific antibodies that bind digoxigenin or other haptens can be applied to stabilize and PK-optimize therapeutic polypeptides.

Prerequisites for application as polypeptide capturing modules are (i) that coupling of compounds to the hapten does not severely interfere with polypeptide activity and (ii) the possibility of effective binding/complexation of the antibody to haptenylated compounds.

Hapten-directed binding is a prerequisite for the efficient covalent coupling of haptenylated dyes or polypeptides with an anti-hapten cysteinylated antibody.

To show that affinity-driven complexation of haptenylated compounds with anti-hapten antibodies is a prerequisite for efficient disulfide-bond formation, Biotin-Cys-Cy5 was incubated with humanized anti-digoxigenin antibody and humanized anti-digoxigenin antibody VH53C. Incubation of Biotin-Cys-Cy5 with humanized anti-biotin antibody and humanized anti-biotin antibody VH53C was carried out as a control reaction.

0.13 mg of Biotin-Cys-Cy5 were dissolved in 100% DMF to a concentration of 10 mg/ml. 0.7 mg of each antibody was used in a concentration of 6.7 mg/ml (about 46 µM) in a buffer composed of 50 mM Tris-HCl, 1 mM EDTA, pH 8.2. Biotin-Cys-Cy5 and antibodies were mixed at a 2.5:1 molar ratio (Ac-Biotin-Cys-Cy5 to antibody) and incubated for 60 min at RT, shaken at 350 rpm. The resulting complex/conjugate was further analyzed by SDS-PAGE and subsequent detection of Cy5-related fluorescence in the polyacrylamide-gel. 15 µg of the complex/conjugate were mixed with 4×LDS sample buffer (Invitrogen) and incubated at 95° C. for 5 min. Cy5-related fluorescence was recorded using a LumiImager F1 device (Roche) at an excitation wavelength of 645 nm.

The non-reduced samples show covalent site-specific disulfide bond formation for humanized anti-biotin antibody VH53C (FIG. 36, lane 4) with very low background fluorescence signal when humanized anti-biotin antibody without a cysteine in CDR2 was used (FIG. 36, lane 3). Biotin-Cys-Cy5 was also covalently coupled to humanized anti-digoxigenin antibody VH52bC (FIG. 36, lane 2) with a low background signal when humanized anti-digoxigenin antibody was used (FIG. 36, lane 1), but with significantly lower efficiency. This can be deduced from the excess Biotin-Cys-Cy5 that is detected on the bottom of the gel (arrows). In the case of humanized anti-digoxigenin antibody VH52bC significantly more uncoupled Biotin-Cys-Cy5 can be detected (lane 2) than with humanized anti-biotin antibody VH53C (lane 4). Upon reduction of the samples, no Cy5-related fluorescence is detectable near the antibody heavy- and light-chains, indicating that the covalent linkage was indeed formed by a disulfide bridge. Coomassie stains of each gel show that the total amount of protein in each lane was equal.

Example 12

Hapten-Directed Binding is a Prerequisite for the Efficient Covalent Coupling of Haptenylated Dyes or Polypeptides with an Anti-Hapten Cysteinylated Antibody To show that affinity-driven complexation of haptenylated compounds with anti-hapten antibodies is a prerequisite for efficient disulfide-bond formation, the non-haptenylated peptide Ac-PYY(PEG3-Cys-4Abu-NH2) (Biosynthan 1763.1, SEQ ID NO: 23) was incubated with humanized anti-digoxigenin antibody VH52bC and humanized anti-digoxigenin antibody. 1.4 mg of Ac-PYY(PEG3-Cys-4Abu-NH2) were dissolved in 100% DMF to a concentration of 10 mg/ml. 2 mg of each antibody was used in a concentration of 11-13 mg/ml (about 75-89 µM) in a buffer composed of 50 mM Tris-HCl, 1 mM EDTA, pH 8.2. Ac-PYY(PEG3-Cys-4Abu-NH2) and antibodies were mixed at a 2.1:1 molar ratio (Ac-PYY(PEG3-Cys-4Abu-NH2 to antibody)). The peptide was added in 3 portions while the solution was stirred at 500 rpm with a stirrer bar. Between each addition, samples were incubated for 5 min at 200 rpm. After addition of the last portion, samples were incubated for 1 h at RT and 200 rpm.

The resulting complex/conjugate was defined as 97% monomeric IgG-like molecule and 3% dimeric soluble aggregates for the Ac-PYY(PEG3-Cys-4Abu-NH2): humanized anti-digoxigenin antibody VH52bC conjugate and as 100% monomeric for the Ac-PYY(PEG3-Cys-4Abu-NH2): humanized anti-digoxigenin antibody complex via size exclusion chromatography. Furthermore, the resulting complex/conjugate was analyzed by mass spectrometry. For the Ac-PYY(PEG3-Cys-4Abu-NH2): humanized anti-digoxigenin antibody VH52bC conjugate 17% of the detected species was identified as antibody coupled to 2 peptide molecules, 51% was identified as antibody coupled to 1 peptide molecule and 32% was identified as antibody without coupled peptide. For the Ac-PYY(PEG3-Cys-4Abu-NH2): humanized anti-digoxigenin antibody complex 100% of the antibody was uncoupled.

Example 13

Disulfide Patterns that are Required for Formation of Properly Folded Functional Hapten-Binding Antibodies with a Cysteine Mutation for Covalent Payload Coupling Hapten-binding modules for covalent compound/payload coupling may be composed of 'standard' antibodies such as IgGs which contain extra cysteines that enable covalent attachment of haptenylated compounds/payloads. The method as reported herein introduces the required functionalities (cysteines) within folded domains, whose structure and sequence provide the basis for antibody functionality. Correct formation of defined disulfide bonds within as well as between the domains of antibodies is essential for the formation and maintenance of the correct structure and functionality. To maintain the proper disulfide pattern, the additional cysteine that was introduced in the VH domain must be unoccupied and must not interfere or react with neighboring cysteines. The fact that the VH52bC/VH53C position is located within the VH domain (and quite close to other cysteines) aggravates the risk that incorrect disulfides may be formed during the biosynthesis of the heavy chain. Another potential problem is that VH and VL domains become assembled within the secretory pathway to one Fv fragment. The secretory pathway involves redox-shuffling conditions and disulfide forming and -shuffling enzymes. Therefore, the potential to introduce incorrect disulfides by addition of the VH52bC/VH53C mutation may 'spread' also to disulfides of the light chain. This does further enhance the risk to obtain/generate improperly folded non-functional molecules. It is therefore quite surprising that—despite of these risks—good amounts of homogeneous functional antibody derivatives that contain the VH52bC/VH53C mutation could be expressed and obtained, and which are capable to covalently connect to haptenylated compounds/payloads.

Example 14

Composition and Generation of Anti-Hapten Disulfide-Stabilized Single-Chain Fv Fragments with a Cysteine Mutation for Covalent Coupling Hapten-binding modules for covalent compound/payload coupling can consist of 'standard' antibodies such as IgGs. Alternatively, they may be modified entities such as recombinant Fv or Fab fragments, or derivatives thereof. Single-chain Fv fragments are frequently applied as alternative to full lengths antibodies, especially in applications where small module size is required, or where additional binding modules are desired to generate bi- or multispecific antibody derivatives. One example for anti-hapten Fv-derived entities that have been generated is a disulfide-stabilized single-chain Fv which bind to and covalently connects digoxigenylated compounds/payloads. The disulfide-stabilized single-chain Fv with Dig-binding specificity was generated by connecting anti-digoxigenin antibody VH and VL domains via a flexible Gly and Ser rich linker to each other. These VH and VL domains harbored in addition cysteine mutations in positions 44 of VH and position 100 of VL (positions according to Kabat et al.). These additional cysteines form a stable intermolecular disulfide bond between VH and VL. This stabilizes the scFv, as previously described (e.g. Reiter, Y., et al., Nature Biotechnology 14 (1996) 1239-1245).

In addition to that, another cysteine was introduced into the VH at position 52b or 53, respectively, according to the Kabat numbering to add the covalent linkage functionality to the Fv fragment.

However, introducing such a mutation into disulfide-stabilized Fv fragments is far more challenging than placing them into full length antibodies. Single-chain Fv fragments are inherently less stable than full length IgGs or Fab fragments because they lack constant domains as stabilizing and heterodimerization forcing entities. Stability can be conferred by placing additional cysteine mutations into the Fvs such as the VH44-VL100 disulfide. However, this stabilizing principle works only if the disulfide forms at the correct positions between correct cysteines. Thus, in addition to defined intradomain disulfides (one in VH and one in VL), one single defined correct interdomain disulfide needs to be formed. Disulfide connections between non-matching cysteines will generate misfolded instable and non-functional entities. Considering that a disulfide-stabilized Fv fragment contains 6 cysteines, 21 different disulfide connections can theoretically be formed—but only the right combination of 3 defined disulfides will form a functional stabilized dsscFv. This challenge is aggravated upon addition of another free cysteine into the VH domain. The stabilized dsscFv that is desired contains two defined intradomain disulfides (one each in VH and VL), one defined interdomain disulfide (between VH and VL), and furthermore one free cysteine for haptenylated compound/payload coupling (in VH at position 52b/53). Considering that a disulfide-stabilized Fv fragment with extra cysteine mutation for covalent coupling contains 7 cysteines, many different disulfide connections can theoretically be formed but only the right combination of the 3 defined disulfides, with the exact free cysteine position at VH52b/VH53 will result in a functional stabilized covalent coupling competent dsscFv. One additional challenge is the fact that the additional free cysteine (VH52b/VH53) is located in close proximity to the VH44 cysteine which is not a naturally occurring cysteine but a mutation introduced for disulfide stabilization. VH44C is necessary for forming the correct inter-domain disulfide, and this disulfide most likely without being bound by this theory forms after independent folding and assembly of VH and VL. Proximity of VH44C and VH52bC/VH53C aggravates the risk that the intradomain disulfide does not form in a correct manner. But it has been found that functional disulfide stabilized single-chain Fv modules that bind digoxigenin and that are simultaneously capable to covalently connect to digoxigenylated payloads can be produced. The sequences that encode the light chain variable regions and the modified heavy chain variable regions of this Dig-binding dsscFv with the VH52bC mutation Fv antibody derivative are listed under SEQ ID NO: 25 (VH) and the corresponding VL under SEQ ID NO: 24. The successful generation of such dsscFv as modules for the generation of bispecific antibody derivatives is described in the Example 15 (below).

Example 15

Composition, Expression and Purification of Bispecific Anti-Hapten Antibody Derivatives for Targeted Delivery of Covalently Coupled Compounds/Payloads Bispecific antibodies were generated that contain hapten-binding antibody modules for covalent compound/payload coupling. These antibodies additionally contain binding modules that enable targeting to other antigens. Applications for such bispecific antibodies include specific targeting of haptenylated compounds/payloads to cells or tissues that carry the targeting antigen. One example for such molecules that was generated is a bispecific antibody with binding regions that recognize the tumor associated carbohydrate antigen LeY, and simultaneously with disulfide-stabilized Fvs which bind and covalently connect digoxigenylated compounds/payloads. Therefore, disulfide-stabilized single-chain Fvs were connected via flexible Gly and Ser rich connector peptides to the C-termini of the CH3 domains of a LeY antibody, resulting in tetravalent molecules with two LeY binding arms and additionally two digoxigenin binding entities. The digoxigenin-binding entities harbored a VH44-VL100 disulfide bond which has been previously described (e.g. Reiter, Y., et al., Nature Biotechnology 14 (1996) 1239-1245). The digoxigenin binding entity contained in addition the VH52bC mutation for covalent coupling. The sequences that encode the light chain and the modified heavy chain of this LeY-Dig antibody derivative are listed under SEQ ID NO: 17 and SEQ ID NO: 18.

The bispecific molecules were generated by molecular biology techniques, expressed by secretion from cultured cells, subsequently purified from culture supernatants in the same manner as described above. Thus, bispecific antibodies which contain targeting modules as well as modules for covalent coupling of haptenylated compounds/payloads can be generated and purified to homogeneity.

Example 16

Helicar Motif Amino Acid Sequence Containing Peptide YY

Peptide YY is a short (36-amino acid) peptide released by cells in the ileum and colon in response to feeding. In humans it appears to reduce appetite. The most common form of circulating PYY is $PYY_{3-36}$, which binds to the Y2 receptor (Y2R) of the Y family of receptors. PYY is found in L cells in the mucosa of gastrointestinal tract, especially in ileum and colon. Also, a small amount of PYY, about 1-10%, is found in the esophagus, stomach, duodenum and jejunum. In the circulation, PYY concentration increases after food ingestion and decreases during fasting. PYY exerts its action through NPY receptors; it inhibits gastric motility and increases water and electrolyte absorption in the colon. PYY and PYY mimetics have been used to address obesity.

PYY was modified to comprise the helicar motif amino acid sequence and complexed by an anti-helicar motif amino acid sequence antibody in order to get advantage of the pharmacokinetic properties of the antibody and to avoid the intrinsic instability of the PYY.

Non-Covalent Complex Formation

The structural investigation of the $PYY_{3-36}$ peptide (Nygaard, R., et al., Biochem. 45 (2006) 8350-8357; SEQ ID NO: 26) reveals a helical motif (helicar-like motif amino acid sequence) for the central amino acids. As the N-terminal isoleucine and the modified C-terminus have been described as essential for the functional activity of the peptide, the central helix was modified in order to reflect the amino acids in the helicar motif amino acid sequence.

| PYY (3-36) (SEQ ID NO. 26) Helicar motif PYY_helicar (SEQ ID NO: 27) | 3 36 IKPEAPGEDASPEELNRYYASLRHYLNLVTRQRYNH2 AHLENEVARLKK IKPEAPGEDASPEAHLANEVARLHYLNLVTRQRYNH2 (YNH2 = tyrosine amide) |
|---|---|
| | binding [K_d]   soluble in PBS |
| PYY(3-36) (SEQ ID NO: 26) | —           +           PYY wild-type |
| PYY helicar (SEQ ID NO: 27) | 12 nM       +     helicar motif engineered PYY |

The full IgG1 anti-helicar motif amino acid sequence antibody was produced in HEK293 cells by transfecting two plasmids containing the variable regions of the heavy and the light chain inserted in a vector containing the constant human IgG1 and the constant human lambda domain, respectively. The anti-helicar motif amino acid sequence antibody (0019) was purified by standard procedures using protein A chromatography. A mass spectroscopy experiment confirmed the identity of antibody 0019.

The complex between antibody 0019 and the modified PYY peptide PYY_helicar was obtained in vitro by applying a small excess of the peptide to the antibody solution.

The complex 0052 was formed. The stoichiometry of the complex was determined by SEC-MALLS analytical experiments to be 1.6 peptides complexed on one bivalent antibody.

The antibody 0019, the PYY(3-36) wild-type, the PYY_helicar and the complex 0052 were tested for their effect on to the Y2Receptor family.

| | NPY2R | NPY1R | NPY4R | NPY5R |
|---|---|---|---|---|
| Ac-Ile-Lys-Pqa-Arg-His-Tyr-Leu-Asn-Trp-Val-Thr-Arg-Gln-(NMe)-Arg-Try-NH2 * 4 HOAc | 1.0 nM | inactive | inactive | inactive |
| PYY_helicar (IKPEAPGEDASPEAHLANEVARLH YLNLVTRQRYNH2) (SEQ ID NO: 27) | 6.38 nM | inactive | inactive | inactive |
| PYY(3 -36) (IKPEAPGEDASPEELNRYYASLRHY LNLVTRQRYNH2) (SEQ ID NO: 26) charge 1 | 0.05 nM | 168 nM | 162 nM | 170 nM |

| | | | | |
|---|---|---|---|---|
| PYY(3-36) (IKPEAPGEDASPEELNRYYASLRHY LNLVTRQRYNH2) (SEQ ID NO: 26) charge 2 | 0.05 nM | 160 nM | 131 nM | 202 nM |
| anti-helicar motif amino acid sequence antibody (0019) | inactive | inactive | inactive | inactive |
| anti-helicar motif amino acid sequence antibody-PYY_helicar complex (0052) | 0.93 nM | inactive | inactive | inactive |

As demonstrated (Hoffmann, E., et al., J. Cont. Rel. 171 (2013) 48-56.) the peptides complexed by an antibody have a prolonged half-life in vivo. Moreover and surprisingly, the complex demonstrates a slightly better affinity for the NPY2R receptor compared to the non-complexed peptide; the antibody stabilizes the polypeptide and presents the peptide in its fixed biologically active conformation.

Covalent Complex Formation (Covalent Disulfide Bond)

In order to increase the in vitro and in vivo stability of the complex between the anti-helicar motif amino acid sequence antibody and the helicar motif amino acid sequence containing compound, the formation of a disulfide bridge upon binding has been used.

The first step is a specific recognition step (high affinity interaction), i.e. the formation of the helicar motif amino acid sequence containing compound-anti-helicar motif amino acid sequence antibody complex. This is followed in the second step by a spontaneous shuffling of a disulfide bridge to form the stability improved covalent complex.

As the 12-mer peptide (helicar motif amino acid sequence) is a relatively rigid entity (at least when complexed by a specific anti-helicar motif amino acid sequence antibody) it has been found that a structurally specific design for the disulfide bridge has to be used. As the complex formation and the thereafter effected covalent coupling is between two recombinantly produced entities, the artificial cysteine residues introduced for the formation of a covalent disulfide bond are not produced necessarily as free cysteine residues but are expressed in a reduced from, i.e. conjugated to a free cysteine or homo cysteine amino acid.

The position in the amino acid sequence of the anti-helicar motif amino acid sequence antibody variable domain where the artificial free cysteine residue is introduced is critical. A non-exposed cysteine in the antibody variable domain amino acid sequence has more probability to be expressed as a free cysteine (not conjugated), whereas an exposed cysteine residue close to the binding pocket can abolish the binding of the 12-mer peptide (helicar motif amino acid sequence) due to a steric hindrance induced by the cysteine conjugation to an additional moiety like a free cysteine.

a) Complexes with a Helicar Motif Amino Acid Sequence Containing Fluorescent Compound In order to identify a suitable position which has minimum risk of steric hindrance and strong affinity reduction, different positions for the introduction of the artificial cysteine residue in the helicar motif amino acid sequence have been tested. The cysteine residue has been introduced at the C-terminal end of the 12 mer (helicar motif amino acid sequence) in order to have the major part of the paratope unchanged. The peptides have been synthesized and fused to a fluorescent motif

```
wild-type:          AHLENEVARLKK (SEQ ID NO: 1)

cysteine variant 1: AHLENEVARCKK (SEQ ID NO: 2)
                 -> AHLENEVARCKK (5-Fluo)-OH cysteine variant 2: AHLENEVARLCK (SEQ ID NO: 03)
                 -> AHLENEVARLCK (5-Fluo)-OH x TFA
```

On the antibody, a structural design has been done to allow the formation of the disulfide bridge for both designed peptides including each a cysteine in different 3D environment.

The 12-mer helical peptide AHLENEVARLKK (helicar motif amino acid sequence) is modeled into the VH and the VH domains. At the C-terminus of the peptide the residues L10 and K11 are identified as possible position and in the light chain variable domain the positions N55 and G51 according to the light chain numbering of Kabat are identified.

The heavy chain variable domain of the anti-helicar motif amino acid sequence antibody (0019) has the amino acid sequence:

```
                                              (SEQ ID NO: 04)
QAVVTQEPSL TVSPGGTVTL TCGSSTGAVT TSNYASWVQQ

KPGQAFTGLI GGTNNRAPWT PARFSGSLLG GKAALTLSGA

QPEDEAEYYC ALWYSNHWVF

GGGTKLTVL.
```

The light chain variable domain of the anti-helicar motif amino acid sequence antibody (0019) has the amino acid sequence:

```
                                              (SEQ ID NO: 05)
DAVVTQESAL TTSPGETVTL TCRSSTGAVT TSNYASWVQE
KPDHLFTGLI GGTNNRAPGV PARFSGSLIG DKAALTITGA
QTEDEAIYFC ALWYSNHWVF GGGTKLTVL.
```

The light chain variable domain N55C variant of the anti-helicar motif amino acid sequence antibody (0155) has the amino acid sequence:

```
                                      (SEQ ID NO: 06)
DAVVTQESAL TTSPGETVTL TCRSSTGAVT TSNYASWVQE
KPDHLFTGLI GGTNCRAPGV PARFSGSLIG DKAALTITGA
QTEDEAIYFC ALWYSNHWVF GGGTKLTVL.
```

The light chain variable domain N51C variant of the anti-helicar motif amino acid sequence antibody (0157) has the amino acid sequence:

```
                                      (SEQ ID NO: 07)
DAVVTQESAL TTSPGETVTL TCRSSTGAVT TSNYASWVQE
KPDHLFTGLI CGTNNRAPGV PARFSGSLIG DKAALTITGA
QTEDEAIYFC ALWYSNHWVF GGGTKLTVL.
``` i) Covalent Conjugate of Helicar Motif Amino Acid Sequence Containing Compound With Antibody 0155

The bivalent antibody 0155 is expressed in HEK293 cells similarly to its parent molecule Y2R(bck)-0019 without free cysteine. The modified antibody is purified using the same protocol used for antibody 0019. The mass spectrometry analysis shows that the experimentally determined mass of the deglycosylated antibody is 142,001 Da. This exceeds the calculated mass by 259 Da. The reduced chains have the experimentally determined mass of 48,167 Da (complete heavy chain, calculated 48,168 Da, Cys=SH, C-Term=-K) and 22,720 Da (complete light chain, N55C, calculated 22,720 Da, Cys=SH). The sequences of the chains were confirmed after reduction.

Antibody 0155 was coupled to the helicar motif amino acid sequence cysteine variant 2 using a 2.5 molar excess of helicar motif amino acid sequence containing compound in 100% DMF to form the covalent complex 0156.

On the SDS page (denaturing condition, see FIG. 12) the fluorescence is seen only on the antibody 0155; in the reducing condition, only the small peptide is visible.

Results:

The covalent conjugation of the helicar motif amino acid sequence containing fluorescent compound to the anti-helicar motif amino acid sequence antibody was successful. A total of about 43% of the anti-helicar motif amino acid sequence antibody was covalently conjugated to two helicar motif amino acid sequences, about 40% of the anti-helicar motif amino acid sequence antibody was covalently conjugated to one helicar motif amino acid sequence, and about 17% of the anti-helicar motif amino acid sequence was not conjugated.

The conjugate comprising two helicar motif amino acid sequences is modified to about 50%. This species has not been taken into account for the quantification. As already determined for the starting material the antibody without helicar motif amino acid sequence contains two modifications of about 128 Da. The antibody conjugated to one helicar motif amino acid sequence has only one modification of about 128 Da.

ii) Covalent Conjugate of the Helicar Motif Amino Acid Sequence Containing Compound with Antibody 0157

Similarly to antibody 0155 is antibody 0157 expressed mostly as a cysteinylated form. The mass spectrometry analysis shows that the experimentally determined mass of the deglycosylated antibody is 141,863 Da. This exceeds the calculated mass by 3 Da. The antibody is mainly present as single or double homocysteinylated form. The reduced chains have the experimentally determined mass of 48,168 Da (complete heavy chain, calculated 48,168 Da, Cys=SH, C-Term=-K) and 22,777 Da (complete light chain, N51C, calculated 22,777 Da, Cys=SH). The sequences of the chains were confirmed after reduction.

The coupling of antibody 0157 with the helicar motif amino acid sequence cysteine variant 1 was not resulting in the expected covalent complex. The fluorescence is not seen in the expected lane but on the reference which should be negative in this experiment (see FIG. 13).

Antibody 0157 was incubated with helicar motif amino acid sequence cysteine variant 1. As control antibody 0019 was incubated with the same helicar motif amino acid sequence cysteine variant 1.

Results:

The covalent conjugation of the helicar motif amino acid sequence containing fluorescent compound to the anti-helicar motif amino acid sequence antibody was not successful. Without being bound by this theory it is assumed that in this case the antibody cysteinylation is too deep in the binding pocket to allow the helicar motif amino acid sequence containing fluorescent compound to bind efficiently and deliver the nucleophilic thiol group in an appropriate position to attack the C51.

b) Complexes with helicar Motif Amino Acid Sequence Containing Recombinant Polypeptide The helicar based methodology becomes particularly attractive when considering the formation of a covalent complex with a recombinantly produced helicar motif amino acid sequence containing polypeptide.

As the conjugation of the antibody 0155 containing the VL-N55C mutation with the helicar motif amino acid sequence cysteine variant 1 (AHLENEVARLCK; SEQ ID NO: 02) has much better performed compared to the alternative (G51C on VL with helicar motif amino acid sequence cysteine variant 2 (AHLENEVARCKK; SEQ ID NO: 03)), the conjugation of 0155 with a helicar motif amino acid sequence cysteine variant 1 containing polypeptide was further investigated. The polypeptide contained the helicar motif amino acid sequence cysteine variant 1 (AHLENEVARLCK; SEQ ID NO: 02) fused to the N-terminus.

The helicar motif amino acid sequence cysteine variant 1 containing *Pseudomonas* exotoxin molecule LR8M with the C-terminal lysine residue deleted (0236; SEQ ID NO: 28) has been produced in *E. coli* and purified using a combination of anion exchange chromatography and SEC (see e.g. WO 2011/032022).

Antibody 0155 is covalently conjugated with the helicar motif amino acid sequence cysteine variant 1 containing *Pseudomonas* exotoxin molecule LR8M with the C-terminal lysine residue deleted of SEQ ID NO: 28. The SEC chromatogram is shown in FIG. 14. The conjugation efficiency is analyzed by SDS-CE, Caliper, for the non reduced samples (see FIG. 15).

A total of about 4% of the anti-helicar motif amino acid sequence antibody was covalently conjugated to two polypeptide of SEQ ID NO: 28, about 41% of the anti-helicar motif amino acid sequence antibody was covalently conjugated to one polypeptide of SEQ ID NO: 28, and about 55% of the anti-helicar motif amino acid sequence was not conjugated.

In conclusion, the anti-helicar motif amino acid sequence monoclonal antibody can be used to complex peptides, small molecules with peptidic linker, and recombinant proteins via a high affinity recognition of a 12-mer helicar motif amino acid sequence. Peptides with propensity to fold as helix can be modified to mimic the original 12-mer helicar motif amino acid sequence AHLENEVARLKK (SEQ ID NO: 01)

and are thereafter complexable with the anti-helicar motif amino acid sequence monoclonal antibody. In addition to the high affinity complexation, covalent conjugation is enabled with a cysteine variant of SEQ ID NO: 01 containing a cysteine and a modified anti-helicar motif amino acid sequence antibody containing a cysteine in the CDRs via formation a stable disulfide bond. Recombinant proteins expressed by different system can be conjugated afterwards in vitro without particular reactions conditions but via spontaneous disulfide bridge shuffling.

What is claimed is:

1. A conjugate comprising
   i) a compound comprising a helicar motif amino acid sequence selected from the group consisting of SEQ ID NO: 02 and SEQ ID NO: 03, and
   ii) an anti-helicar motif amino acid sequence antibody, wherein the antibody comprises hypervariable loops as in the variable domain of SEQ ID NO: 04 for the heavy chain and as in the variable domain of SEQ ID NO: 06 for the light chain variable domain.

2. The conjugate according to claim 1, wherein the helicar motif amino acid sequence containing compound is a polypeptide comprising the helicar motif amino acid sequence either fused to one of its termini or within the polypeptide sequence.

3. The conjugate according to claim 1, wherein the antibody is a bispecific antibody comprising a first binding specificity to a non-helicar motif amino acid sequence antigen and a second binding specificity to the helicar motif amino acid sequence.

4. The conjugate according to claim 1, wherein the disulfide bond is formed between the cysteine residues without the addition of a redox active agent.

5. An anti-helicar motif amino acid sequence antibody, wherein the antibody comprises hypervariable loops as in the variable domain of SEQ ID NO: 04 for the heavy chain and as in any of the variable domains of SEQ ID NO: 05, or SEQ ID NO: 06, or SEQ ID NO: 07 for the light chain variable domain.

6. A pharmaceutical formulation comprising the conjugate according to claim 1 and a pharmaceutically acceptable carrier.

7. A bispecific anti-helicar antibody for targeted delivery of a helicar motif amino acid sequence containing compound to a target cell, wherein the bispecific antibody comprises a first binding site that specifically binds to the helicar motif amino acid sequence containing compound and a second binding specificity that specifically binds to a cell surface marker of the target cell, wherein the first binding site comprises hypervariable loops as in the variable domain of SEQ ID NO: 04 for the heavy chain and as in any of the variable domains of SEQ ID NO: 05, or SEQ ID NO: 06, or SEQ ID NO: 07 for the light chain variable domain.

8. The antibody of claim 5, wherein the antibody is humanized.

9. The bispecific anti-helicar antibody of claim 7, wherein the antibody is humanized.

* * * * *